US006249339B1

(12) United States Patent
Jung et al.

(10) Patent No.: US 6,249,339 B1
(45) Date of Patent: *Jun. 19, 2001

(54) METHOD AND APPARATUS FOR DETECTING AND PREVENTING COUNTERFEITING

(75) Inventors: Wayne D. Jung; Russell W. Jung, both of Morton Grove; Alan R. Loudermilk, Chicago, all of IL (US)

(73) Assignee: LJ Laboratories, LLC, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/500,199

(22) Filed: Feb. 7, 2000

Related U.S. Application Data

(63) Continuation of application No. 09/360,529, filed on Jul. 26, 1999, now Pat. No. 6,038,016, which is a continuation of application No. 08/886,566, filed on Jul. 1, 1999, now Pat. No. 5,966,205.

(51) Int. Cl.[7] .................................................. G06K 9/74
(52) U.S. Cl. ............................................................ 356/71
(58) Field of Search .................................................. 356/71

(56) References Cited

U.S. PATENT DOCUMENTS

| 3,327,584 | 6/1967 | Kissinger ........................ 356/375 |
| 3,436,157 | 4/1969 | Adler et al. . | |

(List continued on next page.)

FOREIGN PATENT DOCUMENTS

| 2256355 | 12/1973 | (DE) . |
| 0681256 | 11/1995 | (EP) . |
| 2669526 | 5/1992 | (FR) . |
| 54-103055 | 8/1979 | (JP) . |
| 8603292 | 6/1986 | (WO) . |

OTHER PUBLICATIONS

Aswell, Cecil J. et al., "A Monolithic Light–to–Frequency Converter with a Scalable Sensor Array", IEEE, 1994, pp. 122–123 and 158–159.

Bangtson et al.; "The conversion of Chromascan designations to CIE tristimilus values"; Nov. 1982; pp 610–617 vol. 48 No. 5, Journal of Prosthetic Dentistry.

Barghi et al.; "Effects of batch variation on shade of dental porcelain"; Nov. 1985; pp 625–627, vol. 54 No. 5, Journal of Prosthetic Dentistry.

Council on Dental Materials, Instruments, and Equipment; "How to improve shade matching in the dental operatory"; Feb. 1981; pp 209–210, vol. 102; JADA.

(List continued on next page.)

*Primary Examiner*—Frank G. Font
*Assistant Examiner*—Amanda Merlino
(74) *Attorney, Agent, or Firm*—Loudermilk & Associates

(57) ABSTRACT

Optical characteristic measuring systems and methods such as for determining the color or other optical characteristics of an object are disclosed. Perimeter receiver fiber optics are spaced apart from a source fiber optic and receive light from the surface of the object being measured. Light from the perimeter fiber optics pass to a variety of filters. The system utilizes the perimeter receiver fiber optics to determine information regarding the height and angle of the probe with respect to the object being measured. Under processor control, the optical characteristics measurement may be made at a predetermined height and angle. Various color spectral photometer arrangements are disclosed. Translucency, fluorescence, gloss and/or surface texture data also may be obtained. Audio feedback may be provided to guide operator use of the system. The probe may have a removable or shielded tip for contamination prevention. A method of producing prostheses based on measured data also is disclosed. Measured data also may be stored and/or organized as part of a data base. Such methods and implements are desirably utilized for purposes of detecting and preventing counterfeiting or the like.

58 Claims, 29 Drawing Sheets

U.S. PATENT DOCUMENTS

| | | | |
|---|---|---|---|
| 3,507,042 | 4/1970 | Hana . | |
| 3,555,262 | 1/1971 | Shimada | 235/193 |
| 3,743,429 | 7/1973 | Kawai . | |
| 3,748,741 | 7/1973 | Yerkes, Jr. | 32/71 |
| 3,778,541 | 12/1973 | Bowker . | |
| 3,986,777 | 10/1976 | Roll . | |
| 4,054,389 | 10/1977 | Owen | 356/419 |
| 4,115,922 | 9/1978 | Alderman | 32/71 |
| 4,125,329 | 11/1978 | French et al. | 356/405 |
| 4,184,175 | 1/1980 | Mullane, Jr. | 356/237 |
| 4,207,678 | 6/1980 | Jeannette | 433/203 |
| 4,241,738 | 12/1980 | Lübbers | 128/666 |
| 4,278,353 | 7/1981 | Ostermayer et al. | 356/416 |
| 4,290,433 | 9/1981 | Alfano | 128/665 |
| 4,324,546 | 4/1982 | Heitlinger et al. | 433/25 |
| 4,382,784 | 5/1983 | Freller | 433/26 |
| 4,411,626 | 10/1983 | Becker et al. | 433/223 |
| 4,464,054 | 8/1984 | Karras et al. | 356/406 |
| 4,487,206 | 12/1984 | Aagard | 128/667 |
| 4,505,589 | 3/1985 | Ott et al. | 356/402 |
| 4,568,191 | 2/1986 | Barry | 356/446 |
| 4,575,805 | 3/1986 | Moermann et al. . | |
| 4,616,933 | 10/1986 | Leveque et al. | 356/416 |
| 4,654,794 | 3/1987 | O'Brien | 364/413 |
| 4,666,309 | 5/1987 | Barry et al. | 356/446 |
| 4,687,329 | 8/1987 | Schultz | 356/328 |
| 4,773,063 | 9/1988 | Hunsperger et al. | 370/3 |
| 4,798,951 | 1/1989 | Walker | 250/227 |
| 4,823,169 | 4/1989 | Ogura | 356/446 |
| 4,836,674 | 6/1989 | Lequime et al. | 356/319 |
| 4,878,485 | 11/1989 | Adair | 600/125 |
| 4,881,811 | 11/1989 | O'Brien | 356/73 |
| 4,917,500 | 4/1990 | Lugos | 356/406 |
| 4,957,371 | 9/1990 | Pellicori et al. | 356/419 |
| 4,986,671 | 1/1991 | Sun et al. | 374/131 |
| 4,988,206 | 1/1991 | Melleney et al. | 356/446 |
| 5,028,139 | 7/1991 | Kramer et al. . | |
| 5,040,940 | 8/1991 | Kolodziej et al. | 414/764 |
| 5,095,210 * | 3/1992 | Wheatley et al. | 356/71 |
| 5,142,383 * | 8/1992 | Mallik | 356/71 |
| 5,159,199 | 10/1992 | LaBaw | 356/328 |
| 5,164,597 | 11/1992 | Lodder | 356/338 |
| 5,166,755 | 11/1992 | Gat | 356/419 |
| 5,229,841 | 7/1993 | Taranowski et al. | 356/406 |
| 5,245,404 | 9/1993 | Jannson et al. | 356/301 |
| 5,306,144 | 4/1994 | Hibst et al. | 433/29 |
| 5,308,771 | 5/1994 | Zhou et al. | 436/39 |
| 5,329,935 | 7/1994 | Takahashi . | |
| 5,377,669 | 1/1995 | Schultz . | |
| 5,383,020 | 1/1995 | Vieillefosse | 356/326 |
| 5,386,292 | 1/1995 | Massen et al. | 356/376 |
| 5,392,110 | 2/1995 | Yojima et al. | 356/376 |
| 5,401,954 | 3/1995 | Richert | 250/226 |
| 5,401,967 | 3/1995 | Stedman et al. | 250/338.5 |
| 5,404,218 | 4/1995 | Nave et al. | 356/301 |
| 5,410,410 | 4/1995 | Yamazaki et al. | 356/376 |
| 5,410,413 | 4/1995 | Sela | 356/446 |
| 5,428,450 | 6/1995 | Vieillefosse et al. | 356/405 |
| 5,450,193 | 9/1995 | Carlsen et al. | 356/301 |
| 5,450,511 | 9/1995 | Dragone | 385/37 |
| 5,453,838 | 9/1995 | Danielian et al. | 356/371 |
| 5,457,525 | 10/1995 | Ohtsuka et al. | 356/3.06 |
| 5,461,476 | 10/1995 | Fournier | 356/343 |
| 5,467,289 | 11/1995 | Abe et al. | 364/560 |
| 5,469,249 | 11/1995 | Magyar, Jr. et al. | 356/4.07 |
| 5,474,449 | 12/1995 | Loge et al. | 433/29 |
| 5,477,332 | 12/1995 | Stone et al. | 356/371 |
| 5,483,335 | 1/1996 | Tobias | 356/310 |
| 5,497,227 * | 3/1996 | Takeuchi et al. | 356/71 |
| 5,498,157 | 3/1996 | Hall | 433/26 |
| 5,560,355 | 10/1996 | Merchant et al. | 356/41 |
| 5,565,976 | 10/1996 | Fleggen et al. | 250/227.16 |
| 5,575,284 | 11/1996 | Athan et al. | 356/41 |
| 5,583,631 * | 12/1996 | Lazzerini | 356/71 |
| 5,590,251 | 12/1996 | Takagi | 395/131 |
| 5,604,594 | 2/1997 | Juffinger | 356/405 |
| 5,625,459 | 4/1997 | Driver | 356/446 |
| 5,668,633 | 9/1997 | Cheetam et al. | 356/402 |
| 5,671,735 | 9/1997 | MacFarlane et al. | 128/633 |
| 5,690,486 | 11/1997 | Zigelbaum | 433/29 |
| 5,695,949 | 12/1997 | Galen et al. | 435/14 |
| 5,696,751 | 12/1997 | Juffinger | 369/119 |
| 5,745,229 | 4/1998 | Jung et al. | 356/73 |
| 5,757,496 | 5/1998 | Yamazaki | 356/373 |
| 5,759,030 | 6/1998 | Jung et al. | 433/29 |
| 5,766,006 | 6/1998 | Murljacic | 433/26 |
| 5,774,610 | 6/1998 | O'Rourke et al. | 385/52 |
| 5,784,507 | 7/1998 | Holm-Kennedy et al. | 385/31 |
| 5,798,839 | 8/1998 | Berner et al. | 356/402 |
| 5,822,474 | 10/1998 | Hara | 385/24 |
| 5,850,195 | 12/1998 | Berlien, Jr. et al. | 341/137 |
| 5,850,301 | 12/1998 | Mizuochi et al. | 359/124 |
| 5,880,826 | 3/1999 | Jung et al. | 433/29 |
| 5,883,708 | 3/1999 | Jung et al. | 356/371 |
| 5,924,981 | 7/1999 | Rothfritz et al. | 600/306 |
| 5,961,324 | 10/1999 | Lehmann | 433/26 |
| 5,995,235 | 11/1999 | Sui et al. | 356/419 |
| 6,040,902 | 3/2000 | Jung et al. | 356/73 |
| 6,100,988 | 8/2000 | Jung et al. . | |

OTHER PUBLICATIONS

Davison et al.; "Shade selection by color vision–defective dental personnel"; Jan. 1990; pp 97–101 vol. 63 No. 1, Journal of Prosthetic Dentistry.

Demro, James C., R. Hartshome, P.A. Levine, L.M. Woody, "Design of Multispectral, Wedge Filter, Remote–Sensing Instrument incorporating a multi–port, thinned, CCD area array" SPIE vol. 2840 p. 280.

Dickerson; "Trilogy of Creating an Esthetic Smile"; Jul. 1996; pp 1–7, vol. 1, Issue 3; Technical Update–A Publication of Micro Dental Laboratories.

Elerding, George T. John G. Thunen, Loren M. Woody "Wedge Imaging Spectrometer: Application to drug and pollution law enforcement" SPIE vol. 1479 *Surveillance Technologies*, p. 380 (1991).

Goldstein et al.; "Repeatability of a specially designed intraoral colorimeter"; Jun. 1993; pp 616–619, vol. 69 No. 6, Journal of Prosthetic Dentistry.

Goodkind et al.; "A comparison of Chromascan and spectrophotometric color measurement of 100 natural teeth"; Jan. 1985; pp 105–109, vol. 53 No. 1, Journal of Prosthetic Dentistry.

Ishikawa et al.; "Trial Manufacture of Photoelectric Colorimeter Using Optical Fibers"; Nov. 1969; pp 191–197, vol. 10, No. 4, Bull. Tokyo dent. Coll.

Johnston et al.; "The Color Accuracy of the Kubelka–Munk Theory for Various Colorants in Maxillofacial Prosthetic Material"; Sep. 1987; pp 1438–1444, vol. 66, No. 9; J. Dent. Res.

Johnston et al.; "Assessment of Appearance Match by Visual Observation and Clinical Colorimetry"; May 1989; pp 819–822, vol. 68, No. 5; J. Dent. Res.

Kato et al; "The Current State of Porcelain Shades: A Discussion"; Oct. 1984; pp 559–571, vol. 8, No. 9; Quintessence Of Dental Technology.

Mika, Aram M., "Linear–Wedge Spectrometer" SPIE vol. 1298 *Imaging Spectroscopy of the Terrestrial Environment*, p. 127 (1990).

Miller; "Organizing color in dentistry"; Dec. 1987; pp 26E–40E, Special Issue; JADA.

Miller et al; "Shade selection and laboratory communication"; May 1993; pp 305–309, vol. 24, No. 5; Quintessence International.

O'Brien et al.; "Coverage Errors of Two Shade Guides"; Jan./Feb. 1991; pp 45–50, vol. 4, No. 1; The International Journal of Prosthodontics.

O'Brien et al.; "A New, Small–color–difference Equation for Dental Shades"; Nov. 1990; pp 1762–1764, vol. 69, No. 11; J. Dent. Res.

O'Keefe et al.; "Color Shade and Matching: The Weak Link in Esthetic Dentistry"; Feb. 1990; pp 116–120, vol. XI, No. 2, Compend Contin Educ Dent.

Pensler; "A New Appraoch to Shade Selection"; Sep. 1991; pp 668–675, vol. XII, No. 9, Compend Contin Educ Dent.

Preston et al.; "Light and Lighting in the Dental Office"; Jul. 1978; pp 431–451, vol. 22, No. 3; Dental Clinics of North America.

Preston; "Current status of shade selection and color matching"; Jan. 1985; pp 47–58, vol. 16, No. 1; Quintessence International.

Rosenstiel et al.; "The effects of manipulative variables on the color of ceramic metal restorations"; Sep. 1987; pp 297–303, vol. 60 No. 3, Journal of Prosthetic Dentistry.

Rugh et al.; "The Relationship Between Elastomer Opacity, Colorimeter Beam Size, and Measured Colorimetric Response"; Nov./Dec. 1991; pp 569–576, vol. 4, No. 6; The International Journal of Prosthodontics.

Ryther et al.; "Colormetric Evaluation of Shade Guide Variability"; 1993; p. 215; J. Dent. Res. 72 (IADR Abstracts) Special Issue.

Schwabacher et al.; "Three–dimensional color coordinates of natural teeth compared with three shade guides"; Oct. 1990; pp 425–431, vol. 64 No. 4, Journal of Prosthetic Dentistry.

Seghi et al.; "Spectrophotometric analysis of color differences between porcelain systems"; Jul. 1986; pp 35–40, vol. 56 No. 1, Journal of Prosthetic Dentistry.

Seghi et al.; "Visual and Instrument Colorimetric Assessments of Small Color Differences on Translucent Dental Porcelain"; Dec. 1989; pp 1760–1764, vol. 68, No. 12; J. Dent. Res.

Seghi et al.; "Performance Assessment of Colorimetric Devices on Dental Porcelains"; Dec. 1989; pp 1755–1759, vol. 69, No. 11; J. Dent. Res.

Seghi; "Effects of Instrument–measuring Geometry on Colorimetric Assessments of Dental Porcelains"; May. 1990; pp 1180–1183, vol. 69, No. 5; J. Dent. Res.

Sorenson et al.; "Improved color matching of metal–ceramic restorations. Part I: A systematic method for shade determination"; Aug. 1987; pp 133–139, vol. 58, No. 2, Journal of Prosthetic Dentistry.

Sorenson et al.; "Improved color matching of metal–ceramic restorations. Part II: Procedures for visual communication"; Dec. 1987; pp 669–677, vol. 58, No. 6, Journal of Prosthetic Dentistry.

Sproul; "Color matching in dentistry. Part 1. The three–dimensional nature of color"; Apr. 1973; pp 416–424, vol. 29, No. 4; J. Prosthet. Dent.

Sproul; "Color matching in dentistry. Part 1. Color control"; Feb. 1974; pp 146–154, vol. 31, No. 2; J. Prosthet. Dent.

Sproul; "Color matching in dentistry. Part 2. Practical applications of the organization of color"; May 1973; pp 556–566, vol. 29, No. 5; J. Prosthet. Dent.

Swift et al.; "Colormetric Evaluation of Vita Shade Resin Composites"; 1994; pp 356–361, vol. 7, No. 4; The International Journal of Prosthodontics.

van der Burgt et al.; "A comparison of new and conventional methods for quantification of tooth color"; Feb. 1990; pp 155–162, vol. 63 No. 2, Journal of Prosthetic Dentistry.

* cited by examiner

R - LIGHT RECEIVER FIBER OPTICS
S - LIGHT SOURCE FIBER OPTIC

S - LIGHT SOURCE FIBER
R - RED RECEIVER
G - GREEN RECEIVER
B - BLUE RECEIVER
P - NEUTRAL (FULL BAND) RECEIVERS

S - LIGHT SOURCE FIBER
P - NEUTRAL (FULL BAND) RECEIVER
C - COLOR RECEIVER

S - LIGHT SOURCE FIBER
$R_{1X}$ - INNER RING RECEIVER FIBER
$R_{2X}$ - 2nd RING RECEIVER FIBER
$R_{3X}$ - 3rd RING RECEIVER FIBER

METHOD AND APPARATUS FOR DETECTING AND PREVENTING COUNTERFEITING

This application is a continuation of 09/360,529 filed Jul. 26, 1999, now U.S. Pat. No. 6,038,016 issued Mar. 14, 2000 which is a continuation of 08/886,566 filed Jul. 1, 1999, now U.S. Pat. No. 5,966,205 issued Oct. 12, 1999.

FIELD OF THE INVENTION

The present invention relates to devices and methods for measuring optical characteristics such as color spectrums, translucence, gloss, and other characteristics of objects, and more particularly to devices and methods for measuring the color and other optical characteristics of objects or surfaces with a probe that presents minimal problems with height or angular dependencies and that may be applied to detecting and preventing counterfeiting.

BACKGROUND OF THE INVENTION

The present invention pertains to methods and devices for detecting and preventing counterfeiting and the like based on measurements of various optical characteristics or properties of objects and materials.

Various color/optical measuring devices such as spectrophotometers and colorimeters are known in the art. To understand the limitations of such conventional devices, it is helpful to understand certain principles relating to color. Without being bound by theory, Applicants provide the following discussion.

The color of an object determines the manner in which light, is reflected from the object. When light is incident upon an object, the reflected light will vary in intensity and wavelength dependent upon the color of the object. Thus, a red object will reflect red light with a greater intensity than a blue or a green object, and correspondingly a green object will reflect green light with a greater intensity than a red or blue object.

The optical properties of an object are also affected by the manner in which light is reflected from the surface. Glossy objects, those that reflect light specularly such as mirrors or other highly polished surfaces, reflect light differently than diffuse objects or those that reflect light in all directions, such as the reflection from a rough or otherwise non-polished surface. Although both objects may have the same color and exhibit the same reflectance or absorption optical spectral responses, their appearances differ because of the manner in which they reject light.

Additionally, many objects may be translucent or have semi-translucent surfaces or thin layers covering their surfaces. For example, some materials have a complicated structure consisting of an outer layer and an inner layer. The outer layer is semitranslucent. The inner layers are also translucent to a greater or lesser degree. Such materials and objects also appear different from objects that are opaque, even though they may be the same color because of the manner in which they can propagate light in the translucent layer and emit the light ray displaced from its point of entry.

One method of quantifying the color of an object is to illuminate it with broad band spectrum or "white" light, and measure the spectral properties of the reflected light over the entire visible spectrum and compare the reflected spectrum with the incident light spectrum. Such instruments typically require a broad band spectrophotometer, which generally are expensive, bulky and relatively cumbersome to operate, thereby limiting the practical application of such instruments.

For certain applications, the broad band data provided by a spectrophotometer is unnecessary. For such applications, devices have been produced or proposed that quantify color in terms of a numerical value or relatively small set of values representative of the color of the object.

It is known that the color of an object can be represented by three values. For example, the color of an object can be represented by red, green and blue values, an intensity value and color difference values, by a CIE value, or by what are known as "tristimulus values" or numerous other orthogonal combinations. For most tristimulus systems, the three values are orthogonal; i.e. any combination of two elements in the set cannot be included in the third element.

One such method of quantifying the color of an object is to illuminate an object with broad band "white" light and measure the intensity of the reflected light after it has been passed through narrow band filters. Typically three filters (such as red, green and blue) are used to provide tristimulus light values representative of the color of the surface. Yet another method is to illuminate an object with three monochromatic light sources or narrow band light sources (such as red, green and blue) one at a time and then measure the intensity of the reflected light with a single light sensor. The three measurements are then converted to a tristimulus value representative of the color of the surface. Such color measurement techniques can be utilized to produce equivalent tristimulus values representative of the color of the surface. Generally, it does not matter if a "white" light source is used with a plurality of color sensors (or a continuum in the case of a spectrophotometer), or if a plurality of colored light sources are utilized with a single light sensor.

There are, however, difficulties with the conventional techniques. When light is incident upon a surface and reflected to a light receiver, the height of the light sensor and the angle of the sensor relative to the surface and to the light source also affect the intensity of the received light. Since the color determination is being made by measuring and quantifying the intensity of the received light for different colors, it is important that the height and angular dependency of the light receiver be eliminated or accounted for in some manner.

One method for eliminating the height and angular dependency of the light source and receiver is to provide a fixed mounting arrangement where the light source and receiver are stationary and the object is always positioned and measured at a preset height and angle. The fixed mounting arrangement greatly limits the applicability of such a method. Another method is to add mounting feet to the light source and receiver probe and to touch the object with the probe to maintain a constant height and angle. The feet in such an apparatus must be wide enough apart to insure that a constant angle (usually perpendicular) is maintained relative to the object. Such an apparatus tends to be very difficult to utilize on small objects or on objects that are hard to reach, and in general does not work satisfactorily in measuring objects with curved surfaces.

The use of color measuring devices in the field of dentistry has been proposed. In modern dentistry, the color of teeth typically are quantified by manually comparing a patient's teeth with a set of "shade guides." There are numerous shade guides available for dentists in order to properly select the desired color of dental prosthesis. Such shade guides have been utilized for decades and the color determination is made subjectively by the dentist by holding a set of shade guides next to a patient's teeth and attempting to find the best match. Unfortunately, however, the best match often is affected by the ambient light color in the dental operatory and the surrounding color of the patient's makeup or clothing and by the fatigue level of the dentist Similar subjective color quantification also is made in the paint industry by comparing the color of an object with a paint reference guide. There are numerous paint guides available in the industry and the color determination also often is affected by ambient light color, user fatigue and the color sensitivity of the user. Many individuals are color insensitive (color blind) to certain colors, further complicating color determination.

In general, color quantification is needed in many industries. Several, but certainly not all, applications include: dentistry (color of teeth); dermatology (color of skin lesions); interior decorating (color of paint, fabrics); the textile industry: automotive repair (matching paint colors); photography (color of reproductions, color reference of photographs to the object being photographed); printing and lithography; cosmetics (hair and skin color, makeup matching); and other applications in which it useful to measure color in an expedient and reliable manner.

With respect to such applications, however, the limitations of conventional color/optical measuring techniques typically restrict the utility of such techniques. For example, the high cost and bulkiness of typical broad band spectrometers, and the fixed mounting arrangements or feet required to address the height and angular dependency, often limit the applicability of such conventional techniques.

Moreover, another limitation of such conventional methods and devices are that the resolution of the height and angular dependency problems typically require contact with the object being measured. In certain applications, it may be desirable to measure and quantify the color of an object with a small probe that does not require contact with the surface of the object. In certain applications, for example, hygienic considerations make such contact undesirable. In the other applications such as interior decorating, contact with the object can mar the surface such as if the object is coated with wet paint) or otherwise cause undesirable effects.

In summary, there is a need for a low cost, hand-held probe of small size that can reliably measure and quantify the color and other optical characteristics of an object Without requiring physical contact with the object, and also a need for methods based on such a device in the field of dentistry and other applications.

SUMMARY OF THE INVENTION

In accordance with the present invention, devices and methods are provided for measuring the color and other optical characteristics of objects, reliably and with minimal problems of height and angular dependence, and which may be desirably applied to detecting or preventing counterfeiting or the like. A handheld probe is utilized in the present invention, with the handheld probe containing a number of fiber optics in certain preferred embodiments. Light is directed from one (or more) light source(s) towards the object to be measured, which in certain preferred embodiments is a central light source fiber optic (other light sources and light source arrangements also may be utilized). Light reflected from the object is detected by a number of light receivers. Included in the light receivers (which may be light receiver fiber optics) are a plurality of perimeter and/or broadband or other receivers (which may be receiver fiber optics, etc.). In certain preferred embodiments, a number of groups of perimeter fiber optics are utilized in order to take measurements at a desired, and predetermined height and angle, thereby minimizing height and angular dependency problems found in conventional methods, and to quantify other optical characteristics such as gloss. In certain embodiments, the present invention also may measure gloss, translucence, and fluorescence characteristics of the object being measured, as well as surface texture and/or other optical or surface characteristics. In certain embodiments, the present invention may distinguish the surface spectral reflectance response and also a bulk spectral response.

The present invention may include constituent elements of a broad band spectrophotometer, or, alternatively, may include constituent elements of a tristimulus type calorimeter. The present invention may employ a variety of color measuring devices in order to measure color and other optical characteristics in a practical, reliable and efficient manner, and in certain preferred embodiments includes a color filter array and a plurality of color sensors. A microprocessor is included for control and calculation purposes. A temperature sensor is included to measure temperature in order to detect abnormal conditions and/or to compensate for temperature effects of the filters or other components of the system. In addition, the present invention may include audio feedback to guide the operator in making color/optical measurements, as well as one or more display devices for displaying control, status or other information.

With the present invention, color/optical measurements may be made with a handheld probe in a practical and reliable manner, essentially free of height and angular dependency problems, without resorting to fixtures, feet or other undesirable mechanical arrangements for fixing the height and angle of the probe with respect to the object.

Accordingly, it is an object of the present invention to address limitations of conventional color/optical measuring techniques.

It is another object of the present invention to provide a method and device useful in measuring the color or other optical characteristics of teeth, fabric or other objects or surfaces with a hand-held probe of practical size that may advantageously utilize, but does not necessarily require, contact with the object or surface.

It is a further object of the present invention to provide a color/optical measurement probe and method that does not require fixed position mechanical mounting, feet or other mechanical impediments.

It is yet another object of the present invention to provide a probe and method useful for measuring color and/or other optical characteristics ,hat may be utilized with a probe simply placed near the surface to be measured.

It is a still further object of the present invention to provide a probe and method that are capable of determining translucency characteristics of the object being measured.

It is still further object of the present invention to provide a probe and method that are capable of determining translucency characteristics of the object being measured by making measurements from one side of the object.

It is a further object of the present invention to provide a probe and method that are capable of determining surface texture characteristics of the object being measured.

It is a still further object of the present invention to provide a probe and method that are capable of determining fluorescence characteristics of the object being measured.

It is yet a further object of the present invention to provide a probe and method that are capable of determining gloss (or degree of specular reflectance) characteristics of the object being measured.

It is another object of the present invention to provide a probe and method that can measure the area of a small spot singularly, or that also can measure irregular shapes by moving the probe over an area and integrating the color of the entire area.

It is a further object of the present invention to provide a method of measuring the color of an object and preparing prostheses, colored fillings, or other materials or taking other action.

It is yet another object of the present invention to provide a method and apparatus that minimizes contamination problems, while providing a reliable and expedient manner in which to measure an object and prepare coatings, layers, prostheses, colored fillings, or other materials.

It is an object of the present invention to provide methods of using measured data to implement processes for forming objects, prostheses and the like, as well as methods for keeping such measurement and/or other data as part of a record database.

It also is an object of the present invention to provide probes and methods for measuring optical characteristics with a probe that is held substantially stationary with respect to the object being measured.

It is an object of the present invention to provide probes and methods for measuring optical characteristics with a probe that may have a removable tip or shield that may be removed for cleaning, disposed after use or the like.

Finally, and in particular, it is an object of the present invention to provide probes, equipment and methods for detecting and preventing counterfeiting or the like by way of measuring or assessing surface or subsurface optical characteristics or features.

BRIEF DESCRIPTION OF THE DRAWINGS

The present invention may be more fully understood by a description of certain preferred embodiments in conjunction with the attached drawings in which:

FIGS. 30A to 30C illustrate materials or object portions for purposes of explaining preferred embodiments of methods and devices for detecting or preventing counterfeiting or the like.

DETAILED DESCRIPTION OF THE PREFERRED EMBODIMENTS

The present invention will be described in greater detail with reference to certain preferred embodiments and certain other embodiments, which may serve to further the understanding of preferred embodiments of the present invention. As described elsewhere herein, various refinements and substitutions of the various embodiments are possible based on the principles and teachings herein. It should be noted that methods and implements will be described initially that man have wider utility than preventing/detecting counterfeiting, and preferred embodiments relating to preventing/detecting counterfeiting will be described thereafter.

Figure 1:
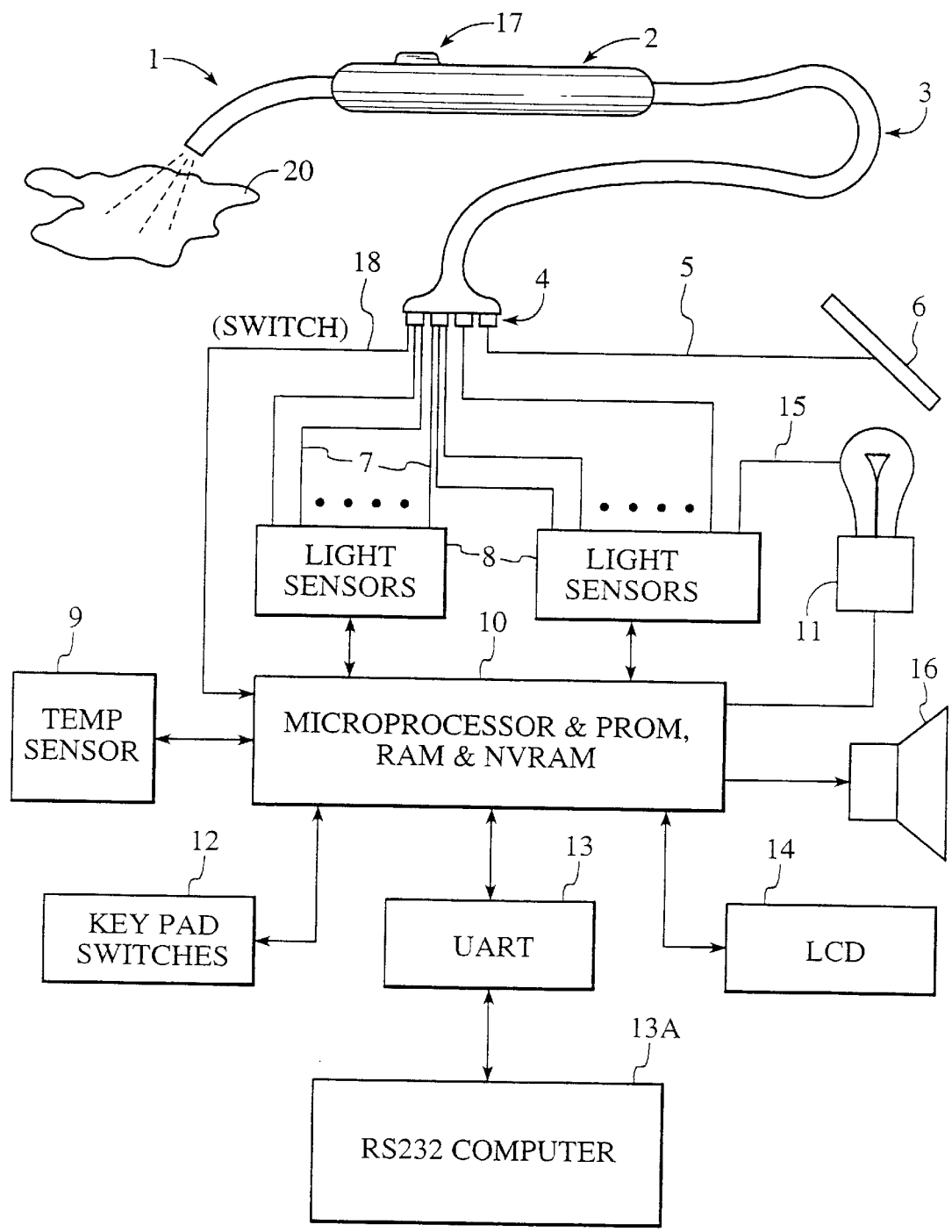
FIG. 1 is a diagram illustrating a preferred embodiment of the present invention.

With reference to FIG. 1, an exemplary preferred embodiment of a color/optical characteristic measuring system and method in accordance with the present invention will be described.

Probe tip 1 encloses a plurality of fiber optics, each of which may constitute one or more fiber optic fibers. In a preferred embodiment, the fiber optics contained within probe tip 1 includes a single light source fiber optic and a number of groups of light receiver fiber optics. The use of such fiber optics to measure the color or other optical characteristics of an object will be described later herein. Probe tip 1 is attached to probe body 2, on which is fixed switch 17. Switch 17 communicates with microprocessor 10 through wire IS and provides, for example, a mechanism by which an operator may activate the device in order to make a color/optical measurement. Fiber optics within probe tip 1 terminate at the forward end thereof (i.e., the end away from probe body 2). The forward end of probe tip 1 is directed towards the surface of the object to be measured as described more fully below. The fiber optics within probe tip 1 optically extend through probe body 2 and through fiber optic cable 3 to light sensors 8, which are coupled to microprocessor 10.

It should be noted that microprocessor 10 includes conventional associated components, such as memory (programmable memory, such as PRONM, EPROM or EEPROM; working memory such as DRANs or SRAMs; and/or other types of memory such as non-volatile memory, such as FLASH). peripheral circuits, clocks and power supplies, although for clarity such components are not explicitly shown. Other types of computing devices (such as other microprocessor systems, programmable logic arrays or the like) are used in other embodiments of the present invention.

In the embodiment of FIG. 1, the fiber optics from fiber optic cable 3 end at splicing connector 4. From splicing connector 4, each or some of the receiver fiber optics used in this embodiment is/are spliced into a number of smaller fiber optics (generally denoted as fibers 7), which in this embodiment are fibers of equal diameter, but which in other preferred embodiments may be of unequal diameter and/or numeric aperture (NA) (including, for example, larger or smaller "height/angle" or perimeter fibers, as more fully described herein). One or the fibers of each group of fibers may pass to light sensors 8 through a neutral density filter (as more fully described with reference to FIG. 3), and collectively such neutrally filtered fibers may be utilized for purposes of height/angle determination, translucency determination, and gloss determination (and also may be utilized to measure other surface characteristics, as more fully described herein). Remaining fibers of each group of fibers may pass to light sensors 8 through color filters and may be used to make color/optical measurements. In still other embodiments, splicing connector 4 is not used, and fiber bundles of, for example, five or more fibers each extend from light sensors 8 to the forward end of probe tip 1. In certain embodiments, unused fibers or other materials may be included as part of a bundle of fibers for purposes of, for example, easing the manufacturing process for the fiber bundle. What should be noted is that, for purposes of the present invention, a plurality of light receiver fiber optics or elements (such as fibers 7) are presented to light sensors 8, with the light from the light receiver fiber optics/elements representing light reflected from object 20. While the various embodiments described herein present tradeoffs and benefits that may not have been apparent prior to the present invention (land thus may be independently novel), what is important for the present discussion is that light from fiber optics/elements at the forward end of probe tip 1 is presented to sensors S for color/optical measurements and angle/height determination. etc. In particular, fiber optic configurations of certain preferred embodiments will be explained in more detail hereinafter.

Light source 11 in the preferred embodiment is a halogen light source (of, for example, 5–100 watts, with the particular wattage chosen for the particular application), which may be under the control of microprocessor 10. The light from light source 11 reflects from cold mirror 6 and into source fiber optic 5. Source fiber optic 5 passes through to the forward end of probe tip 1 and provides the light stimulus used for purposes of making the measurements described herein. Cold mirror 6 reflects visible light and passes infra-red light, and is used to reduce the amount of infra-red light produced by light source 11 before the light is introduced into source fiber optic 5. Such infra-red light reduction of the light from a halogen source such as light source 11 can help prevent saturation of the receiving light sensors, which can reduce overall system sensitivity. Fiber 15 receives light directly from light source 11 and passes through to light sensors 8 (which may be through a neutral density filter). Microprocessor 10 monitors the light output of light source 11 through fiber 15, and thus may monitor and, if necessary compensate for, drift of the output of light source 11. In certain embodiments, microprocessor 10 also may sound an alarm (such as through speaker 16) or otherwise provide some indication if abnormal or other undesired performance of light source 11 is detected.

The data output from light sensors 8 pass to microprocessor 10. Microprocessor 10 processes the data from light sensors 8 to produce a measurement of color and/or other characteristics. Microprocessor 10 also is coupled to key pad switches 12, which serve as an input device. Through key pad switches 12, the operator may input control information or commands, or information relating to the object being measured or the like. In general, key; pad switches 12, or other suitable data input devices (such as push button, toggle, membrane or other switches or the like), serve as a mechanism to input desired information to microprocessor 10.

Microprocessor 10 also communicates with UART 13, which enables microprocessor 10 to be coupled to an external device such as computer 13A. In such embodiments, data provided by microprocessor 10 may be processed as desired for the particular application, such as for averaging, format conversion or for various display or print options. etc. In the preferred embodiment. UART 13 is configured so as to provide what is known as a RS232 interface, such as is commonly found in personal computers.

Microprocessor 10 also communicates with LCD 14 for purposes of displaying status, control or other information as desired for the particular application. For example, color bars, charts or other graphic representations of the color or other collected data and/or the measured object may be displayed. In other embodiments, other display devices are used, such as CRTs, matrix-type LEDs, lights or other mechanisms for producing a visible indicia of system status or the like. Upon system initialization, for example, LCD 14 may provide an indication that he system is stable, ready and available for taking color measurements.

Also coupled to microprocessor 10 is speaker 16. Speaker 16, in a preferred embodiment as discussed more fully below, serves to provide audio feedback to the operator, which may serve to guide the operator in the use of the device. Speaker 16 also may serve to provide status or other information alerting the operator of the condition of the system, including an audio tone, beeps or other audible indication (i.e., voice) that the system is initialized and available for taking measurements. Speaker 16 also may present audio information indicative of the measured data, shade guide or reference values corresponding to the measured data, or an indication of the status of the color/optical measurements.

Microprocessor 10 also receives an input from temperature sensor 9. Given that many types of filters (and perhaps light sources or other components) may operate reliably only in a given temperature range, temperature sensor 9 serves to provide temperature information to microprocessor 10. In particular, color filters, such as may be included in light sensors 8, may be sensitive to temperature, and may operate reliably only over a certain temperature range. In certain embodiments, if the temperature is within a usable range, microprocessor 10 may compensate for temperature variations of the color filters. In such embodiments, the color filters are characterized as to filtering characteristics as a function of temperature, either by data provided by the filter manufacturer, or through measurement as a function of temperature. Such filter temperature compensation data may be stored in the form of a look-up table in memory, or may be stored as a set of polynomial coefficients from which the temperature characteristics of the filters may be computed by microprocessor 10.

In general, under control of microprocessor 10, which may be in response to operator activation (through, for example, key pad switches 12 or switch 17), light is directed from light source 11, and reflected from cold mirror 6 through source fiber optic 5 (and through fiber optic cable 3, probe body 2 and probe tip 1, or through some other suitable light source element) and is directed onto object 20. Light reflected from object 20 passes through the receiver fiber optics/elements in probe tip 1 to light sensors 8 (through probe body 2, fiber optic cable 3 and fibers 7). Based on the information produced by light sensors S, microprocessor 10 produces a color/optical measurement result or other information to the operator. Color measurement or other data produced by microprocessor 10 may be displayed on display 14, passed through UART 13 to computer 13A, or used to generate audio information that is presented to speaker 16. Other operational aspects of the preferred embodiment illustrated in FIG. 1 will be explained hereinafter.

Figure 2:
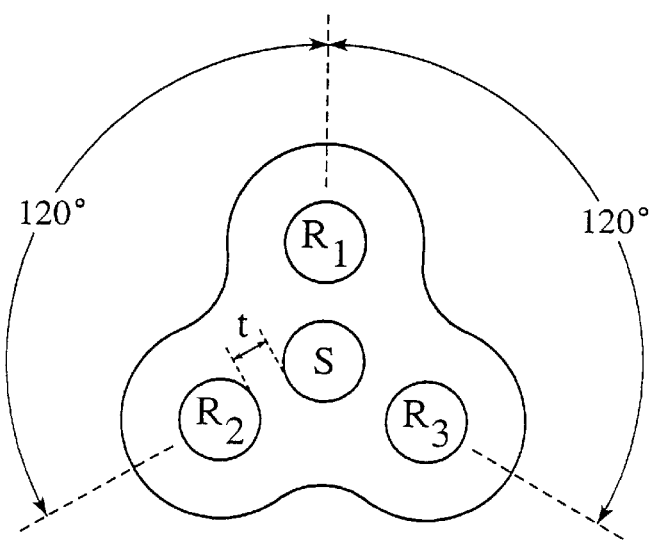
FIG. 2 is a diagram illustrating a cross section of a probe that may be used in accordance with a certain embodiments of the present invention.

With reference to FIG. 2 an embodiment of a fiber optic arrangement presented at the forward end of probe tip 1 will now be described, which may serve to further the understanding of preferred embodiments of the present invention. As illustrated in FIG. 2, this embodiment utilizes a single central light source fiber optic, denoted as light source fiber optic S, and a plurality of perimeter light receiver fiber optics, denoted as light receivers R1, R2 and R3. As is illustrated, this embodiment utilizes three perimeter fiber optics, although in other embodiments two, four or some other number of receiver fiber optics are utilized. As more fully described herein, the perimeter light receiver fiber optics serve not only to provide reflected light for purposes of making the color/optical measurement, but such perimeter fibers also serve to provide information regarding the angle and height of probe tip 1 with respect to the surface of the object that is being measured, and also may provide information regarding the surface characteristics of the object that is being measured.

In the illustrated embodiment, receiver fiber optics R1 to R3 are positioned symmetrically around source fiber optic S, with a spacing of about 120 degrees from each other. It should be noted that spacing t is provided between receiver fiber optics R1 to R3 and source fiber optic S. While the precise angular placement of the receiver fiber optics around the perimeter of the fiber bundle in general is not critical, it has been determined that three receiver fiber optics positioned 120 degrees apart generally may give acceptable results. As discussed above, in certain embodiments light receiver fiber optics R1 to R3 each constitute a single fiber, which is divided at splicing connector 4 (refer again to FIG. 1), or, in alternate embodiments, light receiver fiber optics R1 to R3 each constitute a bundle of fibers, numbering, for example, at least five fibers per bundle. It has been determined that, with available fibers of uniform size, a bundle of, for example, seven fibers may be readily produced (although as will be apparent to one of skill in the art, the precise number of fibers may be determined in view of the desired number of receiver fiber optics, manufacturing considerations, etc.). The use of light receiver fiber optics R1 to R3 to produce color/optical measurements is further described elsewhere herein, although it may be noted here that receiver fiber optics R1 to R3 may serve to detect whether, for example, the angle of probe tip 1 with respect to the surface of the object being measured is at 90 degrees, or if the surface of the object being measured contains surface texture and/or spectral irregularities. In the case where probe tip 1 is perpendicular to the surface of the object being measured and the surface of the object being measured is a diffuse reflector (i.e., a matte-type reflector, as compared to a glossy, spectral, or shiny-type reflector which may have "hot spots"), then the light intensity input into the perimeter fibers should be approximately equal. It also should be noted that spacing t serves to adjust the optimal height at which color/optical measurements should be made (as more fully described below). Preferred embodiments, as described hereinafter, may enable the quantification of the gloss or degree of spectral reflection of the object being measured.

In one particular aspect useful with embodiments of the present invention, area between the fiber optics on probe tip 1 may be wholly or partially filled with a non-reflective material and/or surface (which may be a black mat, contoured or other non-reflective surface). Having such exposed area of probe tip 1 non-reflective helps to reduce undesired reflections, thereby helping to increase the accuracy and reliability.

Figure 3:
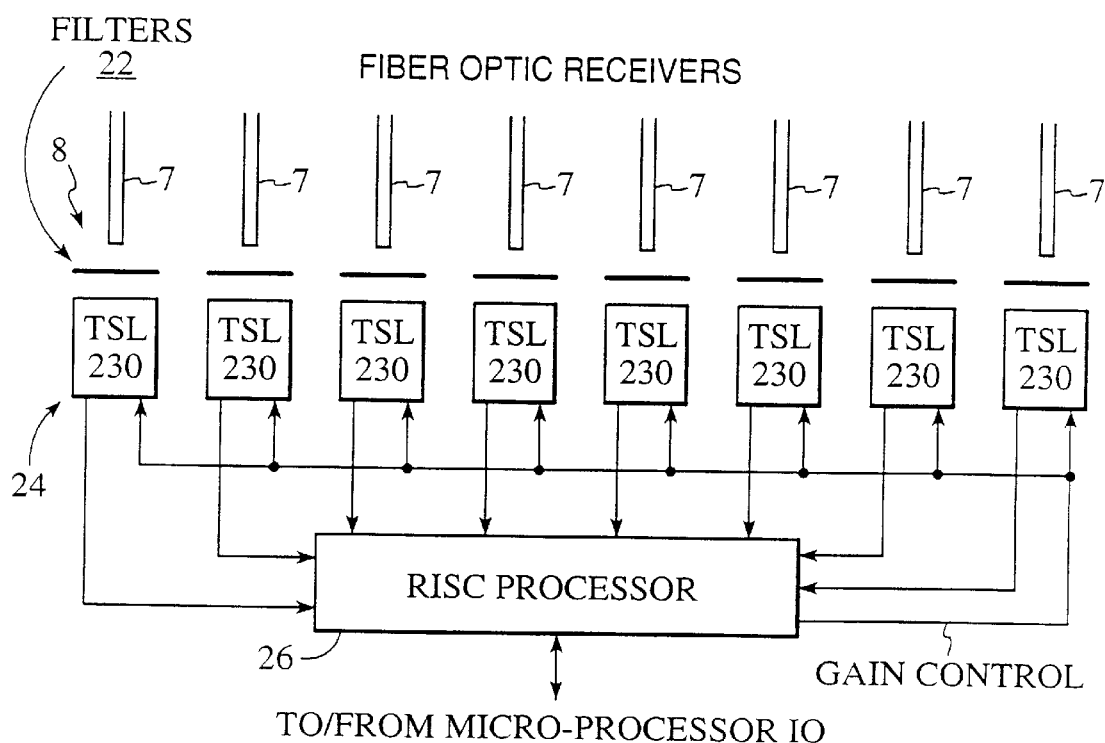
FIG. 3 is a diagram illustrating an illustrative arrangement of fiber optic receivers and sensors utilized with a certain embodiments.

With reference to FIG. 3, a partial arrangement of light receiver fiber optics and sensors that may be used in a preferred embodiment of the present invention will now be described. Fibers 7 represent light receiving fiber optics, which transmit light reflected from the object being measured to light sensors 8. In an exemplary embodiment, sixteen sensors (two sets of eight) are utilized, although for ease of discussion only 3 are illustrated in FIG. 3 (in this preferred embodiment, the circuitry of FIG. 3 is duplicated, for example, in order to result in sixteen sensors). In other embodiments, other numbers of sensors are utilized in accordance with the present invention.

Light from fibers 7 is presented to sensors 8, which in a preferred embodiment pass through filters 22 to sensing elements 24. In this preferred embodiment, sensing elements 24 include light-to-frequency converters, manufactured by Texas Instruments and sold under the part number TSL230. Such converters constitute, in general, photo diode arrays hat integrate the light received from fibers 7 and output an AC signal with a frequency proportional to the intensity (not frequency) of the incident light. Without being bound by theory, the basic principle of such devices is that, as the intensity increases, the integrator output voltage rises more quickly, and the shorter the integrator rise time, the greater the output frequency. The outputs of the TSL230 sensors are TTL compatible digital signals, which may be coupled to various digital logic devices.

The outputs of sensing elements 24 are, in this embodiment, asynchronous signals of frequencies depending upon the light intensity presented to the particular sensing elements, which are presented to processor 26. In a preferred embodiment, processor 26 is a Microchip PIC16C55 or PIC16C57 microprocessor, which as described more fully herein implements an algorithm to measure the frequencies of the signals output by sensing elements 24. In other embodiments, a more integrated microprocessor/microcontroller, such as Hitachi's SH RISC microcontrollers, is utilized to provide further system integration or the like.

As previously described, processor 26 measures the frequencies of the signals output from sensing elements 24. In a preferred embodiment, processor 26 implements a software timing loop, and at periodic intervals processor 26 reads the states of the outputs of sensing elements 24. An internal counter is incremented each pass through the software timing loop. The accuracy of the timing loop generally is determined by the crystal oscillator time base (not shown in FIG. 3) coupled to processor 26 (such oscillators typically are quite sable). After reading the outputs of sensing elements 24, processor 2–6 performs an exclusive OR ("XOR") operation with the last data read (in a preferred embodiment such data is read in byte length). If any bit has changed, the XOR operation will produce a 1, and, if no bits have changed, the XOR operation will produce a 0. If the result is non-zero, the input byte is saved along with the value of the internal counter (that is incremented each pass through the software timing loop). If the result is zero, the systems waits (e.g., executes no operation instructions) the same amount of time as if the data had to be saved, and the looping operation continues. The process continues until all eight inputs have changed at least twice, which enables measurement of a full ½ period of each input. Upon conclusion of the looping process, processor 26 analyzes he stored input bytes and internal counter states. There should be 2 to 16 saved inputs (for the 8 total sensors of FIG. 3) and counter states (if two or more inputs change at the same time, they are saved simultaneously). As will be understood by one of skill in the art, the stored values of the internal counter contains information determinative of the period of the signals received from sensing elements 24. By proper subtraction of internal counter values at times when an, input bit has changed, the period may be calculated. Such periods calculated for each of outputs of sensing elements is provided by processor 26 to microprocessor 10 (see, e.g., FIG. 1). From such calculated periods, a measure of the received light intensities may be calculated. In alternate embodiments, the frequency of the outputs of the TSL300 sensors is measured directly by a similar software loop as the one described above. The outputs are monitored by the RISC processor in a software timing loop and are XORed with the previous input as described above. If a transition occurs for a particular TSL230 input, a counter register for the particular TSL230 input is incremented. The software loop is executed for a pre-determined period of time and the frequency of the input is calculated by dividing the number of transitions by the pre-determined time and scaling the result. It will also be apparent to one skilled in the art that more sophisticated measurement schemes can also be implemented whereby both the frequency and period are simultaneously measured by high speed RISC processors such as those of the Hitachi SH family.

It should be noted that the sensing circuitry and methodology illustrated in FIG. 3 have been determined to provide a practical and expedient manner in which to measure the light intensities received by sensing elements 24. In other embodiments, other circuits and methodologies are employed (such other exemplary sensing schemes are described elsewhere herein).

As discussed above with reference to FIG. 1, one or more of fibers 7 measures light source 11, which may be through a neutral density filter, which serves to reduce the intensity of the received light in order to maintain the intensity roughly in the range of the other received light intensities. A number of fibers 7 also are from perimeter receiver fiber optics R1 to R3 (see, e.g., FIG. 2) and also may pass through neutral density filters. Such receiving fibers 7 serve to provide data from which angle/height information and/or surface characteristics may be determined.

The remaining twelve fibers (of the illustrated embodiment's total of 16 fibers) of fibers 7 pass through color filters and are used to produce the color measurement. In an embodiment, the color filters are Kodak Sharp Cutting Wratten Gelatin Filters, which pass light with wavelengths greater than the cut-off value of the filter (i.e., redish values), and absorb light with wavelengths less than the cut-off value of the filter (i.e., bluish values). "Sharp Cutting" filters are available in a wide variety of cut-off frequencies/wavelengths, and the cut-off values generally may be selected by proper selection of the desired cut-off filter. In an embodiment, the filter cut-off values are chosen to cover the entire visible spectrum and, in general, to have band spacings of approximately the visible band range (or other desired range) divided by the number of receivers/filters. As an example, 700 nanometers minus 400 nanometers, divided by 11 bands (produced by twelve color receivers/sensors), is roughly 30 nanometer band spacing.

With an array of cut-off filters as described above, and without being bound by theory or the specific embodiments described herein, the received optical spectrum may be measured/calculated by subtracting the light intensities of "adjacent" color receivers. For example, band 1 (400 nm to 430 nm)=(intensity of receiver 12) minus (intensity of receiver 11), and so on for the remaining bands. Such an array of cut-off filters, and the intensity values that may result from filtering with such an array, are more fully described in connection with FIGS. 13A to 14B.

It should be noted here that in alternate embodiments other color filter arrangements are utilized. For example, "notch" or bandpass filters may be utilized, such as may be developed using Schott glass-type filters (whether constructed from separate longpass/shortpass filters or otherwise) or notch interference filters such as those manufactured by Corion, etc.

In a preferred embodiment of the present invention, the specific characteristics of the light source, filters, sensors and fiber optics, etc., are normalized/calibrated by directing the probe towards, and measuring, a known color standard. Such normalization/calibration may be performed by placing the probe in a suitable fixture, with the probe directed from a predetermined position (i.e., height and angle) from the known color standard. Such measured normalization/calibration data may be stored, for example, in a look-up table, and used by microprocessor 10 to normalize or correct measured color or other data. Such procedures may be conducted at start-up, at regular periodic intervals, or by operator command. etc. In particular embodiments, a large number of measurements may be taken on materials of particular characteristics and processed and/or statistically analyzed or the like, with data representing or derived from such measurements stored in memory (such as a look-up table or polynomial or other coefficients, etc.). Thereafter, based upon measurements of an object taken in accordance with the present invention, comparisons may be made with the stored data and assessments of the measured object made or predicted. In one illustrative example, an assessment or prediction may be made of whether the object is wet or dry (having water or other liquid on its surface, wet paint, etc.) based on measurements in accordance with the present invention. In yet another illustrative example, an assessment or prediction of the characteristics of an underlying material, such as tissue before the surface of a tooth, skin, or other material. Such capabilities may be further enhanced by comparisons with measurements taken of the object at an earlier time, such as data taken of the object at one or more earlier points in time. Such comparisons based on such historical data and/or stored data may allow highly useful assessments or predictions of the current or projected condition or status of the tooth, tissue, or other object. etc. Many other industrial uses of such surface and subsurface assessment/prediction capabilities are possible.

What should be noted from the above description is that the receiving and sensing fiber optics and circuitry illustrated in FIG. 3 provide a practical and expedient way to determine the color and other optical or other characteristics by measuring the intensity of the light reflected from the surface of the object being measured.

It also should be noted that such a system measures the spectral band of the reflected light from the object, and once measured such spectral data may be utilized in a variety of ways. For example, such spectral data may be displayed directly as intensity-wavelength band values. In addition, tristimulus type values may be readily computed (through, for example, conventional matrix math), as may any other desired color values. In one particular embodiment useful in dental applications (such as for dental prostheses), the color data is output in the form of a closest match or matches of dental shade guide value(s). In a preferred embodiment, various existing shade guides (such as the shade guides produced by Vita Zahnfabrik) are characterized and stored in a look-up table, or in the graphics art industry Pantone color references, and the color measurement data are used to select the closest shade guide value or values, which may be accompanied by a confidence level or other suitable factor indicating the degree of closeness of the match or matches, including, for example, what are known as ΔE values or ranges of ΔE values, or criteria based on standard deviations, such as standard deviation minimization. In still other embodiments, the color measurement data are used (such as with look-up tables) to select materials for the composition of paint or ceramics such as for prosthetic teeth. There are many other uses of such spectral data measured in accordance with the present invention.

It is Known that certain objects such as human teeth may fluoresce, and such optical characteristics also may be measured in accordance with the present invention. A light source with an ultraviolet component may be used to produce more accurate color/optical data with respect to such objects. Such data may be utilized to adjust the amounts and or proportions or types of fluorescing materials in layers, coatings, restorations or prosthesis, etc. In certain embodiments, a tungsten/halogen source (such as used in a preferred embodiment) may be combined with a UV light source (such as a mercury vapor, xenon or other fluorescent light source, etc.) to produce a light output capable of causing the object to fluoresce. Alternately, a separate UV light source, combined with a visible-light-blocking filter, may be used to illuminate the object. Such a UV light source may be combined with light from a red LED (for example) in order to provide a visual indication of when the UV light is on and also to serve as an aid for the directional positioning of the probe operating with such a light source. A second measurement may be taken using the UV light source in a manner analogous to that described earlier, with the band of the red LED or other supplemental light source being ignored. The second measurement may thus be used to produce an indication of the fluorescence of the object being measured. With such a UV light source, a silica fiber optic (or other suitable material) typically would be required to transmit the light to the object (standard fiber optic materials such as glass and plastic in general do not propagate UV light in a desired manner. etc.).

As described earlier, in certain preferred embodiments the present invention utilizes a plurality of perimeter receiver fiber optics spaced apart from and around a central source fiber optic to measure color and determine information regarding the height and angle of the probe with respect to the surface of the object being measured, which may include other surface characteristic information, etc. Without being bound by theory, certain principles underlying certain aspects of the present invention will now be described with reference to FIGS. 4A to 4C.

Figure 4A:
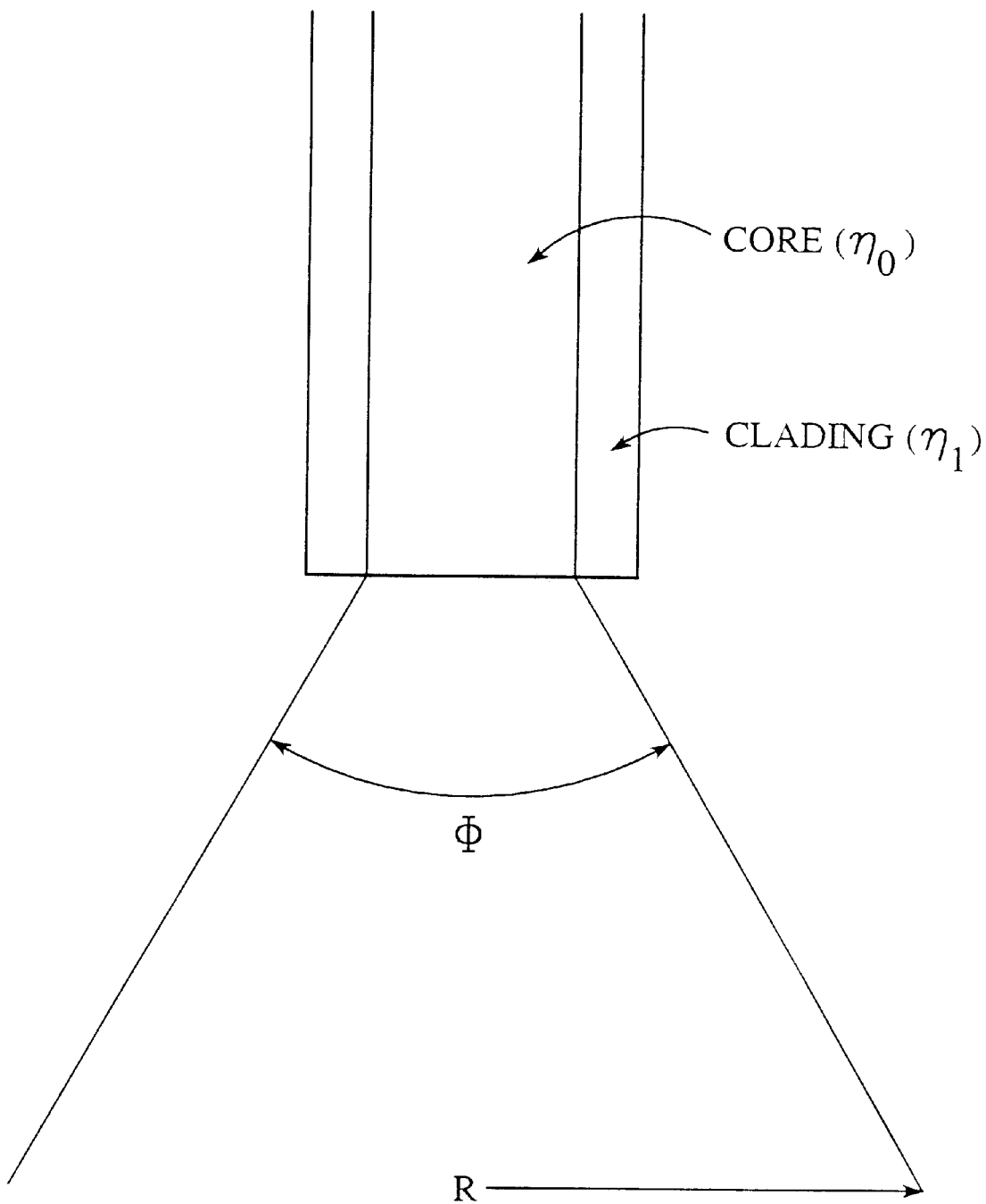
FIGS. 4A to 4C illustrate certain geometric considerations of fiber optics.

FIG. 4A illustrates a typical step index fiber optic consisting of a core and a cladding. For this discussion, it is assumed that the core has an index of refraction of $n_0$ and a cladding has an index of refraction of $n_1$. Although the following discussion is directed to "step index" fibers, it will be appreciated by those of skill in the art that such discussion generally is applicable for gradient index fibers as well.

In order to propagate light without loss, the light must be incident within the core of the fiber optic at an angle greater than the critical angle, which may be represented as $\text{Sin}^{-1}\{n_1/n_0\}$, where $n_0$ is the index of refraction of the core and $n_1$ is the index of refraction of the cladding. Thus, all light must enter the fiber at an acceptance angle equal to or less than phi, with phi=$2\times\text{Sin}^{-1}\{\sqrt{(n_0^2-n_1^2)}\}$, or it will not be propagated in a desired manner.

For light entering a fiber optic, it must enter within the acceptance angle phi. Similarly, when the light exits a fiber optic, it will exit the fiber optic within a cone of angle chi as illustrated in FIG. 4A. The value $\sqrt{(n_0^2-n_1^2)}$ is referred to as the aperture of the fiber optic. For example, a typical fiber optic may have an aperture of 0.5, and an acceptance angle of 60°.

Consider using a fiber optic as a light source. One end is illuminated by a light source (such as light source 11 of FIG. 1), and the other is held near a surface. The fiber optic will emit a cone of light as illustrated in FIG. 4A. If the fiber optic is held perpendicular to a surface it will create a circular light pattern on the surface. As the fiber optic is raised, the radius r of the circle will increase. As the fiber optic is lowered, the radius of the light pattern will decrease. Thus, the intensity of the light (light energy per unit area) in the illuminated circular area will increase as the fiber optic is lowered and will decrease as the fiber optic is raised.

The same principle generally is true for a fiber optic being utilized as a receiver. Consider mounting a light sensor on one end of a fiber optic and holding the other end near an illuminated surface. The fiber optic can only propagate light without loss when the light entering the fiber optic is incident on the end of the fiber optic near the surface if the light enters the fiber optic within its acceptance angle phi. A fiber optic utilized as a light receiver near a surface will only accept and propagate light from the circular area of radius r on the surface. As the fiber optic is raised from the surface, the area increases. As the fiber optic is lowered to the surface, the area decreases.

Figure 4B:
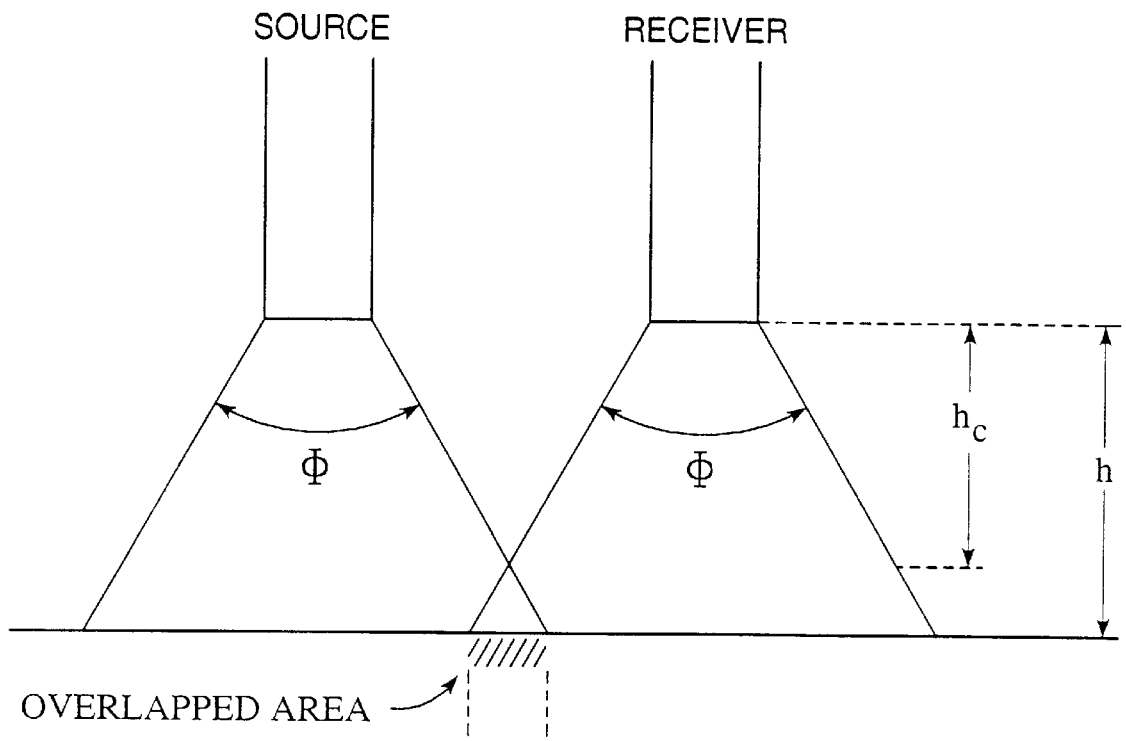
Figure 4C:
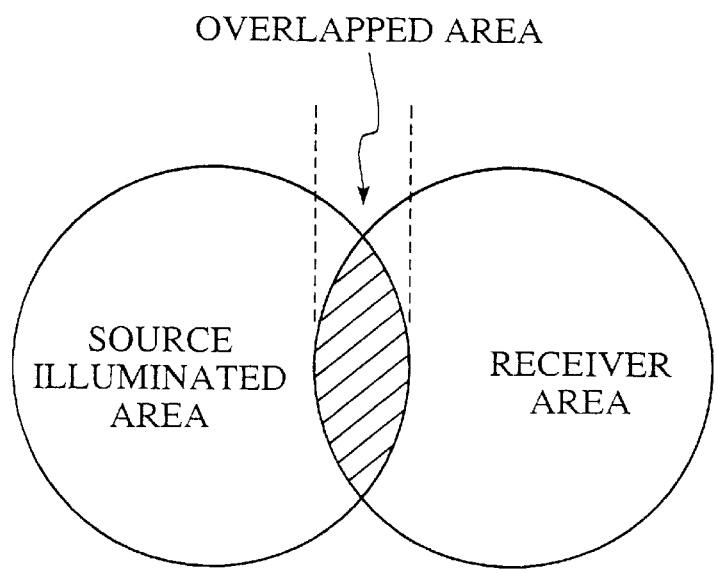

Consider two fiber optics parallel to each other as illustrated in FIG. 4B. For simplicity of discussion, the two fiber optics illustrated are identical in size and aperture. The following discussion, however, generally would be applicable for fiber optics that differ in size and aperture. One fiber optic is a source fiber optic, the other fiber optic is a receiver fiber optic. As the two fiber optics are held perpendicular to a surface, the source fiber optic emits a cone of light that illuminates a circular area of radius r. The receiver fiber optic can only accept light that is within its acceptance angle phi, or only light that is received within a cone of angle phi. If the only light available is that emitted by the source fiber optic, then the only light that can be accepted by the receiver fiber optic is the light that strikes the surface at the intersection of the two circles as illustrated in FIG. 4C. As the two fiber optics are lifted from the surface, the proportion of the intersection of the two circular areas relative to the circular area of the source fiber optic increases. As they near the surface, the proportion of the intersection of the two circular areas to the circular area of the source fiber optic decreases. If the fiber optics are held too close to the surface (i.e.. at or below a "critical height" $h_c$), the circular areas will no longer intersect and no light emitted from the source fiber optic will be received by the receiver fiber optic.

As discussed earlier, the intensity of the light in the circular area illuminated by the source fiber increases as the fiber is lowered to the surface. The intersection of the two cones, however, decreases as the fiber optic pair is lowered. Thus, as the fiber optic pair is lowered to a surface, the total intensity of light received by the receiver fiber optic increases to a maximal value, and then decreases sharply as the fiber optic pair is lowered still further to the surface. Eventually, the intensity will decrease essentially to zero at or below the critical height $h_c$ (assuming the object being measured is not translucent, as described more fully herein), and will remain essentially zero until the fiber optic pair is in contact with the surface. Thus, as a source-receiver pair of fiber optics as described above are positioned near a surface and as their height is varied, the intensity of light received by the receiver fiber optic reaches a maximal value at a "peaking height" $h_p$.

Again without being bound by theory, an interesting property of the peaking height $h_p$ has been observed. The peaking height $h_p$ is a function primarily of the geometry of fixed parameters, such as fiber apertures, fiber diameters and fiber spacing. Since the receiver fiber optic in the illustrated arrangement is only detecting a maximum value and not attempting to quantify the value, its maximum in general is independent of the surface color. It is only necessary that the surface reflect sufficient light from the intersecting area of the source and receiver fiber optics to be within the detection range of the receiver fiber optic light sensor. Thus, in general red or green or blue or any color surface will all exhibit a maximum at the same peaking height $h_p$.

Although the above discussion has focused on two fiber optics perpendicular to a surface, similar analysis is applicable for fiber optic pairs at other angles. When a fiber optic is not perpendicular to a surface, it generally illuminates an elliptical area. Similarly, the acceptance area of a receiver fiber optic generally becomes elliptical. As the fiber optic pair is moved closer to the surface, the receiver fiber optic also will detect a maximal value at a peaking height independent of the surface color or characteristics. The maximal intensity value measured when the fiber optic pair is not perpendicular to the surface, however, will be less than the maximal intensity value measured when the fiber optic pair is perpendicular to the surface.

Figure 5A:
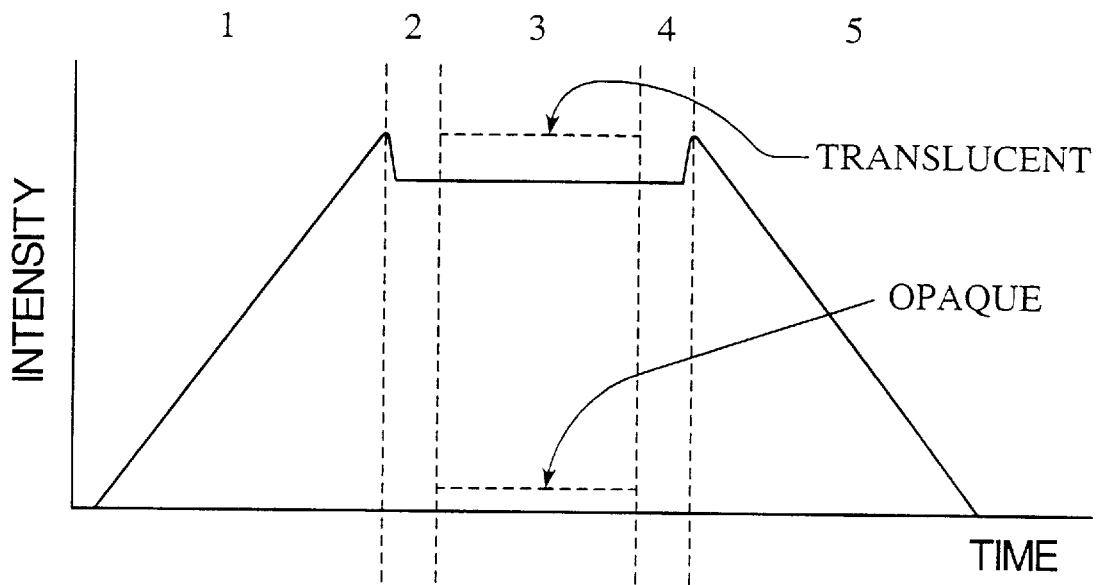
FIGS. 5A and 5B illustrate the light amplitude received by fiber optic light receivers as the receivers are moved towards and away from an object.
Figure 5B:
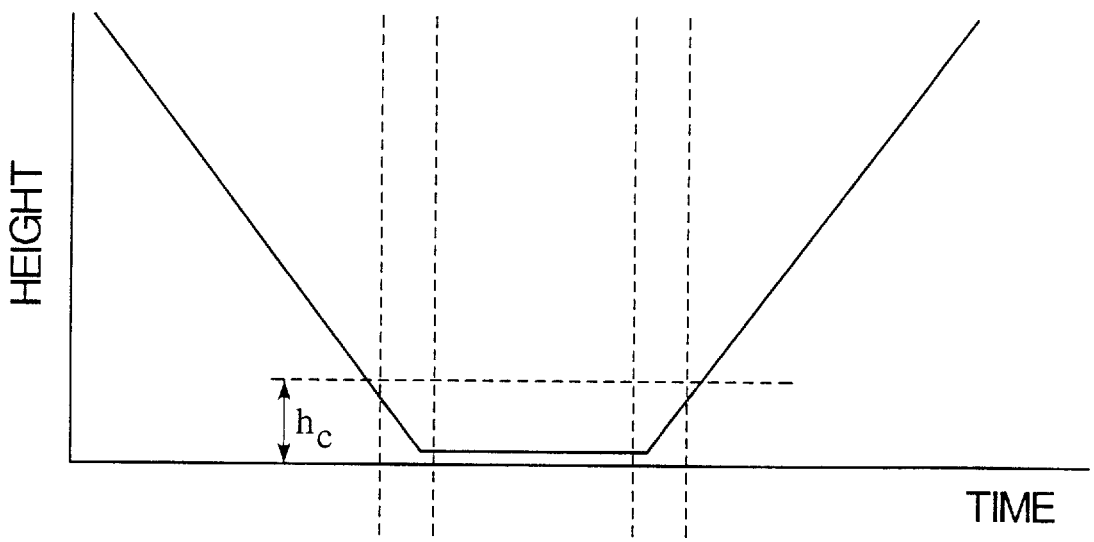

Referring now to FIGS. 5A and 5B, the intensity of light received as a fiber optic source-receiver pair is moved to and from a surface will now be described. FIG. 5A illustrates the intensity of the received light as a function of time. Corresponding FIG. 5B illustrates the height of the fiber optic pair from the surface of the object being measured. FIGS. 5A and 5B illustrate (for ease of discussion) a relatively uniform rate of motion of the fiber optic pair to and from the surface of the object being measured (although similar illustrations/analysis would be applicable for non-uniform rates as well).

FIG. 5A illustrates the intensity of received light as the fiber optic pair is moved to and then from a surface. While FIG. 5A illustrates the intensity relationship for a single receiver fiber optic, similar intensity relationships would be expected to be observed for other receive fiber optics, such as, for example, the multiple receiver fiber optics of FIGS. 1 and 2. In general with the preferred embodiment described above, all fifteen fiber optic receivers (of fibers 7) will exhibit curves similar to that illustrated in FIG. 5A.

FIG. 5A illustrates five regions. In region 1, the probe is moved towards the surface of the object being measured, which causes the received light intensity to increase. In region 2, the probe is moved past the peaking height, and the received light intensity peaks and then falls off sharply. In region 3, the probe essentially is in contact with the surface of the object being measured. As illustrated, the received intensity in region 3 will vary depending upon the translucence of the object being measured. If the object is opaque, the received light intensity will be very low, or almost zero (perhaps out of range of the sensing circuitry ). If the object is translucent, however, the light intensity will be quite high, but in general should be less than the peak value. In region 3, the probe is lifted and the light intensity rises sharply to a maximum value. In region 5, the probe is lifted further away from the object, and the light intensity decreases again.

As illustrated, two peak intensity values (discussed as P1 and P2 below) should be detected as the fiber optic pair moves to and from the object at the peaking height $h_p$. If peaks P1 and P2 produced by a receiver fiber optic are the same value, this generally is an indication that the probe has been moved to and from the surface of the object to be measured in a consistent manner. If peaks P1 and P2 are of different values, then these may be an indication that the probe was not moved to and from the surface of the object in a desired manner, or hat the surface is curved or textured, as described more fully herein. In such a case, the data may be considered suspect and rejected. In addition, peaks P1 and P2 for each of the perimeter fiber optics (see, e.g., FIG. 2) should occur at the same peaking height (assuming the geometric attributes of the perimeter fiber optics, such as aperture, diameter and spacing from the source fiber optic, etc.). Thus, the perimeter fiber optics of a probe moved in a consistent, perpendicular manner to and from the surface of the object being measured should have peaks P1 and P2 that occur at the same height. Monitoring receiver fibers from the perimeter receiver fiber optics and looking for simultaneous (or near simultaneous, e.g., within a predetermined range) peaks P1 and P2 provides a mechanism for determining if the probe is held at a desired perpendicular angle with respect to the object being measured.

In addition, the relative intensity level in region 3 serves as an indication of the level of translucency of the object being measured. Again, such principles generally are applicable to the totality of receiver fiber optics in the probe (see, e.g., fibers 7 of FIGS. 1 and 3). Based on such principles, measurement techniques that may be applicable with respect to embodiments disclosed herein will now be described.

Figure 6:
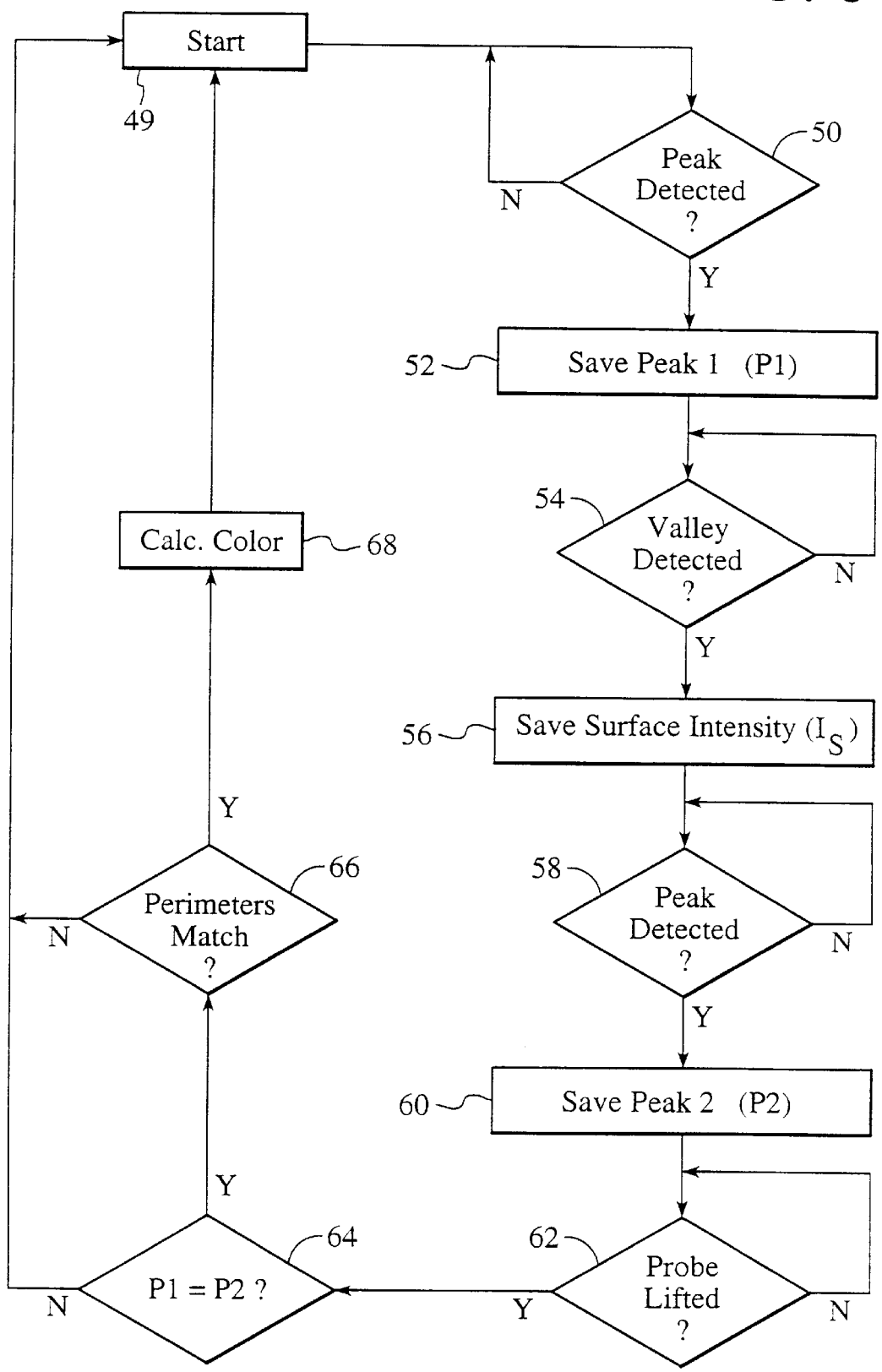
FIG. 6 is a flow chart illustrating a color measuring method in accordance with an embodiment of the present invention.

FIG. 6 is a flow chart illustrating a general measuring technique that may be used in accordance with certain embodiments of the present invention.. Step 49 indicates the start or beginning of a color/optical measurement. During step 49, any equipment initialization, diagnostic or setup procedures may be performed. Audio or visual information or other indicia may be given to the operator to inform the operator that the system is available and ready to take a measurement. Initiation of the color/optical measurement commences by the operator moving the probe towards the object to be measured, and may be accompanied by, for example, activation of switch 17 (see FIG. 1).

In step 50, the system on a continuing basis monitors the intensity levels for the receiver fiber optics (see, e.g., fibers 7 of FIG. 1). If the intensity is rising, step 50 is repeated until a peak is detected. If a peak is detected, the process proceeds to step 52. In step 52, measured peak intensity P1, and the time at which such peak occurred, are stored in memory (such as in memory included as a part of microprocessor 10), and the process proceeds to step 54. In step 54, the system continues to monitor the intensity levels of the receiver fiber optics. If the intensity is falling, step 54 is repeated. If a "valley" or plateau is detected (i.e., the intensity is no longer falling, which generally indicates contact or near contact with the object), then the process proceeds to step 56. In step 56, the measured surface intensity (IS) is stored in memory, and the process proceeds to step 58. In step 58, the system continues to monitor the intensity levels of the receiver fibers. If the intensity is rising, step 58 is repeated until a peak is detected. If a peak is detected, the process proceeds to step 60. In step 60, measured peak intensity P2, and the time at which such peak occurred, are stored in memory, and the process proceeds to step 62. In step 62, the system continues to monitor the intensity levels of the receiver fiber optics. Once the received intensity levels begin to fall from peak P2, the system perceives that region 5 has been entered (see, e.g., FIG. 5A), and the process proceeds to step 64.

In step 64, the system, under control of microprocessor 10, may analyze the collected data taken by the sensing circuitry for the various receiver fiber optics. In step 64, peaks P1 and P2 of one or more of the various fiber optics may be compared. If any of peaks P1 and P2 for any of the various receiver fiber optics have unequal peak values, then the data may be rejected, and the entire color measuring process repeated. Again, unequal values of peaks P1 and P2 may be indicative, for example, that the probe was moved in a non-perpendicular or otherwise unstable manner (i.e., angular or lateral movement), and, for example, peak P1 may be representative of a first point on the object, while peak P2 may be representative of a second point on the object. As the data is suspect, in a preferred embodiment of the present invention, data taken in such circumstances are rejected in step 64.

If the data are not rejected in step 64, the process proceeds to step 66. In step 66, the system analyzes the data taken from the neutral-density-filtered receivers from each of the perimeter fiber optics (e.g., R1 to R3 of FIG. 2). If the peaks of the perimeter fiber optics did not occur at or about the same point in time, this may be indicative, for example, that the probe was not held perpendicular to the surface of the object being measured. As non-perpendicular alignment of the probe with the surface of the object being measured may cause suspect results, in a preferred embodiment of the present invention, data taken in such circumstances are rejected in step 66. In one preferred embodiment, detection of simultaneous or near simultaneous peaking (peaking within a predetermined range of time) serves as an acceptance criterion for the data, as perpendicular alignment generally is indicated by simultaneous or near simultaneous peaking of the perimeter fiber optics. In other embodiments, step 66 includes an analysis of peak values P1 and P2 of the perimeter fiber optics. In such embodiments, the system seeks to determine if the peak values of the perimeter fiber optics (perhaps normalized with any initial calibration data) are equal within a defined range. If the peak values of the perimeter fiber optics are within the defined range, the data may be accepted, and if not, the data may be rejected. In still other embodiments, a combination of simultaneous peaking and equal value detection are used as acceptance/rejection criteria for the data, and/or the operator may have the ability (such as through key pad switches 12) to control one or more of the acceptance criteria ranges. With such capability, the sensitivity of the system may be controllably altered by the operator depending upon the particular application and operative environment, etc.

If the data are not rejected in step 66, the process proceeds to step 68. In step 68, the data may be processed in a desired manner to produce output color/optical measurement data. For example, such data may be normalized in some manner, or adjusted based on temperature compensation, or translucency data, or gloss data, or surface texture data or nonperpendicular angle data or other data detected by the system. The data also may be converted to different display or other formats, depending on the intended use of the data. In addition, the data indicative of the translucence of the object and/or glossiness of the object also may be quantified and/or displayed in step 68. After step 68, the process may proceed to starting step 49, or the process may be terminated, etc. As indicated previously, such data also may be compared with previously-stored data for purposes of making assessments or predictions, etc., of a current or future condition or status.

In accordance with the process illustrated in FIG. 6, three light intensity values (P1, P2 and IS) are stored per receiver fiber optic to make color and translucency, etc., measurements. If stored peak values P1 and P2 are not equal (for some or all of the receivers), this is an indication that the probe was not held steady over one area, and the data may be rejected (in other embodiments, the data may not be rejected, although the resulting data may be used to produce an average of the measured data). In addition, peak values P1 and P2 for the three neutral density perimeter fiber optics should be equal or approximately equal; if this is not the case, then this is an indication that the probe was not held perpendicular or a curved surface is being measured. In other embodiments, the system attempts to compensate for curved surfaces and/or nonperpendicular angles. In any event, if the system cannot make a color/optical measurement, or if the data is rejected because peak values P1 and P2 are unequal to an unacceptable degree or for some other reason, then the operator is notified so that another measurement or other action may be taken (such as adjust the sensitivity).

With a system constructed and operating as described above, color/optical measurements may be taken of an object, with accepted data having height and angular dependencies removed. Data not taken at the peaking height, or data not taken with the probe perpendicular to the surface of the object being measured, etc., are rejected in a certain embodiments. In other embodiments, data received from the perimeter fiber optics may be used to calculate the angle of the probe with respect to the surface of the object being measured, and in such embodiments non-perpendicular or curved surface data may be compensated instead of rejected. It also should be noted that peak values P1 and P2 for the neutral density perimeter fiber optics provide a measurement of the luminance (gray value) of the surface of the object being measured, and also may serve to quantify the optical properties.

The translucency of the object being measured may be quantified as a ratio or percentage, such as, for example, (IS/P1) X 100%. In other embodiments, other methods of quantifying translucency data provided in accordance with the present invention are utilized, such as some other arithmetic function utilizing IS and P1 or P2, etc. Translucence information, as would be known to those in the art, could be used to quantify and/or adjust the output color data, etc.

In another particular aspect of the present invention, data generated in accordance with the present invention may be used to implement an automated material mixing/generation machine and/or method. Certain objects/materials, such as dental prostheses or fillings, are made from porcelain or other powders/resins/materials or tissue substitutes that may be combined in the correct ratios or modified with additives to form the desired color of the object/prosthesis. Certain powders often contain pigments that generally obey Beer's law and/or act in accordance with Kubelka-Munk equations and/or Saunderson equations (if needed) when mixed in a recipe. Color and other data taken from a measurement in accordance with the present invention may be used to determine or predict desired quantities of pigment or other materials for the recipe. Porcelain powders and other materials are available in different colors, opacities, etc. Certain objects, such as dental prostheses, may be layered to simulate the degree of translucency of the desired object (such as to simulate a human tooth). Data generated in accordance with the present invention also may be used to determine the thickness and position of the porcelain or other material layers to more closely produce the desired color, translucency, surface characteristics, etc. In addition, based on fluorescence data for the desired object, the material recipe may be adjusted to include a desired quantity of fluorescing-type material. In yet other embodiments, surface characteristics (such as texture) information (as more fully described herein) may be used to add a texturing material to the recipe, all of which may be carried out in accordance with the present invention. In yet other embodiments, the degree of surface polish to the prosthesis may be monitored or adjusted, based on gloss data derived in accordance with the present invention.

For more information regarding such pigment-material recipe type technology, reference may be made to: "The Measurement of Appearance," Second Edition, edited by Hunter and Harold, copyright 1987; "Principles of Color Technology," by Billmeyer and Saltzman, copyright 1981; and "Pigment Handbook," edited by Lewis, copyright 1988. All of the foregoing are believed to have been published by John Wiley & Sons, Inc., New York, N.Y. and all of which are hereby incorporated by reference.

In certain operative environments, such as dental applications, contamination of the probe is of concern. In certain embodiments of the present invention, implements to reduce such contamination are provided.

Figure 7A:
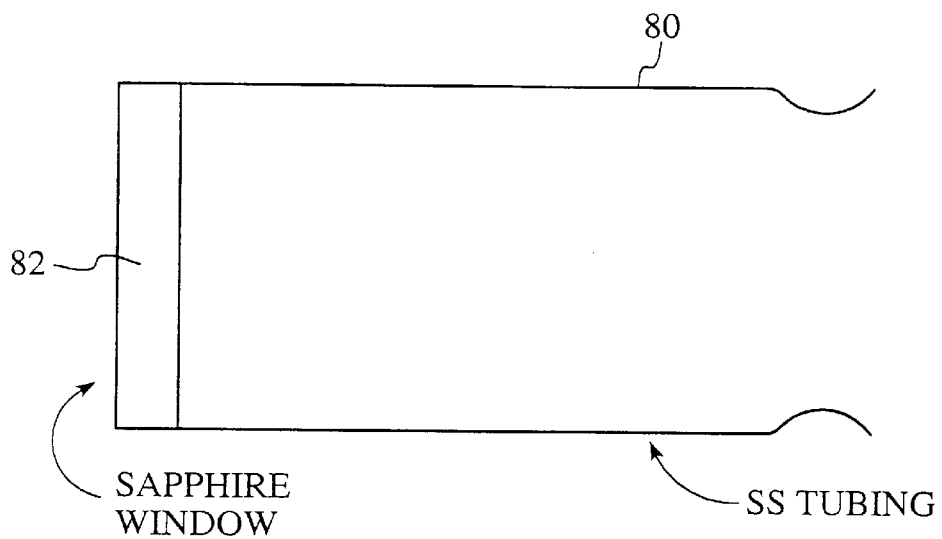
FIGS. 7A and 7B illustrate a protective cap that may be used with certain embodiments of the present invention.
Figure 7B:
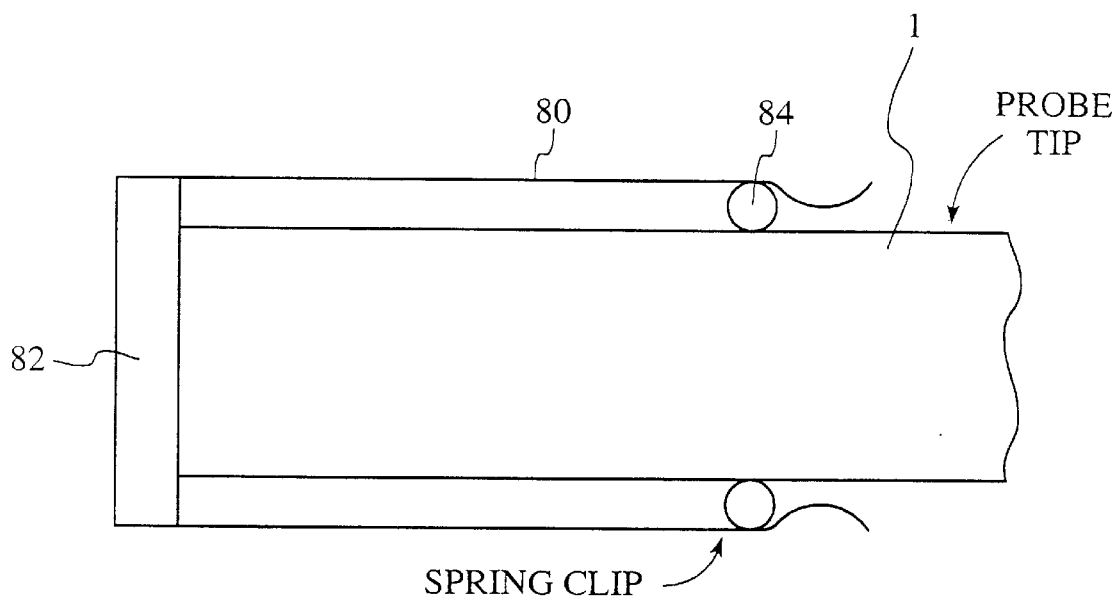

FIGS. 7A and 7B illustrate a protective cap that may be used to fit over the end of probe tip 1. Such a protective cap consists of body 80, the end of which is covered by optical window 82, which in a preferred embodiment consists of a structure having a thin sapphire window. In a preferred embodiment, body 80 consists of stainless steel. Body 80 fits over the end of probe tip 1 and may be held into place by, for example, indentations formed in body 80, which fit with ribs 84 (which may be a spring clip or other retainer) formed on probe tip 1. In other embodiments, other methods of affixing such a protective cap to probe tip 1 are utilized. The protective cap may be removed from probe tip 1 and sterilized in a typical autoclave, hot steam, chemiclave or other sterilizing system.

The thickness of the sapphire window should be less than the peaking height of the probe in order to preserve the ability to detect peaking in accordance with the present invention, and preferably has a thickness less than the critical height at which the source/receiver cones overlap (see FIGS. 4B and 4C). It also is believed that sapphire windows may be manufactured in a reproducible manner, and thus any light attenuation from one cap to another may be reproducible. In addition, any distortion of the color/optical measurements produced by the sapphire window may be calibrated out by microprocessor 10.

Similarly, in other embodiments body 80 has a cap with a hole in the center (as opposed to a sapphire window), with the hole positioned over the fiber optic source/receivers. The cap with the hole serves to prevent the probe from coming into contact with the surface, thereby reducing the risk of contamination. It should be noted that, with such embodiments, the hole is positioned so that light from/to the light source/receiver elements of the probe tip is not adversely affected by the cap.

Figure 8A:
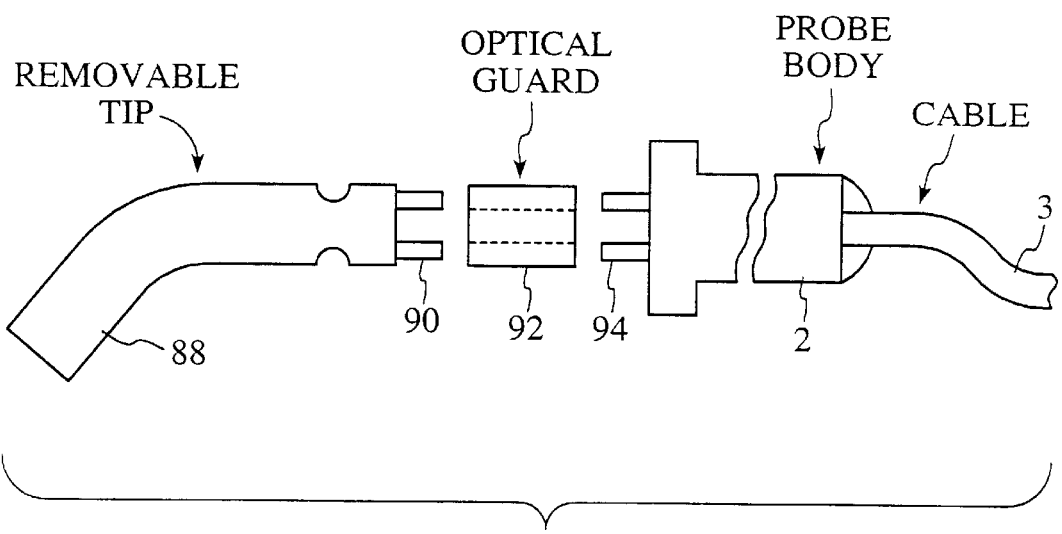
FIGS. 8A and 8B illustrate removable probe tips that may be used with certain embodiments of the present invention.
Figure 8B:
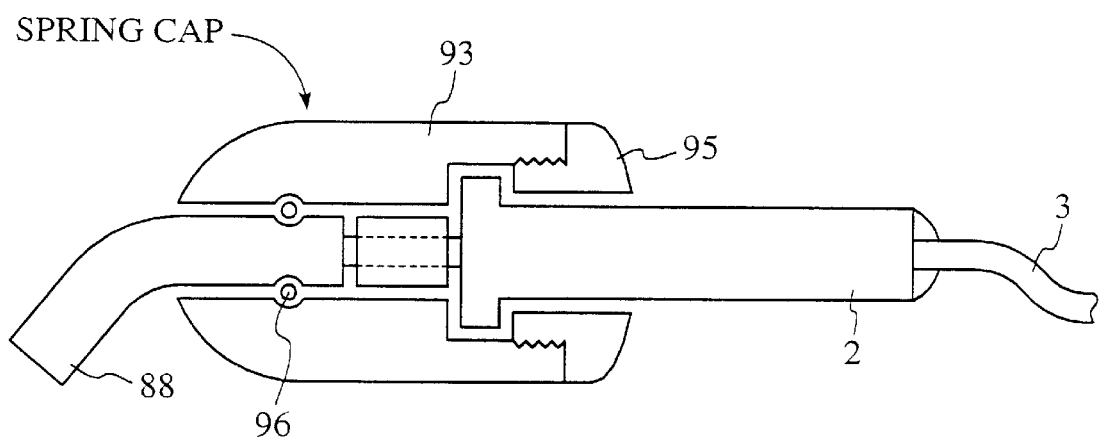

FIGS. 8A and 8B illustrate another embodiment of a removable probe tip that may be used to reduce contamination in accordance with the present invention. As illustrated in FIG. 8A, probe tip 88 is removable, and includes four (or a different number, depending upon the application) fiber optic connectors 90, which are positioned within optical guard 92 coupled to connector 94. Optical guard 92 serves to prevent "cross talk" between adjacent fiber optics. As illustrated in FIG. 8B, in this embodiment removable tip 88 is secured in probe tip housing 93 by way of spring clip 96 (other removable retaining implements are utilized in other embodiments). Probe tip housing 93 may be secured to base connector 95 by a screw or other conventional fitting. It should be noted that, with this embodiment, different size tips may be provided for different applications, and that an initial step of the process may be to install the properly-sized (or fitted tip) for the particular application. Removable tip 88 also may be sterilized in a typical autoclave, hot steam, chemiclave or other sterilizing system, or disposed of. In addition, the entire probe tip assembly is constructed so that it may be readily disassembled for cleaning or repair. In certain embodiments the light source/receiver elements of the removable tip are constructed of glass, silica or similar materials, thereby making them particularly suitable for autoclave or similar high temperature/pressure cleaning methods, which in certain other embodiments the light source/receiver elements of the removable tip are constructed of plastic or other similar materials, which may be of lower cost, thereby making them particularly suitable for disposable-type removable tips, etc.

In still other embodiments, a plastic, paper or other type shield (which may be disposable, cleanable/reusable or the like) may be used in order to address any contamination concerns that may exist in the particular application. In such embodiments, the methodology may include positioning such a shield over the probe tip prior to taking color/optical measurements, and may include removing and disposing/cleaning the shield after taking color/optical measurements, etc.

Figure 19A:
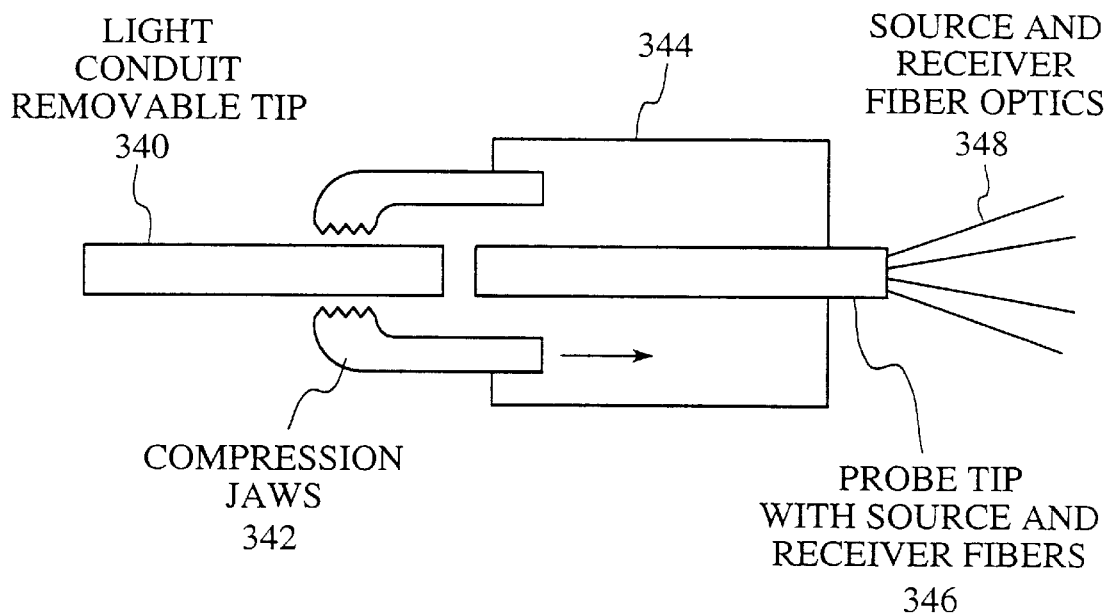
FIGS. 19A to 19C illustrate embodiments of the present invention in which coherent light conduits may serve as removable probe tips.
Figure 19B:
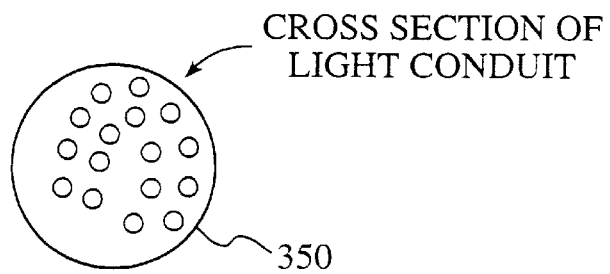

A further embodiment of the present invention utilizing an alternate removable probe tip will now be described with reference to FIGS. 19A–19C. As illustrated in FIG. 19A, this embodiment utilizes removable, coherent light conduit 340 as a removable tip. Light conduit 340 is a short segment of a light conduit that preferably may be a fused bundle of small fiber optics, in which the fibers are held essentially parallel to each other, and the ends of which are highly polished. Cross-section 350 of light conduit 340 is illustrated in FIG. 19B. Light conduits similar to light conduit 340 have been utilized in what are known as borescopes, and also have been utilized in medical applications such as endoscopes.

Light conduit 340 in this embodiment serves to conduct light from the light source to the surface of the object being measured, and also to receive reflected light from the surface and conduct it to light receiver fiber optics 346 in probe handle 344. Light conduit 340 is held in position with respect to fiber optics 346 by way or compression jaws 342 or other suitable fitting or coupled that reliably positions light conduit 340 so as to couple light effectively to/from fiber optics 346. Fiber optics 346 may be separated into separate fibers/light conduits 348, which may be coupled to appropriate light sensors, etc., as with previously described embodiments.

In general, the aperture of the fiber optics used in light conduit 340 may be chosen to match the aperture of the fiber optics for the light source and the light receivers or alternately the light conduit aperture could be greater than or equal to the largest source or receive aperture. Thus, the central part of the light conduit may conduct light from the light source and illuminate the surface as if it constituted a single fiber within a bundle of fibers. Similarly, the outer portion of the light conduit may receive reflected light and conduct it to light receiver fiber optics as if it constituted single fibers. Light conduit 340 has ends that preferably are highly polished and cut perpendicular, particularly the end coupling light to fiber optics 346. Similarly, the end of fiber optics 346 abutting light conduit 340 also is highly polished and cut perpendicular to a high degree of accuracy in order to minimize light reflection and cross talk between the light source fiber optic and the light receiver fiber optics and between adjacent receiver fiber optics. Light conduit 340 offers significant advantages including in the manufacture and installation of such a removable tip. For example, the probe tip need not be particularly aligned with the probe tip holder; rather, it only needs to be held against the probe tip holder such as with a compression mechanism (such as with compression jaws 342) so as to couple light effectively to/from fiber optics 346. Thus, such a removable tip mechanism may be implemented without alignment tabs or the like, thereby facilitating easy installation of the removable probe tip. Such an easy installable probe tip may thus be removed and cleaned prior to installation, thereby facilitating use of the color/optical measuring apparatus by dentists, medical professions or others working in an environment in which contamination may be a concern. Light conduit 340 also may be implemented, for example, as a small section of light conduit, which may facilitate easy and low cost mass production and the like.

Figure 19C:
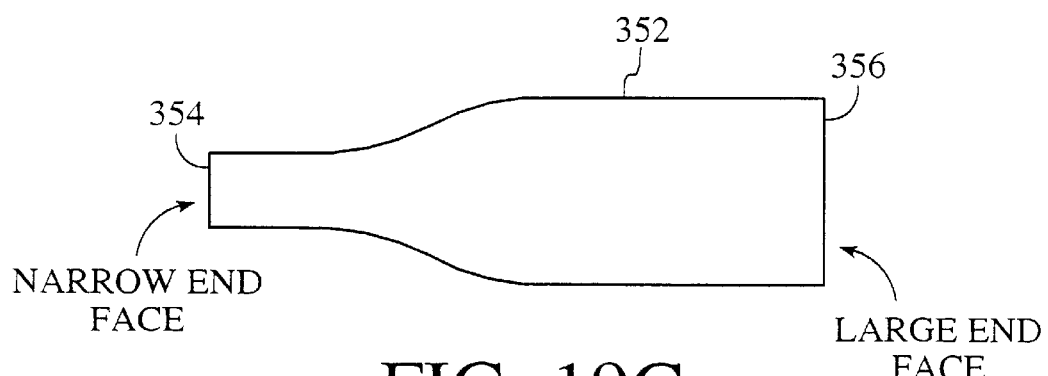

A further embodiment of such a light conduit probe tip is illustrated as light conduit 352 in FIG. 19C. Light conduit 352 is a light conduit that is narrower on one end (end 354) than the other end (end 356). Contoured/tapered light conduits such as light conduit 35 may be fabricated by heating and stretching a bundle of small fiber optics as part of the fusing process. Such light conduits have an additional interesting property of magnification or reduction. Such phenomena result because there are the same number of fibers in both ends. Thus, light entering narrow end 354 is conducted to wider end 356, and since wider end 356 covers a larger area, it has a magnifying affect.

Light conduit 352 of FIG. 19C may be utilized in a manner similar to light conduit 340 (which in general may be cylindrical) of FIG. 19A. Light conduit 352, however, measures smaller areas because of its reduced size at end 354. Thus, a relatively larger probe body may be manufactured where the source fiber optic is spaced widely from the receiver fiber optics, which may provide an advantage in reduced light reflection and cross talk at the junction, while still maintaining a small probe measuring area. Additionally, the relative sizes of narrow end 354 of light conduit 352 may be varied. This enables the operator to select the size/characteristic of the removable probe tip according to the conditions in the particular application. Such ability to select sizes of probe tips provides a further advantage in making optical characteristics measurements in a variety of applications and operative environments.

As should be apparent to those skilled in the art in view of the disclosures herein, light conduits 340 and 356 of FIGS. 19A and 19C need not necessarily be cylindrical/tapered as illustrated, but may be curved such as for specialty applications, in which a curved probe tip may be advantageously employed (such as in a confined or hard-to-reach place). It also should be apparent that light conduit 352 of FIG. 19C may be reversed (with narrow end 354 coupling light into fiber optics 346, etc., and wide end 356 positioned in order to take measurements) in order to cover larger areas.

Figure 9:
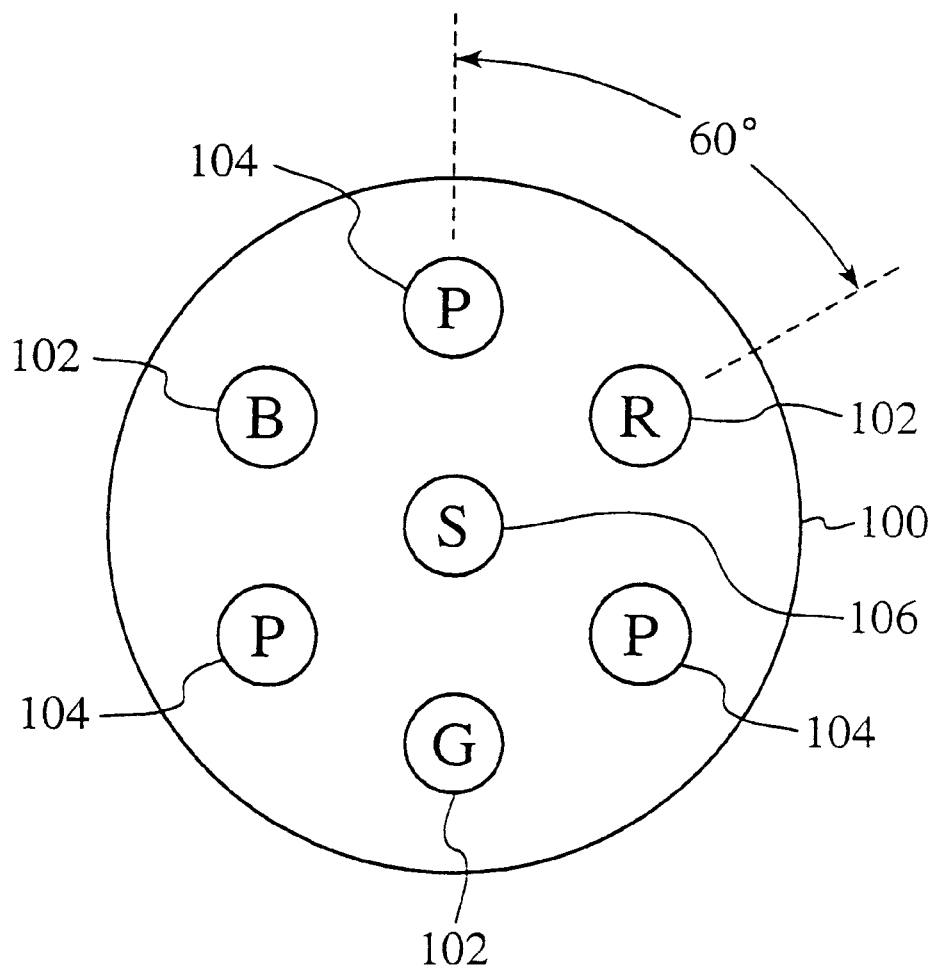
FIG. 9 illustrates a fiber optic bundle in accordance with another embodiment which may serve to further the understanding of preferred embodiments of the present invention.

With reference to FIG. 9, a tristimulus embodiment will now be described, which may aid in the understanding of, or may be used in conjunction with, certain embodiments disclosed herein. In general, the overall system depicted in FIG. I and discussed in detail elsewhere herein may be used with this embodiment. FIG. 9 illustrates a cross section of the probe tip fiber optics used in this embodiment.

Probe tip 100 includes central source fiber optic 106, surrounded by (and spaced apart from) three perimeter receiver fiber optics 104 and three color receiver fiber optics 102. Three perimeter receiver fiber optics 104 are optically coupled to neutral density filters and serve as height/angle sensors in a manner analogous to the embodiment describe above. Three color receiver fiber optics are optically coupled to suitable tristimulus filters, such as red, green and blue filters. With this embodiment, a measurement may be made of tristimulus color values of the object, and the process described with reference to FIG. 6 generally is applicable to this embodiment. In particular, perimeter fiber optics 104 may be used to detect simultaneous peaking or otherwise whether the probe is perpendicular to the object being measured.

Figure 10A:
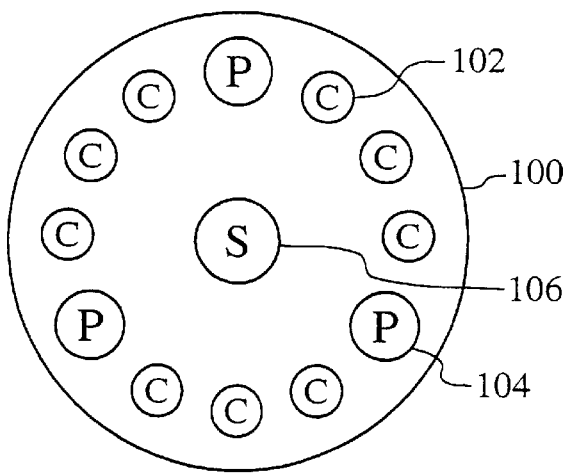
FIGS. 10A, 10B, 10C, and 10D illustrate and describe other fiber optic bundle configurations and principles, which may serve to further the understanding of preferred embodiments of the present invention.

FIG. 10A illustrates another such embodiment, similar to the embodiment discussed with reference to FIG. 9. Probe tip 100 includes central source fiber optic 106, surrounded by (and spaced apart from) three perimeter receiver fiber optics 104 and a plurality of color receiver fiber optics 102. The number of color receiver fiber optics 102, and the filters associated with such receiver fiber optics 102, may be chosen based upon the particular application. As with the embodiment of FIG. 9, the process described with reference to FIG. 6 generally is applicable to this embodiment.

Figure 10B:
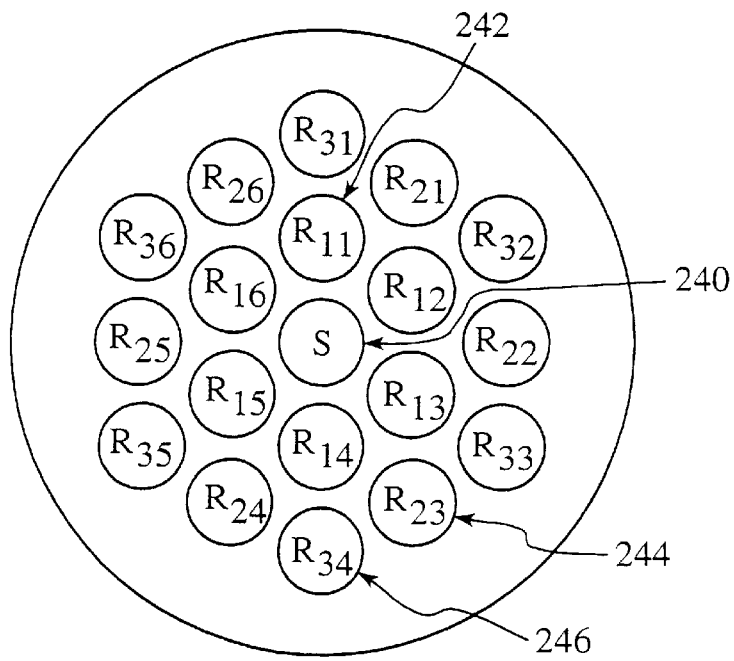

FIG. 10B illustrates another such embodiment in which there are a plurality of receiver fiber optics that surround central source fiber optic 240. The receiver fiber optics are arranged in rings surrounding the central source fiber optic. FIG. 10B illustrates three rings of receiver fiber optics (consisting of fiber optics 242, 244 and 246, respectively), in which there are six receiver fiber optics per ring. The rings may be arranged in successive larger circles as illustrated to cover the entire area of the end of the probe, with the distance from each receiver fiber optic within a given ring to the central fiber optic being equal (or approximately so). Central fiber optic 240 is utilized as the light source fiber optic and is connected to the light source in a manner similar to light source fiber optic 5 illustrated in FIG. 1.

The plurality of receiver fiber optics are each coupled to two or more fiber optics in a manner similar to the arrangement illustrated in FIG. 1 for splicing connector 4. One fiber optic from such a splicing connector for each receiver fiber optic passes through a neutral density filter and then to light sensor circuitry similar to the light sensor circuitry illustrated in FIG. 3. A second fiber optic from the splicing connector per receiver fiber optic passes through a Sharp Cutting Wrattan Gelatin Filter (or notch filter as previously described) and then to light sensor circuitry as discussed elsewhere herein. Thus, each of the receiver fiber optics in the probe tip includes both color measuring elements and neutral light measuring or "perimeter" elements.

Figure 10C:
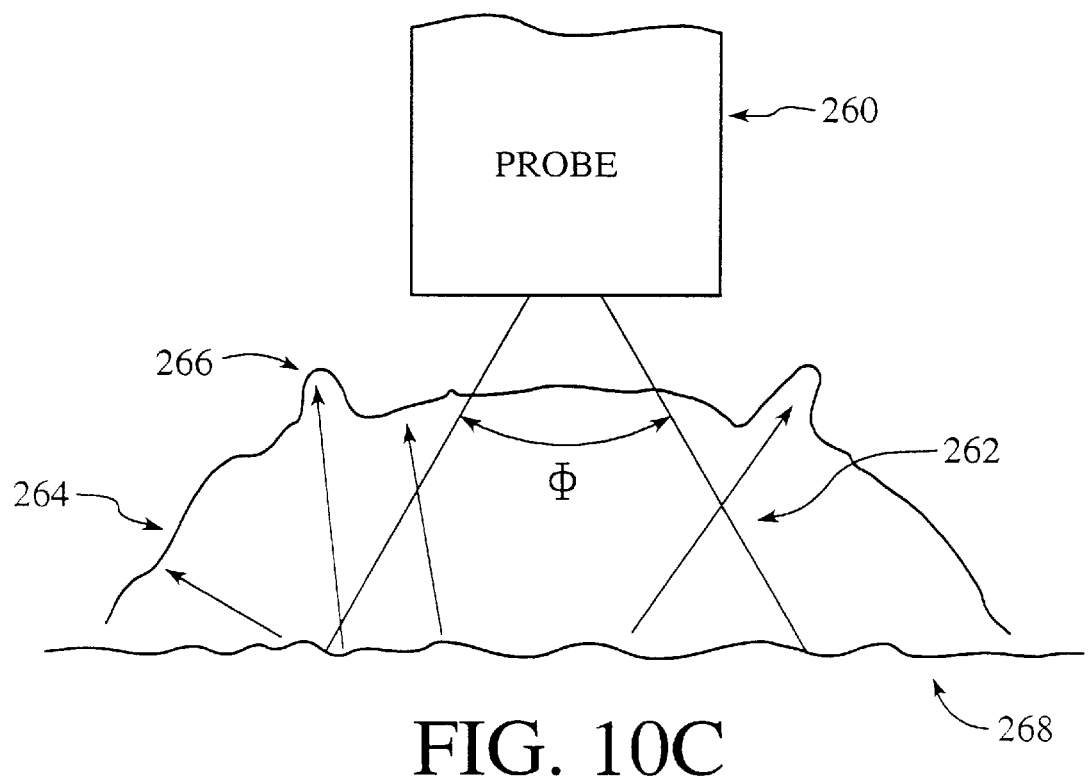
Figure 10D:
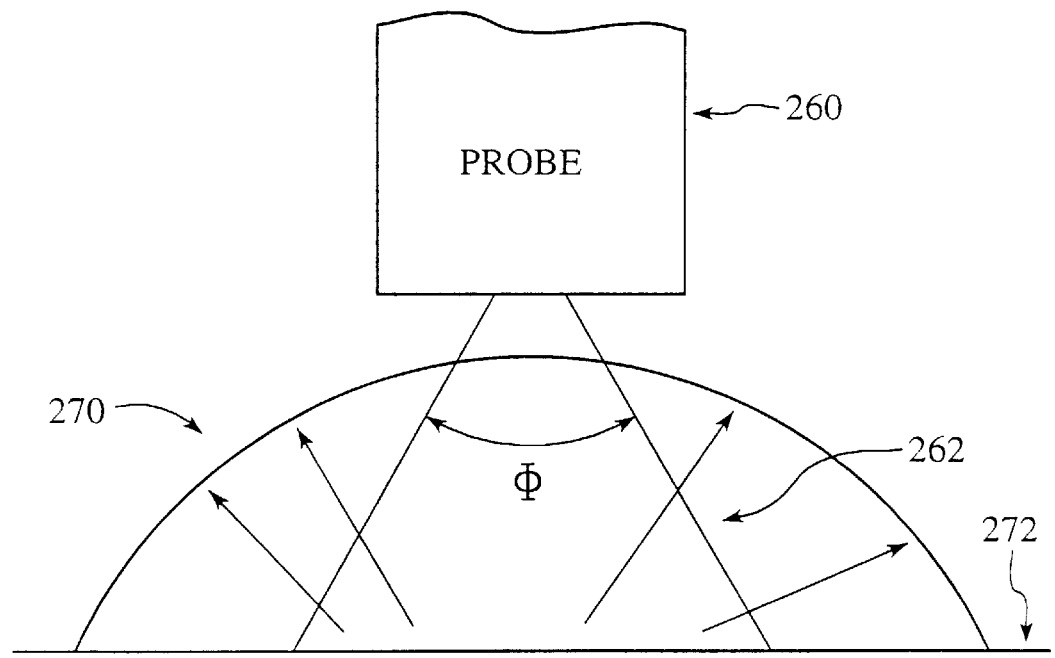

FIG. 10D illustrates the geometry of probe 260 (such as described above) illuminating an area on flat diffuse surface 272. Probe 260 creates light pattern 262 that is reflected diffusely from surface 272 in uniform hemispherical pattern 270. With such a reflection pattern, the reflected light that is incident upon the receiving elements in the probe will be equal (or nearly equal) for all elements if the probe is perpendicular to the surface as described above herein.

FIG. 10C illustrates a probe illuminating rough surface 268 or a surface that reflects light unevenly. The reflected light will exhibit hot spots or regions 266 where the reflected light intensity is considerably greater than it is on other areas 264. The reflected light pattern will be uneven when compared to a smooth surface as illustrate in FIG. 10D.

Since a probe as illustrated in FIG. 10B has a plurality of receiver fiber optics arranged over a large surface area, the probe may be utilized to determine the surface texture of the surface as well as being able to measure the color and translucency, etc., of the surface as described earlier herein. If the light intensity received by the receiver fiber optics is equal for all fiber optics within a given ring of receiver fiber optics, then generally the surface is smooth. If, however, the light intensity of receiver fibers in a ring varies with respect to each other, then generally the surface is rough. By comparing the light intensities measured within receiver fiber optics in a given ring and from ring to ring, the texture and other characteristics of the surface may be quantified.

Figure 11:
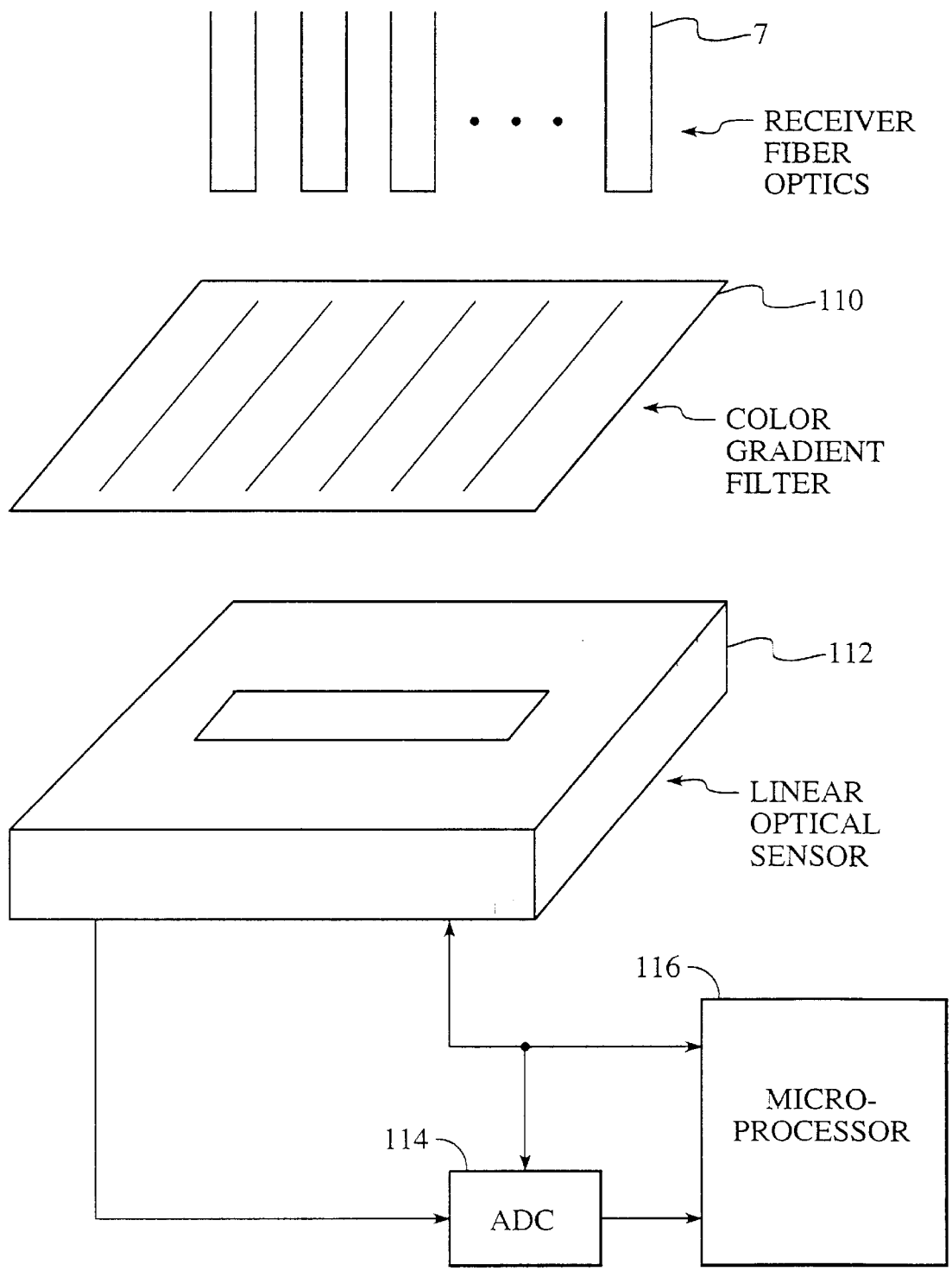
FIG. 11 illustrates a linear optical sensor array that may be used in certain embodiments of the present invention.

FIG. 11 illustrates an embodiment of the present invention in which linear optical sensors and a color gradient filter are utilized instead of light sensors S (and filters 22. etc.). Receiver fiber optics 7, which may be optically coupled to probe tip 1 as with the embodiment of FIG. 1, are optically coupled to linear optical sensor 112 through color gradient filter 110. In this embodiment, color gradient filter 110 may consist of series of narrow strips of cut-off type filters on a transparent or open substrate, which are constructed so as to positionally correspond to the sensor areas of linear optical sensor 112. An example of a commercially available linear optical sensor 112 is Texas Instruments part number TSL213, which has 61 photo diodes in a linear array. Light receiver fiber optics 7 are arranged correspondingly in a line over linear optical sensor 112. The number of receiver fiber optics may be chosen for the particular application, so long as enough are included to more or less evenly cover the full length of color gradient filter 110. With this embodiment, the light is received and output from receiver fiber optics 7, and the light received by linear optical sensor 112 is integrated for a short period of time (determined by the light intensity, filter characteristics and desired accuracy). The output of linear array sensor 112 is digitized by ADC 114 and output to microprocessor 116 (which may the same processor as microprocessor 10 or another processor).

In general, with the embodiment of FIG. 11, perimeter receiver fiber optics may be used as with the embodiment of FIG. 1, and in general the process described with reference to FIG. 6 is applicable to this embodiment.

Figure 12:
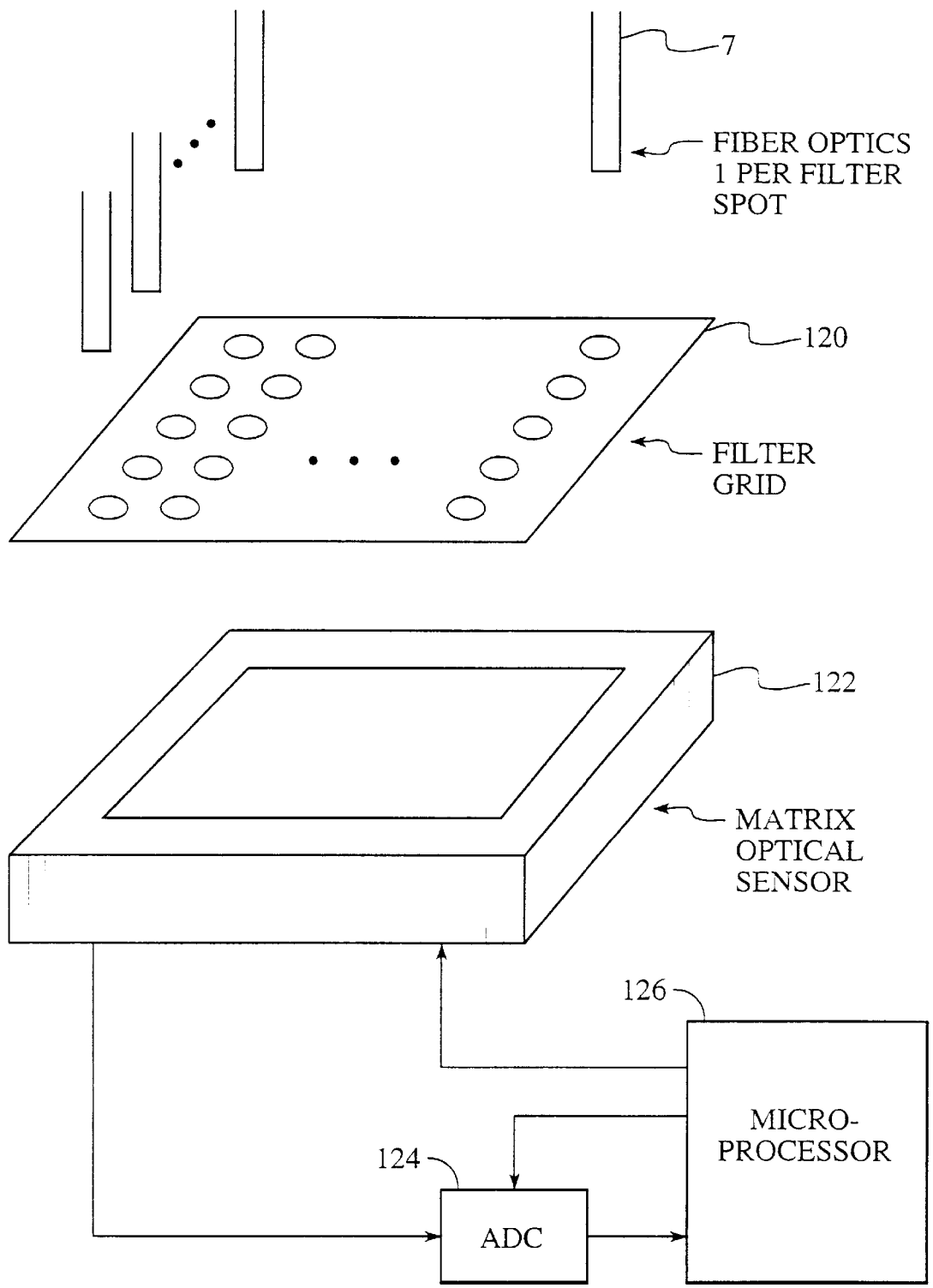
FIG. 12 illustrates a matrix optical sensor array that may be used in certain embodiments of the present invention.

FIG. 12 illustrates an embodiment of the present invention in which a matrix optical sensor and a color filter grid are utilized instead of light sensors 8 (and filters 22, etc.). Receiver fiber optics 7, which may be optically coupled to probe tip 1 as with the embodiment of FIG. 1, are optically coupled to matrix optical sensor 122 through filter grid 120. Filter grid 120 is a filter array consisting of a number of small colored spot filters that pass narrow bands of visible light. Light from receiver fiber optics 7 pass through corresponding filter spots to corresponding points on matrix optical sensor 122. In this embodiment, matrix optical sensor 122 may be a monochrome optical sensor array, such as CCD-type or other type of light sensor element such as may be used in a video camera. The output of matrix optical sensor 122 is digitized by ADC 124 and output to microprocessor 126 (which may the same processor as microprocessor 10 or another processor). Under control of microprocessor 126, matrix optical sensor 126 collects data from receiver fiber optics 7 through color filter grid 120.

In general, with the embodiment of FIG. 12, perimeter receiver fiber optics may be used as with the embodiment of FIG. 1, and in general the process described with reference to FIG. 6 also is applicable to this embodiment.

In general with the embodiments of FIGS. 11 and 12, the color filter grid may consist of sharp cut off filters as described earlier or it may consist of notch filters. As will be apparent to one skilled in the art, they may also be constructed of a diffraction grating and focusing mirrors such as those utilized in conventional monochromators.

As will be clear from the foregoing description, with the present invention a variety of types of spectral color/optical photometers (or tristimulus-type calorimeters) may be constructed, with perimeter receiver fiber optics used to collect color/optical data essentially free from height and angular deviations. In addition, in certain embodiments, the present invention enables color/optical measurements to be taken at a peaking height from the surface of the object being measured, and thus color/optical data may be taken without physical contact with the object being measured (in such embodiments, the color/optical data is taken only by passing the probe through region 1 and into region 2, but without necessarily going into region 3 of FIGS. 5A and 5B). Such embodiments may be utilized if contact with the surface is undesirable in a particular application. In the embodiments described earlier, however, physical contact (or near physical contact) of the probe with the object may allow all five regions of FIGS. 5A and 5B to be utilized, thereby enabling measurements to be taken such that translucency information also may be obtained. Both types of embodiments generally are within the scope of the invention described herein.

Figure 13A:
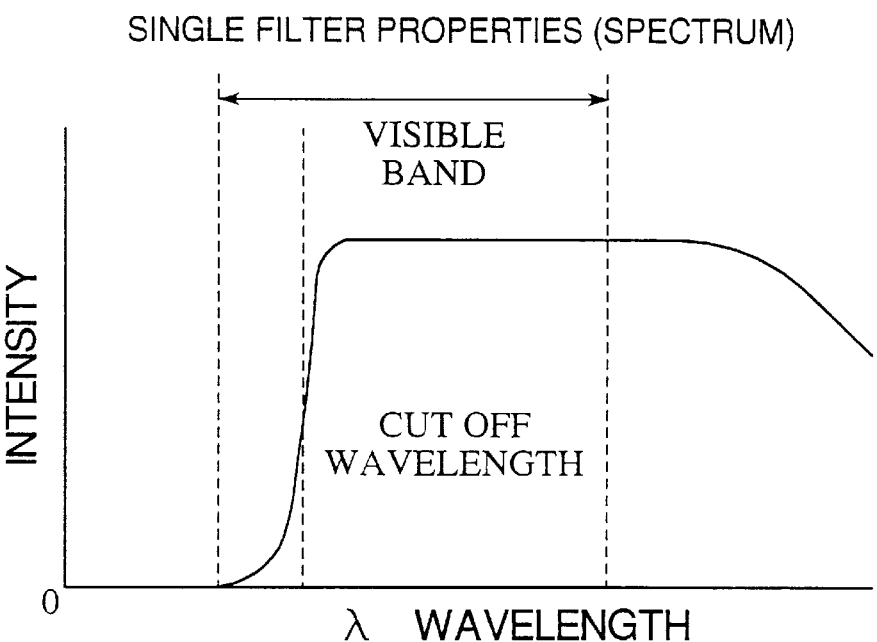
FIGS. 13A and 13B illustrate certain optical properties of a filter array hat may be used in certain embodiments of the present invention.
Figure 13B:
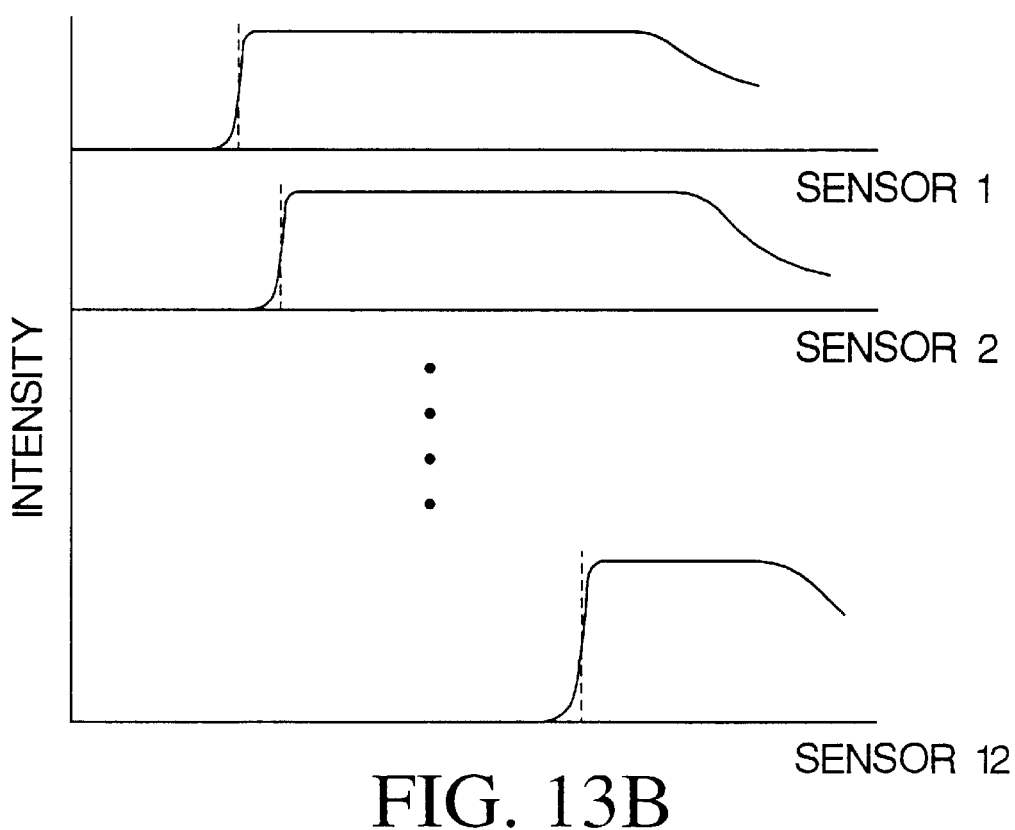

Additional description will now be provided with respect to cut-off filters of the type described in connection with the preferred embodiment(s) of FIGS. 1 and 3 (such as filters 22 of FIG. 3). FIG. 13A illustrates the properties of a single Kodak Sharp Cutting Wratten Gelatin Filter discussed in connection with FIG. 3. Such a cut-off filter passes light below a cut-off frequency (i.e., above a cut-off wavelength). Such filters may be manufactured to have a wide range of cut-off frequencies/wavelengths. FIG. 13B illustrates a number of such filters, twelve in a preferred embodiment, with cut-off frequencies/wavelengths chosen so that essentially the entire visible band is covered by the collection of cut-off filters.

Figure 14A:
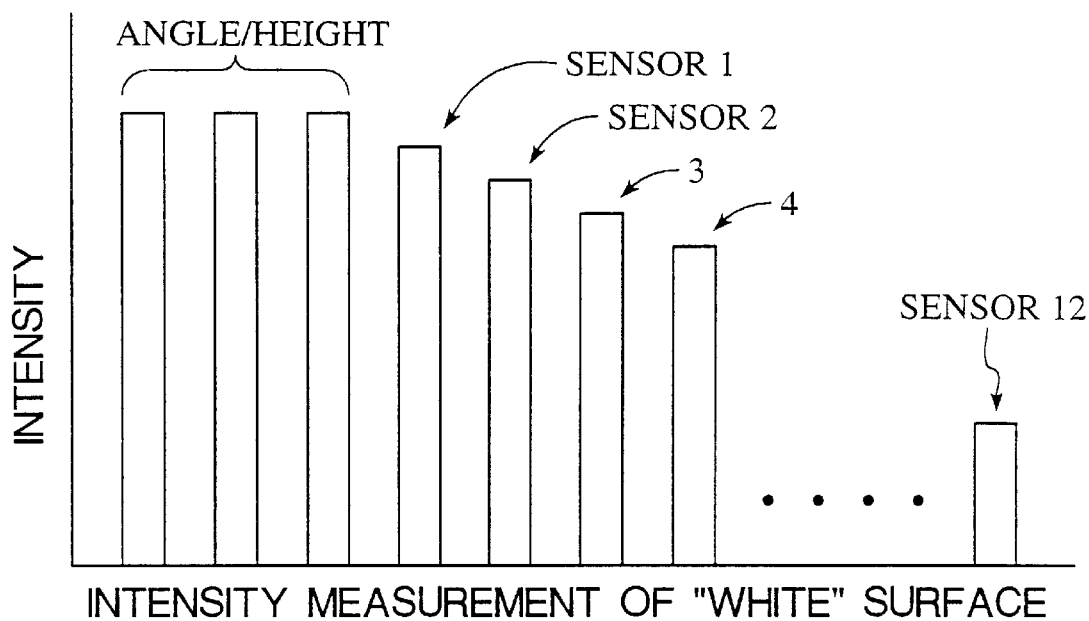
FIGS. 14A and 14B illustrate examples of received light intensities of receivers used in certain embodiments of the present invention.
Figure 14B:
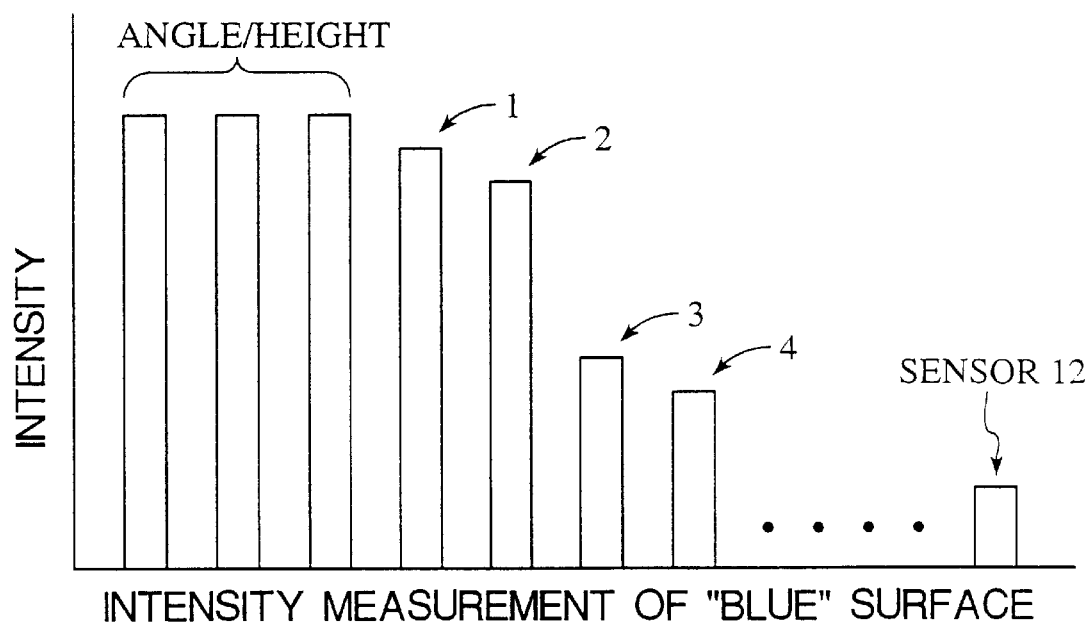

FIGS. 14A and 14B illustrate exemplary intensity measurements using a cut-off filter arrangement such as illustrated in FIG. 13B, first in the case of a white surface being measured (FIG. 14A), and also in the case of a blue surface being measured (FIG. 14B). As illustrated in FIG. 14A, in the case of a white surface, the neutrally filtered perimeter fiber optics, which are used to detect height and angle, etc., generally will produce the highest intensity (although this depends at least in part upon the characteristics of the neutral density filters). As a result or the stepped cut-off filtering provided by filters having the characteristics illustrated in FIG. 13B, the remaining intensities will gradually decrease in value as illustrated in FIG. 14A. In the case of a blue surface, the intensities will decrease in value generally as illustrated in FIG. 14B. Regardless of the surface, however, the intensities out of the filters will always decrease in value as illustrated, with the greatest intensity value being the output of the filter having the lowest wavelength cut-off value (i.e., passes all visible light up to blue), and the lowest intensity value being the output of the filter having the highest wavelength cut-off (i.e., passes only red visible light). As will be understood from the foregoing description, any color data detected that does not fit the decreasing intensity profiles of FIGS. 14A and 14B may be detected as an abnormality, and in certain embodiments detection of such a condition results in data rejection, generation of an error message or initiation of a diagnostic routine. etc.

Reference should be made to the FIGS. 1 and 3 and the related description for a detailed discussion of how such a cut-off filter arrangement may be utilized in accordance with the present invention.

Figure 15:
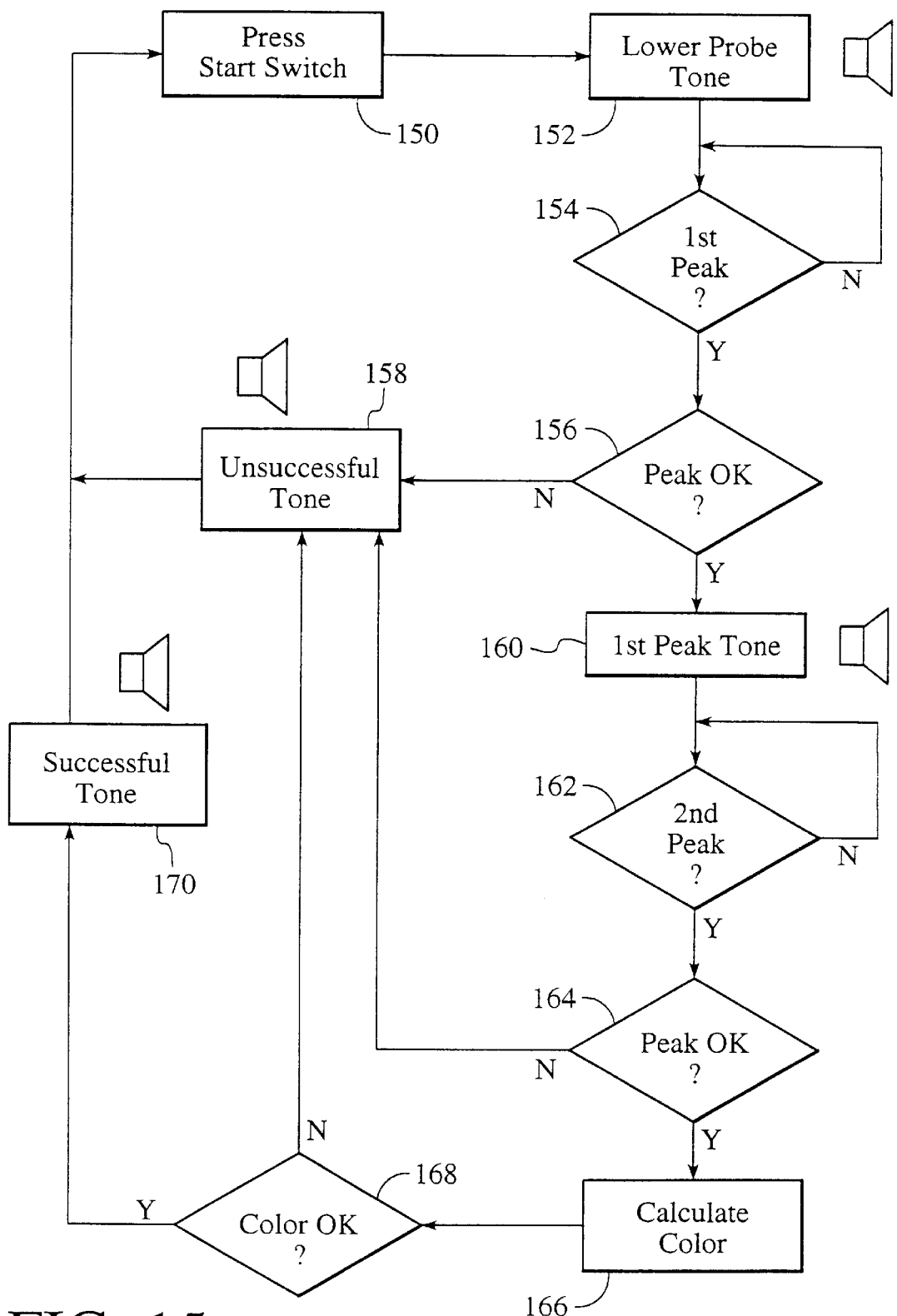
FIG. 15 is a flow chart illustrating audio tones that may be used in certain embodiments of the present invention.

FIG. 15 is a flow chart illustrating audio tones that may be used in certain preferred embodiments of the present invention. It has been discovered that audio tones (such as tones, beeps, voice or the like such as will be described) present a particularly useful and instructive means to guide an operator in the proper use of a color measuring system of the tape described herein.

The operator may initiate a color/optical measurement by activation of a switch (such as switch 17 of FIG. 1) at step 150. Thereafter, if the system is ready (set-up, initialized, calibrated. etc.), a lower-the-probe tone is emitted (such as through speaker 16 of FIG. 11) at step 152. The system attempts to detect peak intensity P1 at step 154. If a peak is detected, at step 156 a determination is made whether the measured peak P1 meets the applicable criteria (such as discussed above in connection with FIGS. 5A, SB and 6) If the measured peak P1 is accepted, a first peak acceptance tone is generated at step 160. If the measured peak P1 is not accepted, an unsuccessful tone is generated at step 158, and the system may await the operator to initiate a further color/optical measurement. Assuming that the first peak was accepted, the system attempts to detect peak intensity P2 at step 162. If a second peak is detected, at step 164 a determination is made whether the measured peak P2 meets the applicable criteria. If the measured peak P2 is accepted the process proceeds to color calculation step 166 (in other embodiments, a second peak acceptance tone also is generated at step 166). If the measured peak P2 is not accepted, an unsuccessful tone is generated at step 158, and the system may await the operator to initiate a further color/optical measurement. Assuming that the second peak was accepted, a color/optical calculation is made at step 166 (such as, for example. microprocessor 10 of FIG. 1 processing the data output from light sensors 8, etc.). At step 168, a determination is made whether the color calculation meets the applicable criteria. If the color calculation is accepted, a successful tone is generated at step 170. If the color calculation is not accepted, an unsuccessful tone is generated at step 158, and the system may await the operator to initiate a further color/optical measurement.

With unique audio tones presented to an operator in accordance with the particular operating state of the system, the operator's use of the system may be greatly facilitated. Such audio information also tends to increase operator satisfaction and skill level, as, for example, acceptance tones provide positive and encouraging feedback when the system is operated in a desired manner.

Further embodiments of the present invention will now be described with reference to FIGS. 16–18. The previously described embodiments generally rely on movement of the probe with respect to the object being measured. While such embodiments provide great utility in many applications, in certain applications, such as robotics, industrial control, automated manufacturing, etc. (such as positioning the object and,/or the probe to be in proximity to each other, detecting color/optical properties of the object, and then directing the object. e.g., sorting, based on the detected color/optical properties, for further industrial processing, packaging, etc.) may be desired to have the measurement made with the probe held or positioned substantially stationary above the surface of the object to be measured (in such embodiments, the positioned probe may not be hand-held as with certain other embodiments).

Figure 16:
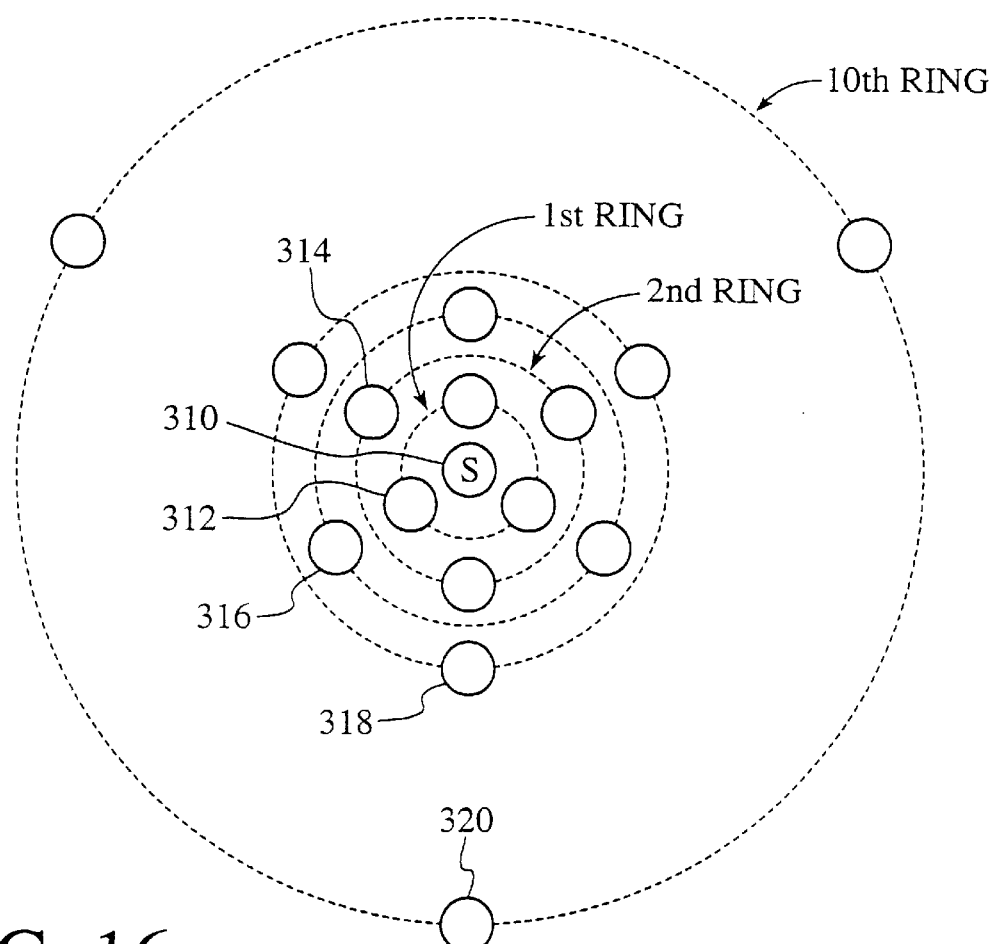
FIG. 16 illustrates an embodiment, which utilizes a plurality of rings light receivers that may be utilized to take measurements with the probe held substantially stationary with respect to the object being measured which may serve to further the understanding of preferred embodiments of the present invention.

FIG. 16 illustrates such a further embodiment. The probe of this embodiment includes a plurality of perimeter sensors and a plurality of color sensors coupled to Receivers 312–320. The color sensors and related components, etc., may be constructed to operate in a manner analogous to previously described embodiments. For example, fiber optic cables or the like may couple light from source 310 that is received by receivers 312–320 to sharp cut-off filters or notch filters, with the received light measured over precisely defined wavelengths (see. e.g.. FIGS. 1, 3 and 11–14 and related description). Color/optical characteristics of the object may be determined from the plurality of color sensor measurements, which may include three such sensors in the case of a tristimulus instrument, or 8, 12, 15 or more color sensors for a more full bandwidth system (the precise number may be determined by the desired color resolution. etc.).

With this embodiment, a relatively greater number of perimeter sensors are utilized (as opposed, for example, to the three perimeter sensors used in certain preferred embodiments of the present invention). As illustrated in FIG. 16, a plurality of triads of receivers 312–320 coupled to perimeter sensors are utilized, where each triad in the preferred implementation consists of three fiber optics positioned equal distance from light source 310, which in the preferred embodiment is a central light source fiber optic. The triads of perimeter receivers/sensors may be configured as concentric rings of sensors around the central light source fiber optic. In FIG. 16, ten such triad rings are illustrated, although in other embodiments a lesser or greater number of triad rings may be utilized, depending upon the desired accuracy and range of operation, as well as cost considerations and the like.

The probe illustrated in FIG. 16 may operate within a range of heights (i.e., distances from the object being measured). As with earlier embodiments, such height characteristics are determined primarily by the geometry and constituent materials of the probe, with the spacing of the minimal ring of perimeter sensors determining the minimal height, and the spacing of the maximal ring of perimeter sensors determining the maximum height, etc. It therefore is possible to construct probes of various height ranges and accuracy, etc., by varying the number of perimeter sensor rings and the range of ring distances from the central source fiber optic. It should be noted that such embodiments may be particularly suitable when measuring similar types of materials, etc.

As described earlier, the light receiver elements for the plurality of receivers/perimeter sensors may be individual elements such as Texas Instruments TSL230 light-to-frequency converters, or may be constructed with rectangular array elements or the like such as may be found in a CCD camera. Other broadband-type of light measuring elements are utilized in other embodiments. Given the large number of perimeter sensors used in such embodiments (such as 30 for the embodiment of FIG. 16), an array such as CCD camera-type sensing elements may be desirable. It should be noted that the absolute intensity levels of light measured by the perimeter sensors is not as critical to such embodiments of the present invention, in such embodiments differences between the triads of perimeter light sensors are advantageously utilized in order to obtain optical measurements.

Optical measurements may be made with such a probe by holding/positioning the probe near the surface of the object being measured (i.e., within the range of acceptable heights of the particular probe). The light source providing light to light source 310 is turned on and the reflected light received by receivers 311–320 (coupled to the perimeter sensors) is measured. The light intensity of the rings of triad sensors is compared. Generally, if the probe is perpendicular to the surface and if the surface is flat, the light intensity of the three sensors of each triad should be approximately equal. If the probe is not perpendicular to the surface or if the surface is not flat, the light intensity of the three sensors within a triad will not be equal. It is thus possible to determine if the probe is perpendicular to the surface being measured. etc. It also is possible to compensate for non-perpendicular surfaces by mathematically adjusting the light intensity measurements of the color sensors with the variance in measurements of the triads of perimeters sensors.

Since the three sensors forming triads of sensors are at different distances (radii) from central light source 310, it is expected that the light intensities measured by light receivers 312–320 and the perimeter sensors will vary. For any given triad of sensors, as the probe is moved closer to the surface, the received light intensity will increase to a maximum and then sharply decrease as the probe is moved closer to the surface. As with previously-described embodiments, the intensity decreases rapidly as the probe is moved less than the peaking height and decreases rapidly to zero or almost zero for opaque objects. The value of the peaking height depends principally upon the distance of the particular receiver from light source 310. Thus, the triads of sensors will peak at different peaking heights. By analyzing the variation in light values received by the triads of sensors, the height of the probe can be determined. Again, this is particularly true when measuring similar types of materials. As discussed earlier, comparisons with previously-stored data also may be utilized to make such determinations or assessments, etc.

The system initially is calibrated against a neutral background (e.g., a gray background), and the calibration values are stored in non-volatile memory (see, e.g., processor 10 of FIG. 1). For any given color or intensity, the intensity for the receivers/perimeter sensors independent of distance from the central source fiber optic) in general should vary equally. Hence, a white surface should produce the highest intensities for the perimeter sensors, and a black surface will produce the lowest intensities. Although the color of the surface will affect the measured light intensities of the perimeter sensors, it should affect them substantially equally. The height of the probe from the surface of the object, however, will affect the triads of sensors differently. At the minimal height range of the probe, the triad of sensors in the smallest ring (those closest to the source fiber optic) will be at or about their maximal value. The rest of the rinds of triads will be measuring light at intensities lower than their maximal values. As the probe is raised/positioned from the minimal height, the intensity of the smallest ring of sensors will decrease and the intensity of the next ring of sensors will increase to a maximal value and will then decrease in intensity as the probe is raised/positioned still further. Similarly for the third ring, fourth ring and so on. Thus, the pattern of intensities measured by the rings of triads will be height dependent. In such embodiments, characteristics of this pattern may be measured and stored in non-volatile RAM look-up tables (or the like) for the probe by calibrating it in a fixture using a neutral color surface. Again, the actual intensity of light is not as important in such embodiments, but the degree of variance from one ring of perimeter sensors to another is.

To determine a measure of the height of the probe from the surface being measured, the intensities of the perimeter sensors (coupled to receivers 312–320) is measured. The variance in light intensity from the inner ring of perimeter sensors to the next ring and so on is analyzed and compared to the values in the look-up table to determine the height of the probe. The determined height of the probe with respect to the surface thus may be utilized by the system processor to compensate for the light intensities measured by the color sensors in order to obtain reflectivity readings that are in general independent of height. As with previously described embodiments, the reflectivity measurements may then be used to determine optical characteristics of the object being measured, etc.

It should be noted that audio tones, such as previously described, may be advantageously employed when such an embodiment is used in a handheld configuration. For example, audio tones of varying pulses, frequencies and/or intensities may be employed to indicate the operational status of the instrument, when the instrument is positioned within an acceptable range for color measurements, when valid or invalid color measurements have been taken, etc. In general, audio tones as previously described may be adapted for advantageous use with such further embodiments.

Figure 17:
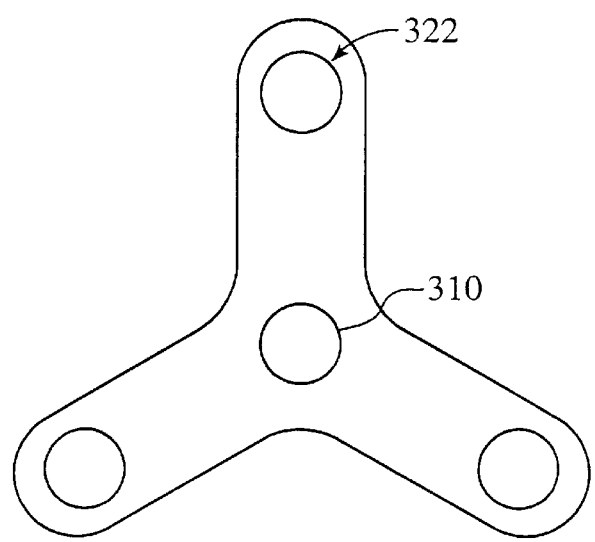
FIGS. 17 and 18 illustrate an embodiment, which utilizes a mechanical movement and also may be utilized to take measurements with the probe held substantially stationary with respect to the object being measured, which may serve to further the understanding of preferred embodiments of the present invention.

FIG. 17 illustrates a further such embodiment of the present invention. The preferred implementation of this embodiment consists of a central light source 310 (which in the preferred implementation is a central light source fiber optic), surrounded by a plurality of light receivers 322 (which in the preferred implementation consists of three perimeter light receiver fiber optics). The three perimeter light receiver fiber optics, as with earlier described embodiments, may be each spliced into additional fiber optics that pass to light intensity receivers/sensors, which may be implemented with Texas Instruments TSL230 light to frequency converters as described previously. One fiber of each perimeter receiver is coupled to a sensor and measured full band width (or over substantially the same bandwidth) such as via a neutral density filter, and other of the fibers of the perimeter receivers are coupled to sensors so that the light passes through sharp cut off or notch filters to measure the light intensity over distinct, frequency ranges of light (again, as with earlier described embodiments). Thus there are color light sensors and neutral "perimeter" sensors as with previously described embodiments. The color sensors are utilized to determine the color or other optical characteristics of the object, and the perimeter sensors are utilized to determine if the probe is perpendicular to the surface and/or are utilized to compensate for non-perpendicular angles within certain angular ranges.

In the embodiment of FIG. 17, the angle of the perimeter sensor fiber optics is mechanically varied with respect to the central source fiber optic. The angle of the perimeter receivers/sensors with respect to the central source fiber optic is measured and utilized as described hereinafter. An exemplary mechanical mechanism, the details of which are not critical so long as desired, control movement of the perimeter receivers with respect to the light source is obtained, is described with reference to FIG. 18.

The probe is held within the useful range of the instrument (determined by the particular configuration and construction, etc.), and a color measurement is initiated. The angle of the perimeter receivers/sensors with respect to the central light source is varied from parallel to pointing towards the central source fiber optic. While the angle is being varied, the intensities of the light sensors for the perimeter sensors (e.g., neutral sensors) and the color sensors is measured and saved along with the angle of the sensors at the time of the light measurement. The light intensities are measured over a range of angles. As the angle is increased the light intensity will increase to a maximum value and will then decrease as the angle is further increased. The angle where the light values is a maximum is utilized to determine the height of the probe from the surface. As will be apparent to those skilled in the art based on the teachings provided herein, with suitable calibration data, simple geometry or other math. etc., may be utilized to calculate the height based on the data measured during variation of the angle. The height measurement may then be utilized to compensate for the intensity of the color/optical measurements and/or utilized to normalize color values, etc.

Figure 18:
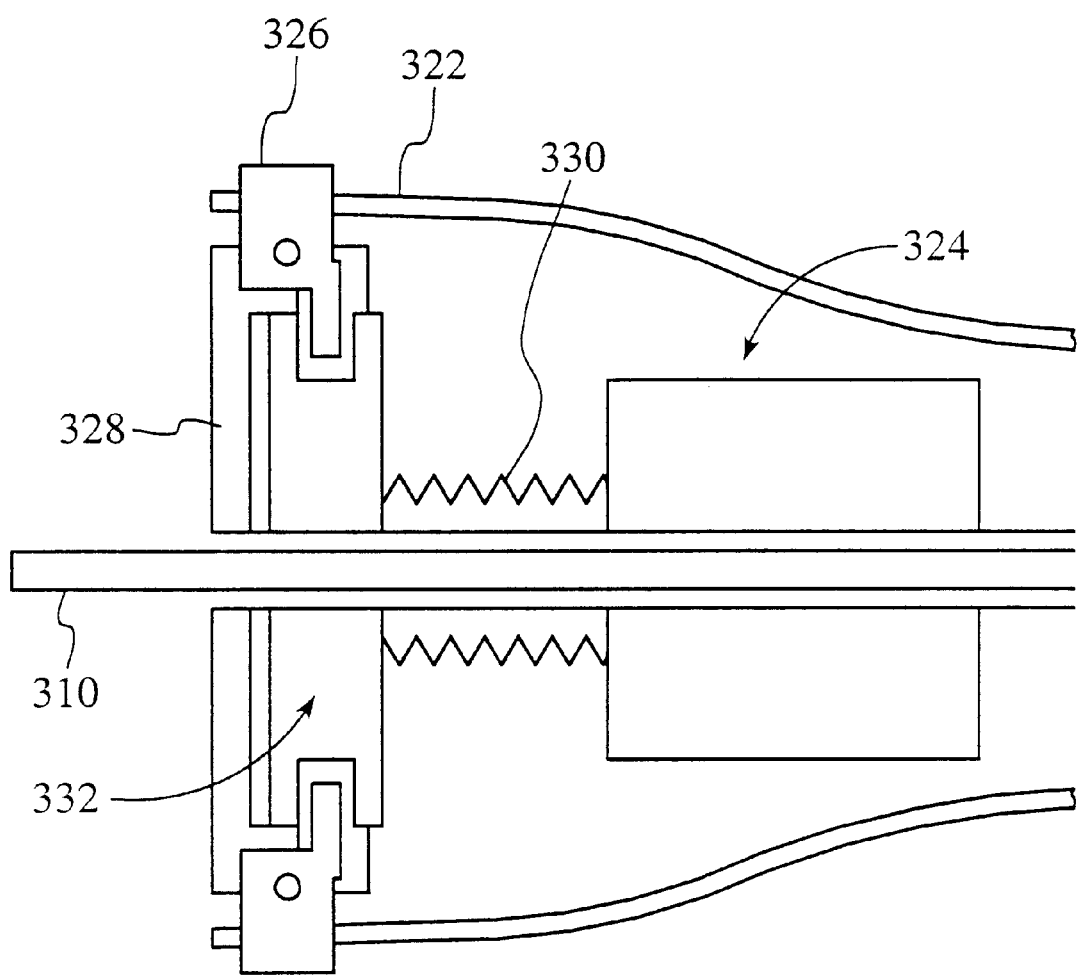

FIG. 18 illustrates an exemplary embodiment of a mechanical arrangement to adjust and measure the angle of the perimeter sensors. Each perimeter receiver/sensor 322 is mounted with pivot arm 326 on probe frame 328. Pivot arm 326 engages central ring 332 in a manner to form a cam mechanism. Central ring 332 includes a groove that holds a portion of pivot arm 326 to form the cam mechanism. Central ring 339 may be moved perpendicular with respect to probe frame 328 via linear actuator 324 and threaded spindle 330. The position of central ring 332 with respect to linear actuator 324 determines the angle of perimeter receivers/sensors 322 with respect to light source 310. Such angular position data vis-à-vis the position of linear actuator 324 may be calibrated in advance and stored in non-volatile memory, and later used to produce color/optical characteristic measurement data as previously described.

With the foregoing as background, various additional preferred embodiments utilizing variable aperture receivers in order to measure, for example, the degree of gloss of the surface will now be described with references to FIGS. 20A to 22B. Various of the electronics and spectrophotometer/reflectometer implements described above will be applicable to such preferred embodiments.

Figure 20A:
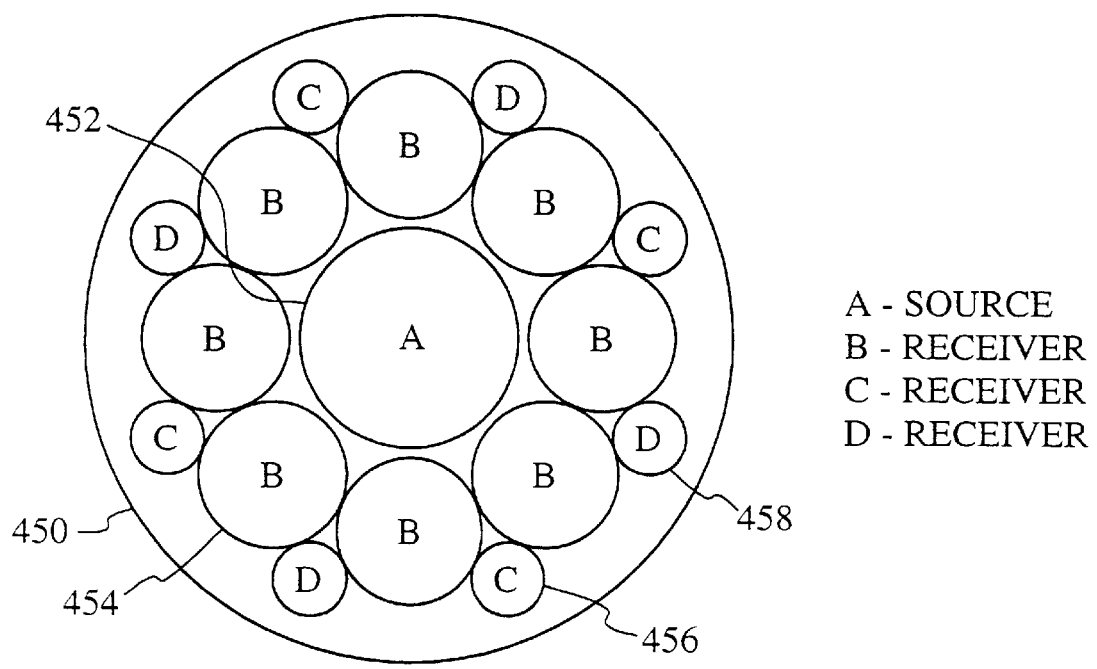
FIGS. 20A and 20B illustrate cross sections of probes that may be used in accordance with preferred embodiments of the present invention.

Referring to FIG. 20A, a probe utilizing variable aperture receivers will nosy be described. In FIG. 20A, source A 452 represents a source fiber optic of a small numerical aperture NA, 0.25 for example; receivers B 454 represent receiver fiber optics of a wider numerical aperture, 0.5 for example; receivers C 456 represent receiver fiber optics of the same numerical aperture as source A but is shown with a smaller core diameter; and receivers D 458 represent receiver fiber optics of a wider numerical aperture. 0.5 for example.

One or more of receiver(s) B 454 (in certain embodiments one receiver B may be utilized, while in other embodiments a plurality of receivers B are utilized, which may be circularly arranged around source A, such as 6 or 8 such receivers B) pass to a spectrometer (see, e.g., FIGS. 1, 3, 11, 12, configured as appropriate for such preferred embodiments). Receivers B 454 are used to measure the spectrum of the reflected light. Receivers C 456 and D 458 pass to broad band (wavelength) optical receivers and are used to correct the measurement made by receiver(s) B. Receivers C 456 and D 458 are used to correct for and to detect whether or not the probe is perpendicular to the surface and to measure/assess the degree of specular versus diffuse reflection (the coefficient of specular reflection. etc.) and to measure the translucency of the material/object.

Figure 20B:
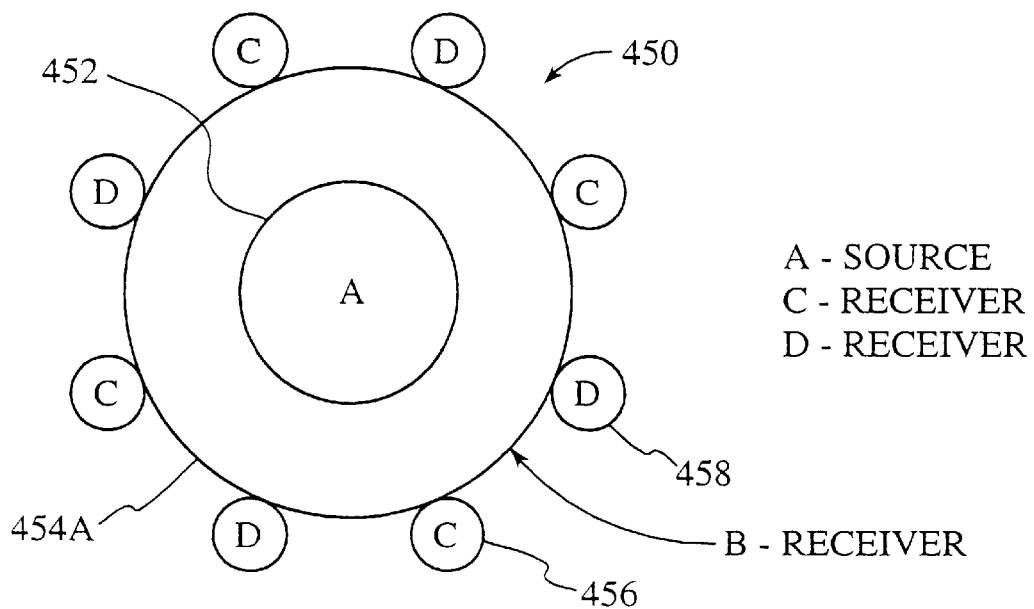

FIG. 20B illustrates a refinement of the embodiment of FIG. 20A, in which receivers B 454 are replaced by a cylindrical arrangement of closely packed, fine optical fibers 454A, which generally surround light source 452 as illustrated. The fibers forming the cylindrical arrangement for receivers B 454A, are divided into smaller groups of fibers and are presented, for example, to light sensors 8 shown in FIG. 1. The number of groups of fibers is determined by the number of light sensors. Alternately, the entire bundle of receiver fibers B 454A is presented to a spectrometer such as a diffraction grating spectrometer of conventional design. As previously described, receivers C 456 and D 458 may be arranged on the periphery thereof. In certain embodiments, receivers C and D may also consist of bundles of closely packed, fine optical fibers. In other embodiments they consist of single fiber optics.

The assessment of translucency in accordance with embodiments of the present invention have already been described. It should be noted, however, that in accordance with the preferred embodiment both the light reflected from the surface of the material/object (i.e., the peaking intensity) and its associated spectrum and the spectrum of the light when it is in contact with the surface of the material/object may be measured/assessed. The two spectrums typically will differ in amplitude (the intensity or luminance typically will be greater above the surface than in contact with the surface) and the spectrums for certain materials may differ in chrominance (i.e., the structure of the spectrum) as well.

When a probe in accordance with such embodiments measures the peaking intensity, it in general is measuring both the light reflected from the surface and light that penetrates the surface, gets bulk scattered within the material and re-emerges from the material (e.g., the result of translucency). When the probe is in contact with the surface (e.g., less than the critical height), no light reflecting from the surface can be detected by the receiver fiber optics, and thus any light detected by the receivers is a result of the translucency of the material and its spectrum is the result of scattering within the bulk of the material. The "reflected spectrum" and the "bulk spectrums" in general may be different for different materials, and assessments of such reflected and bulk spectrum provide additional parameters for measuring, assessing and/or characterizing materials, surfaces, objects, teeth, etc., and provide new mechanisms to distinguish Translucent and other topes of materials.

In accordance with preferred embodiments of the present invention, an assessment or measurement of the degree of gloss (or specular reflection) may be made. For understanding thereof, reference is made to FIGS. 21 to 22B.

Figure 21:
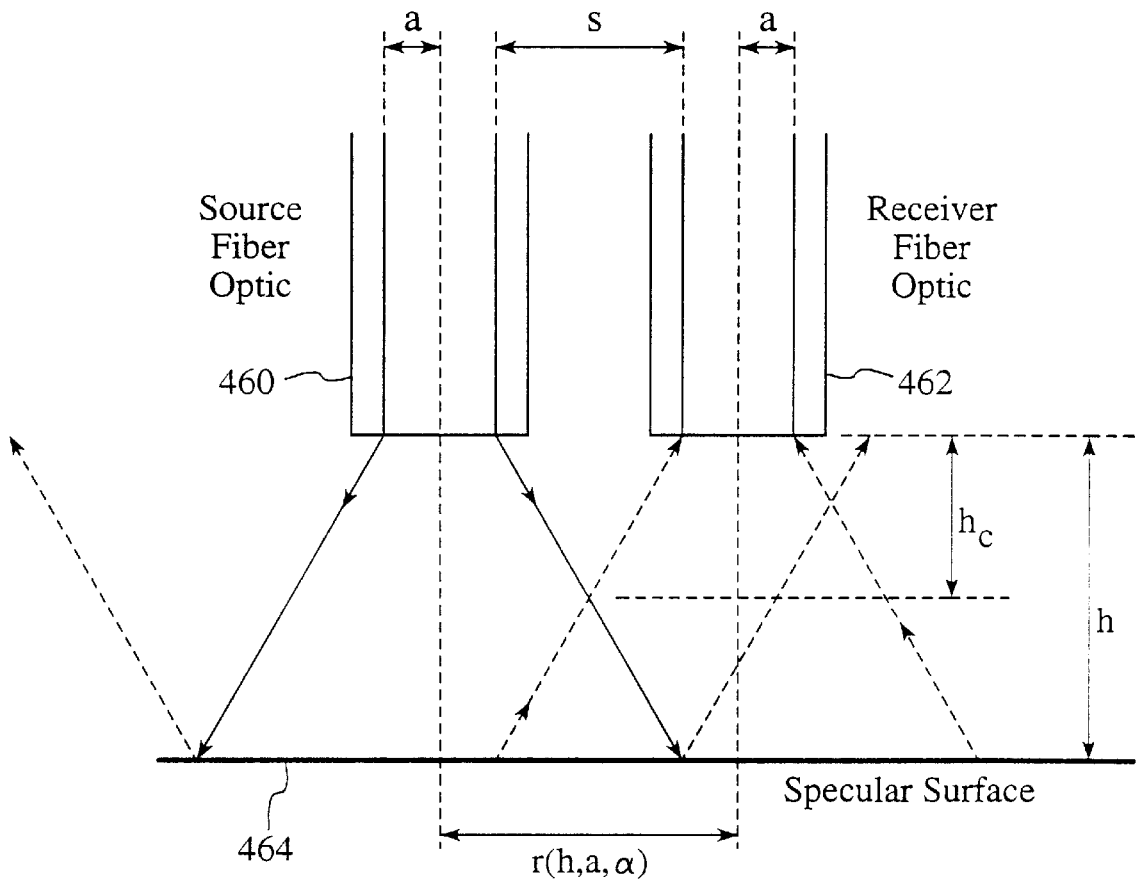
FIGS. 21 and 22A and 22B illustrate certain geometric and other properties of fiber optics for purposes of understanding certain preferred embodiments.

Referring to FIG. 21, consider two fiber optics, source fiber optic 460 and receiver fiber optic 462, arranged perpendicular to a specular surface as illustrated. The light reflecting from a purely specular surface will be reflected in the form of a cone. As long as the numerical aperture of the receiver fiber optic is greater than or equal to the numerical aperture of the source fiber optic, all the light reflected from the surface that strikes the receiver fiber optic will be within the receiver fiber optic's acceptance cone and will be detected. In general, it does not matter what the numerical aperture of the receiver fiber optic is, so long, as it is greater than or equal to the numerical aperture of the source fiber optic. When the fiber optic pair is far from the surface, receiver fiber optic 462 is fully illuminated. Eventually, as the pair approaches surface 464, receiver fiber optic 462 is only partially illuminated. Eventually, at heights less than or equal to the critical height $h_c$ receiver fiber optic 462 will not be illuminated. In general, such as for purely specular surfaces, it should be noted that the critical height is a function of the numerical aperture of source fiber optic 460, and is not a function of the numerical aperture of the receiver.

Figure 22A:
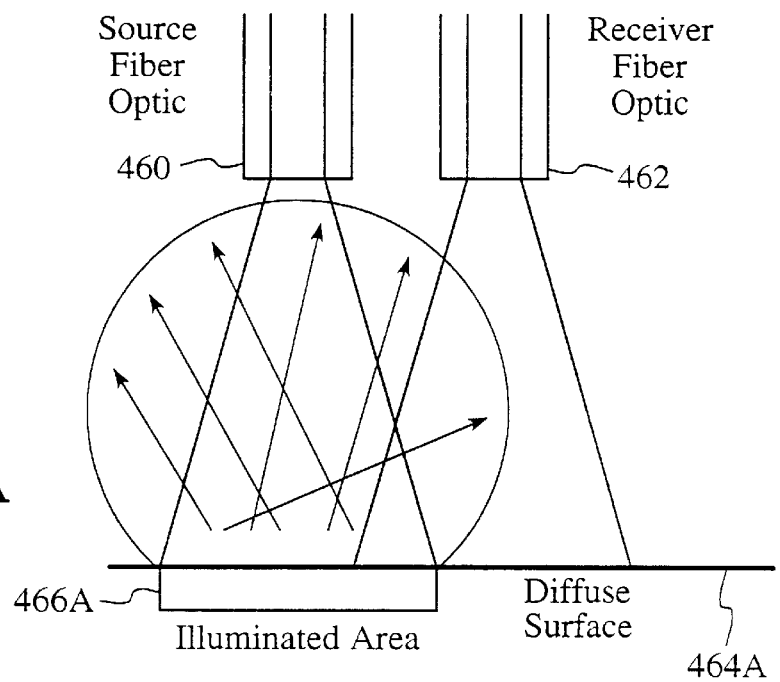
Figure 22B:
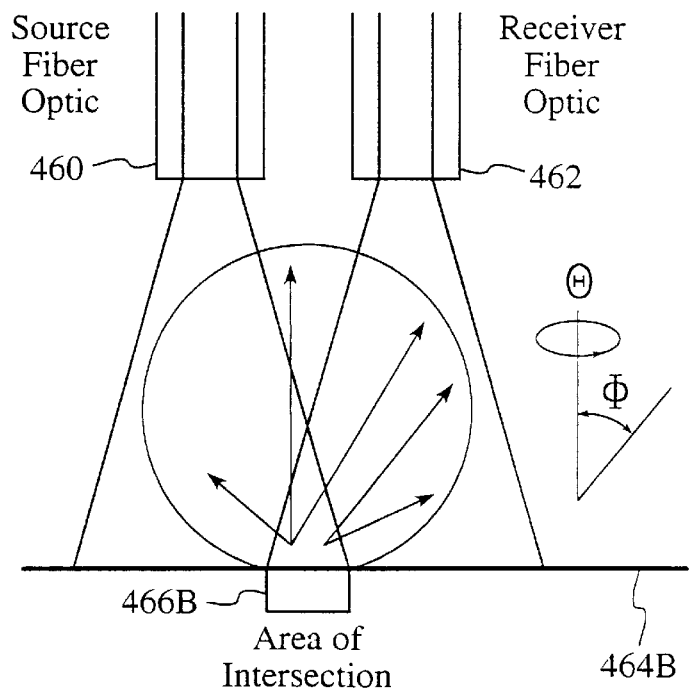

Referring now to FIGS. 22A and 22B, consider two fiber optics (source 460 and receiver 462) perpendicular to diffuse surface 464A as illustrated in FIG. 22A (FIG. 22B depicts mixed specular/diffuse surface 464B and area of intersection 466B). Source fiber optic 460 illuminates circular area 466A on surface 464A, and the light is reflected from surface 464A. The light, however, will be reflected at all angles, unlike a specular surface where the light will only be reflected in the form of a cone. Receiver fiber optic 462 in general is always illuminated at all heights, although it can only propagate and detect light that strikes its surface at an angle less than or equal to its acceptance angle. Thus, when the fiber optic pair is less than the critical height, receiver fiber optic 462 detects no light. As the height increases above the critical height, receiver fiber optic 462 starts to detect light that originates from the area of intersection of the source and receiver cones as illustrated. Although light may be incident upon receiver fiber optic 462 from other areas of the illuminated circle, it is not detected because it is greater than the acceptance angle of the receiver fiber.

As the numerical aperture of receiver fiber optic 462 increases, the intensity detected by receiver fiber optic 462 will increase for diffuse surfaces, unlike a specular surface where the received intensity is not a function of receiver fiber optic numerical aperture. Thus, for a probe constructed with a plurality of receiver fiber optics with different numerical apertures, as in preferred embodiments of the present invention, if the surface is a highly glossy surface, both receivers (see. e.g., receivers 456 and 458 of FIG. 20A, will measure the same light intensity. As the surface becomes increasingly diffuse, however receiver D 458 will have a greater intensity than receiver C 456. The ratio of the two intensities from receivers C/D is a measure of, or correlates to, the decree of specular reflection of the material, and may be directly or indirectly used to quantify the "glossiness" of the surface. Additionally, it should be noted that generally receiver C 456 (preferably having the same numerical aperture as source fiber optic A 452) measures principally the specular reflected component. Receiver D 458, on the other hand, generally measures both diffuse and specular components. As will be appreciated by those skilled in the art, such probes and methods utilizing receivers of different/varying numerical apertures may be advantageously utilized, with or without additional optical characteristic determinations as described elsewhere herein, to further quantify materials such as teeth or other objects.

Figure 23A:
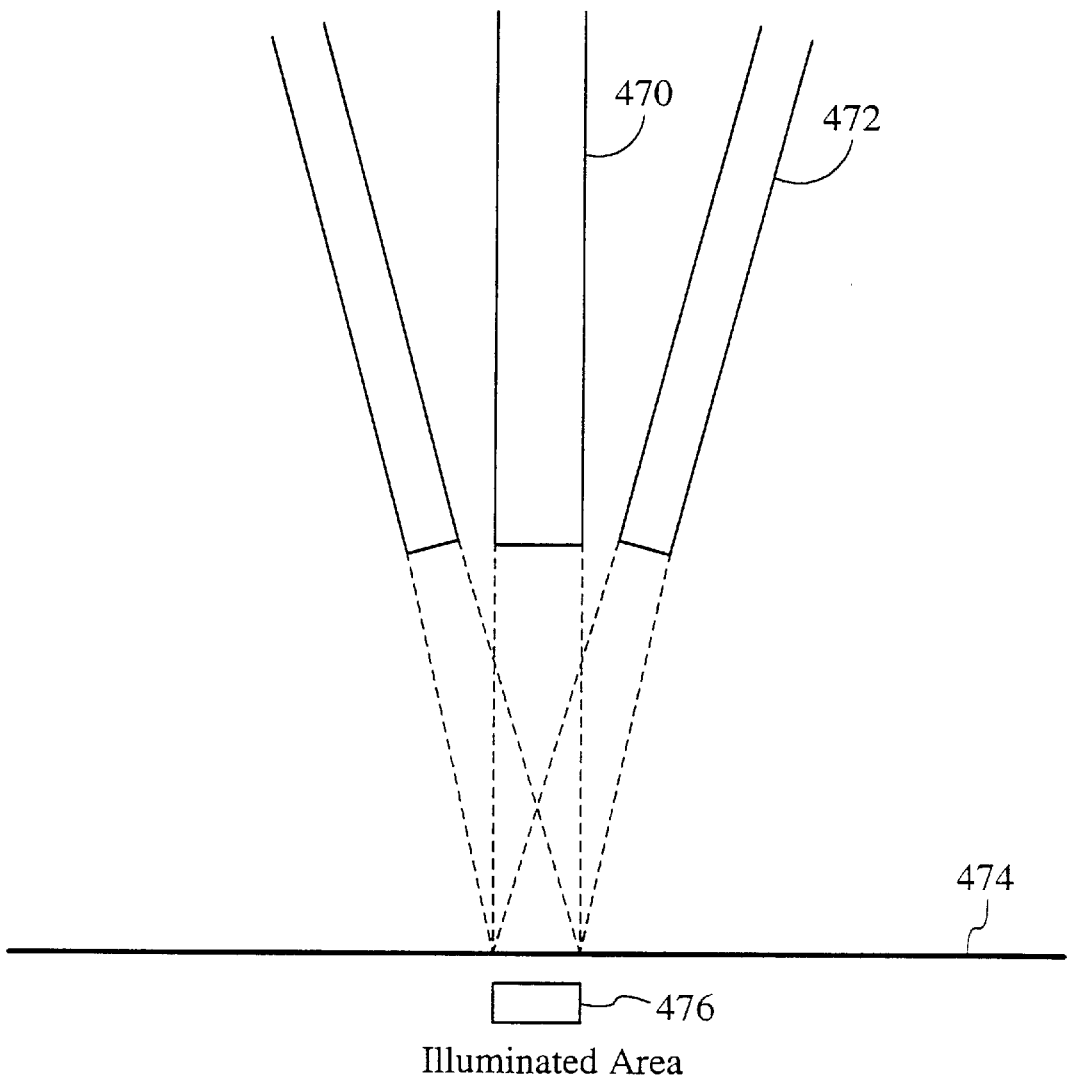
FIGS. 23A and 23B illustrate probes for measuring "specular-excluded" type spectrums in accordance with the present invention.

Referring now to FIG. 23A, additional preferred embodiments will be described. The embodiment of FIG. 23A utilizes very narrow numerical aperture, non-parallel fiber optic receivers 472 and very narrow numerical aperture source fiber optic 470 or utilizes other optical elements to create collimated or nearly collimated source and receiver elements. Central source fiber optic 470 is a narrow numerical aperture fiber optic and receiver fiber optics 472 as illustrated (preferably more than two such receivers are utilized in such embodiments) are also narrow fiber optics. Other receiver fiber optics may be wide numerical aperture fiber optics (e.g., receivers such as receivers 458 of FIG. 20A). As illustrated, receiver fiber optics 4° of such embodiments are at an angle with respect to source fiber optic 470, with the numerical aperture of the receiver fiber optics selected such that, when the received intensity peals as the probe is lowered to the surface, the receiver fiber optics' acceptance cones intersect with the entire circular area illuminated by the source fiber optic, or at least with a substantial portion of the area illuminated by the source. Thus, the receivers generally are measuring the same central spot illuminated by the source fiber optic.

Figure 23B:
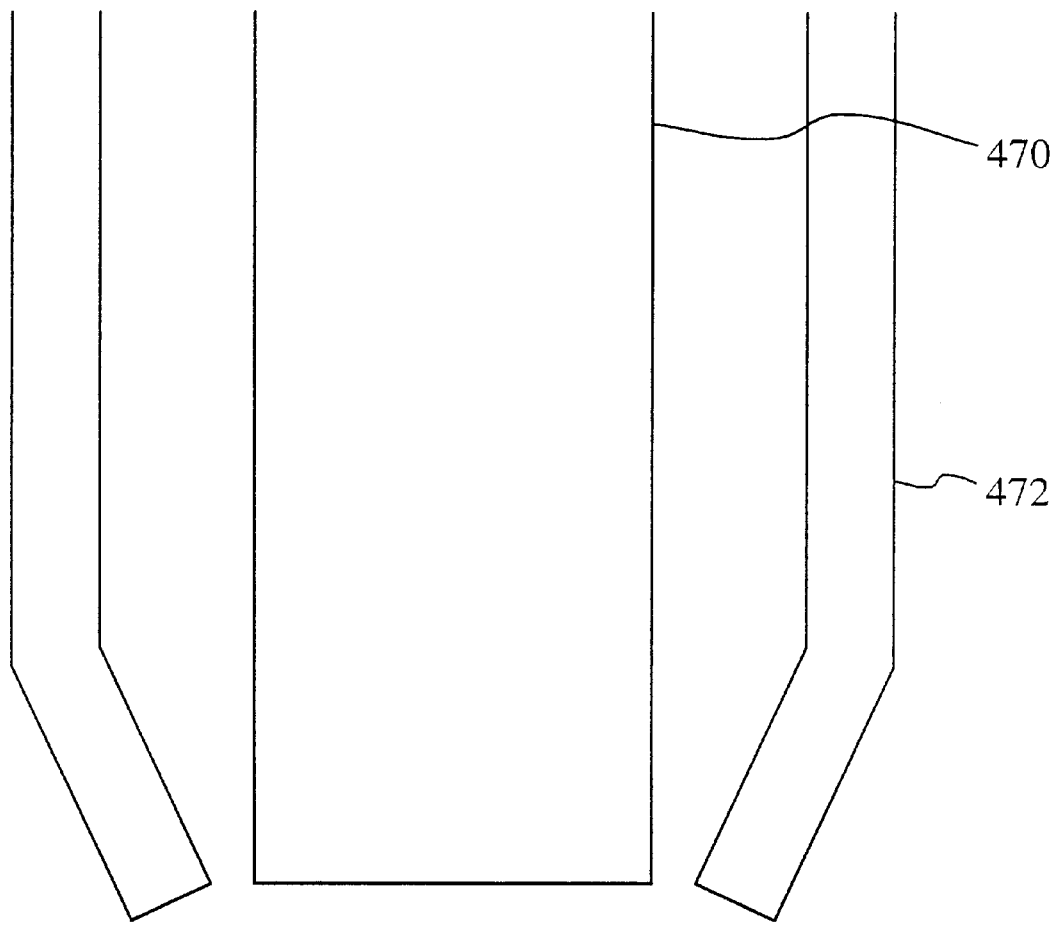
Figure 24:
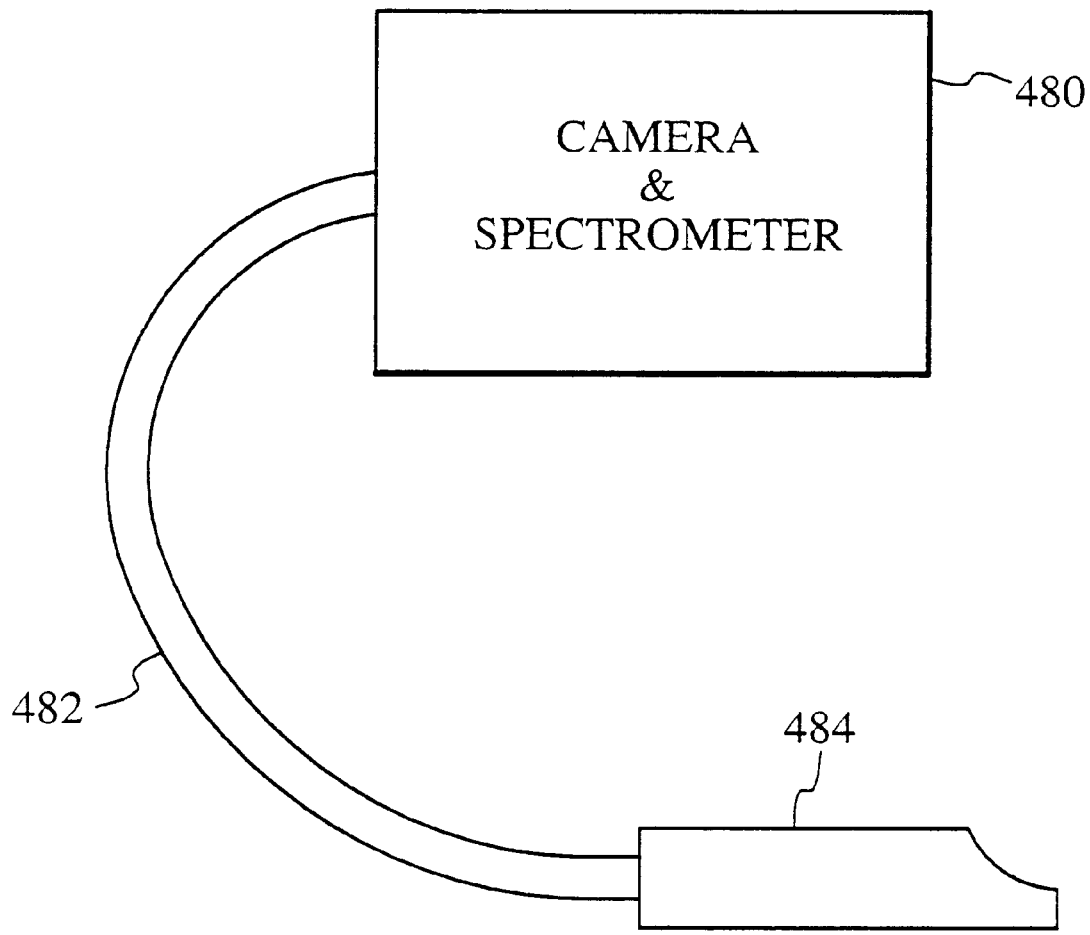
FIGS. 24, 25, and 26 illustrate embodiments in which cameras and reflectometer type instruments in accordance with the present invention are integrated.
Figure 25:
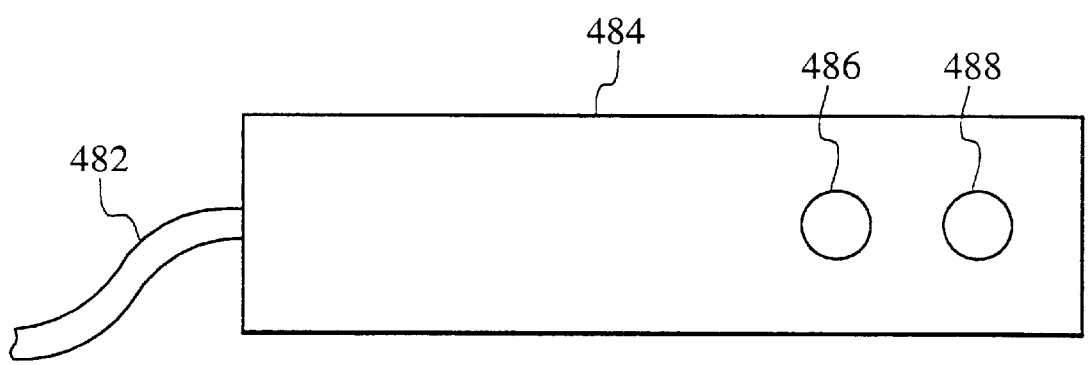
Figure 26:
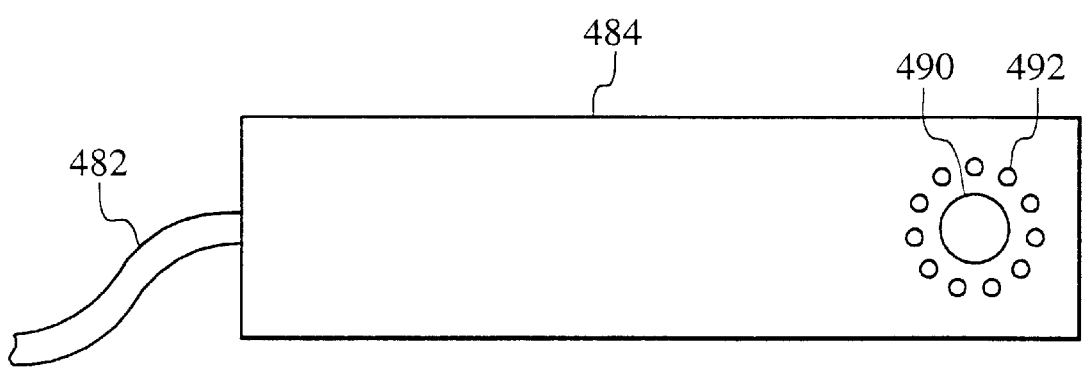

A particular aspect of such embodiments is that a specular excluded probe/measurement technique may be provided. In general, the spectrally reflected light is not incident upon the X receiver fiber optics, and thus the probe is only sensitive to diffuse light. Such embodiments may be useful for coupling reflected light to a multi-band spectrometer (such as described previously) or to more wide band sensors. Additionally, such embodiments may be useful as a part of a probe/measurement technique utilizing both specular included and specular excluded sensors. An illustrative arrangement utilizing such an arrangement is shown in FIG. 2B. In FIG. 23B, element 470 may consist of a source fiber optic, or alternatively may consist of all or part of the elements shown in cross-section in FIG. 20A or 20B. Still alternatively, non-parallel receiver fiber optics 472 may be parallel along their length but have a machined, polished, or other finished or other bent surface on the end thereof in order to exclude all, or a substantial or significant portion, of the specularly reflected light. In other embodiments, receiver fiber optics 472 may contain optical elements which exclude specularly reflected light. An additional aspect of embodiments of the present invention-is that they may be more fully integrated with a camera. Referring now to FIGS. 24 to 26, various of such embodiments will be described for illustrative purposes. In such embodiments, optical characteristic measurement implements such as previously described may be more closely integrated with a camera, including common chassis 480, common cord or cable 482, and common probe 484. In one such alternative preferred embodiment, camera optics 486 are positioned adjacent to spectrometer optics 488 near the end of probe 484, such as illustrated in FIG. 25. Spectrometer optics 488 may incorporate, for example, elements of color and other optical characteristics measuring embodiments described elsewhere herein, such as shown in FIGS. 1–3, 9–10B. 11—11, 16–17,. 20A. 20B and 23A and 23B. In another embodiment, camera optics and lamp/light source 490 is positioned near the end of probe 484, around which are positioned a plurality of light receivers 492. Camera optics and lamp/light source 490 provide illumination and optics for the camera sensing element and a light source for making color/optical characteristics in accordance with techniques described elsewhere herein. It should be noted that light receivers 492 are shown as a single ring for illustrative purposes, although in other embodiments light receivers such as described elsewhere herein (such as in the above-listed embodiments including multiple rings/groups. etc.) may be utilized in an analogous manner. Principles of such camera optics generally are known in the borescope or endoscopes fields.

With respect to such embodiments, one instrument may be utilized for both camera uses and for quantifying the optical properties of teeth. The camera may be utilized for showing patients the general state of the tooth, teeth or other dental health, or for measuring certain properties of teeth or dental structure such as size and esthetics or for color postureization as previously described. The optical characteristic measuring implement may then measure the optical properties of the teeth such as previously described herein. In certain embodiments, such as illustrated in FIGS. 25 and 26, a protective shield is placed over the camera for use in a conventional manner, and the protective shield is removed and a specialized tip is inserted into spectrometer optics 488 or over camera optics and lamp/light source 490 and light receivers 492 (such tips may be as discussed in connection with FIGS. 23A–23C, with a suitable securing mechanism) for infection control, thereby facilitating measuring and quantifying the optical properties. In other embodiments a common protective shield (preferably thin and tightly fitted. and optically transparent, such as are known for cameras) that covers both the camera portion and spectrometer portion are utilized.

Based on the foregoing embodiments, with which translucency and gloss may be measured or assessed, further aspects of the present invention will be described. As previously discussed, when light strikes an object, it may be reflected from the surface, absorbed by the bulk of the material, or it may penetrate into the material and either be emitted from the surface or pass entirely through the material (i.e., the result of translucency). Light reflected from the surface may be either reflected specularly (i.e., the angle of reflection equals the angle of incidence), or it may be reflected diffusely (i.e., light may be reflected at any angle). When light is reflected from a specular surface, the reflected light tends to be concentrated. When it is reflected from a diffuse surface, the light tends to be distributed over an entire solid hemisphere (assuming the surface is planar) (see, e.g., FIGS. 29–30B). Accordingly, if the receivers of such embodiment measure only diffusely reflected light, the light spectrum (integrated spectrum or gray scale) will be less than an instrument that measures both the specular and diffusely reflected light. Instruments that measure both the specular and diffuse components may be referred to as "specular included" instruments, while those that measure only the diffuse component may be referred to as "specular excluded."

An instrument that can distinguish and quantify the degree of gloss or the ratio of specular to diffusely reflected light, such as with embodiments previously described, may be utilized in accordance with the present invention to correct and/or normalize a measured color spectrum to that of a standardized surface of the same color, such as a purely diffuse or Lambertian surface. As will be apparent to one of skill in the art, this may be done, for example, by utilizing the gloss measurement to reduce the value or luminance of the color spectrum the overall intensity of the spectrum) to that of the perfectly diffuse material.

A material that is translucent, on the other hand, tends to lower the intensity of the color spectrum of light reflected from the surface of the material. Thus, when measuring the color of a translucent material, the measured spectrum may appear darker than a similar colored material that is opaque. With translucency measurements made as previously described, such translucency measurements may be used to adjust the measured color spectrum to that of a similar colored material that is opaque. As will be understood, in accordance with the present invention the measured color spectrum may be adjusted, corrected or normalized based on such gloss and/or translucency data, with the resulting data utilized, for example, for prosthesis preparation or other industrial utilization as described elsewhere herein.

Additional aspects of the present invention relating to the output of optical properties to a dental laboratory for prosthesis preparation will now be described. There are many methods for quantifying color, including CIELab notation, Munsell notation, shade tab values. etc. Typically, the color of a tooth is reported by a dentist to the lab in the form of a shade tab value. The nomenclature of the shade tab or its value is an arbitrary number assigned to a particular standardized shade guide. Dentists typically obtain the shade tabs from shade tab suppliers. The labs utilize the shade tabs values in porcelain recipes to obtain the final color of the dental prosthesis.

Unfortunately, however, there are variances in the color of shade tabs, and there are variances in the color of batches of dental prosthesis ceramics or other materials. Thus, there are variances in the ceramics/material recipes to obtain a final color of a tooth resulting in a prosthesis that does not match the neighboring teeth.

In accordance with the present invention, such problems may be addressed as follows. A dental lab may receive a new batch of ceramic materials and produce a test batch of materials covering desired color, translucency and/or gloss range(s). The test materials may then be measured, with values assigned to the test materials. The values and associated color, translucency and gloss and other optical properties may then be saved and stored, including into the dental instruments that the lab services (such as by modem download). Thereafter, when a dentist measures the optical properties of a patient's tooth, the output values for the optical properties may be reported to the lab in a formula that is directly related, or more desirably correlated, to the materials that the lab will utilize in order to prepare the prosthesis. Additionally, such functionality may enable the use of "virtual shade guides" or tooth data for customizing or configuring the instrument for the particular application.

Figure 27:
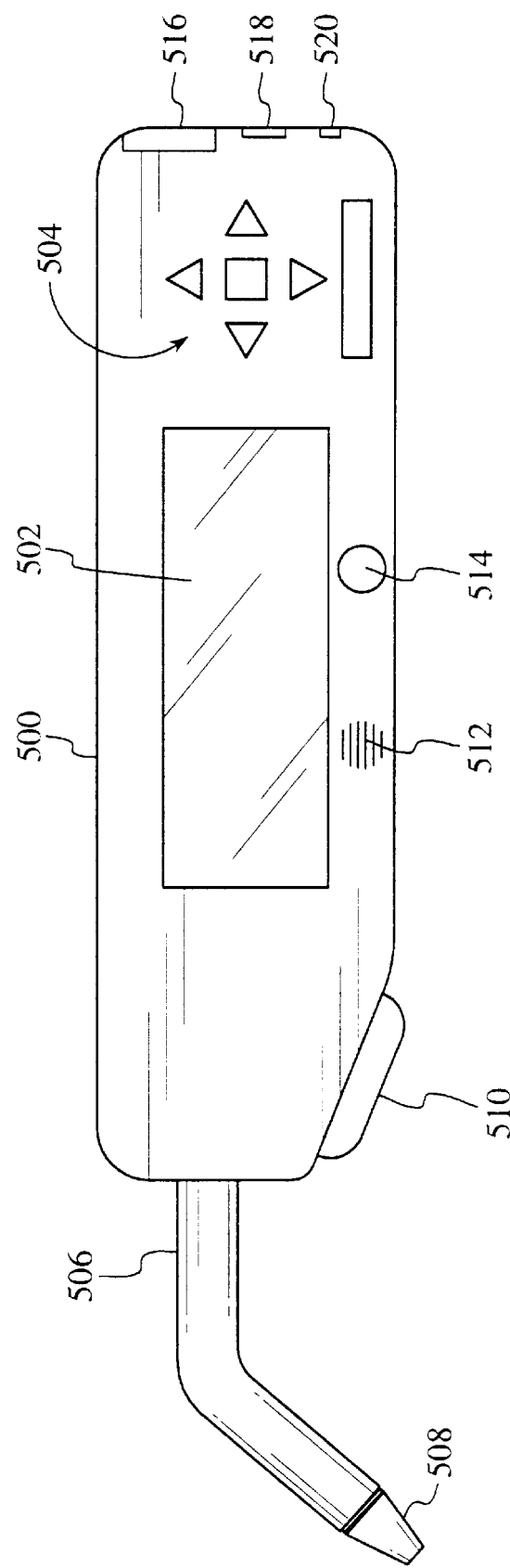
FIGS. 27 and 28 illustrate certain handheld embodiments of the present invention.
Figure 28:
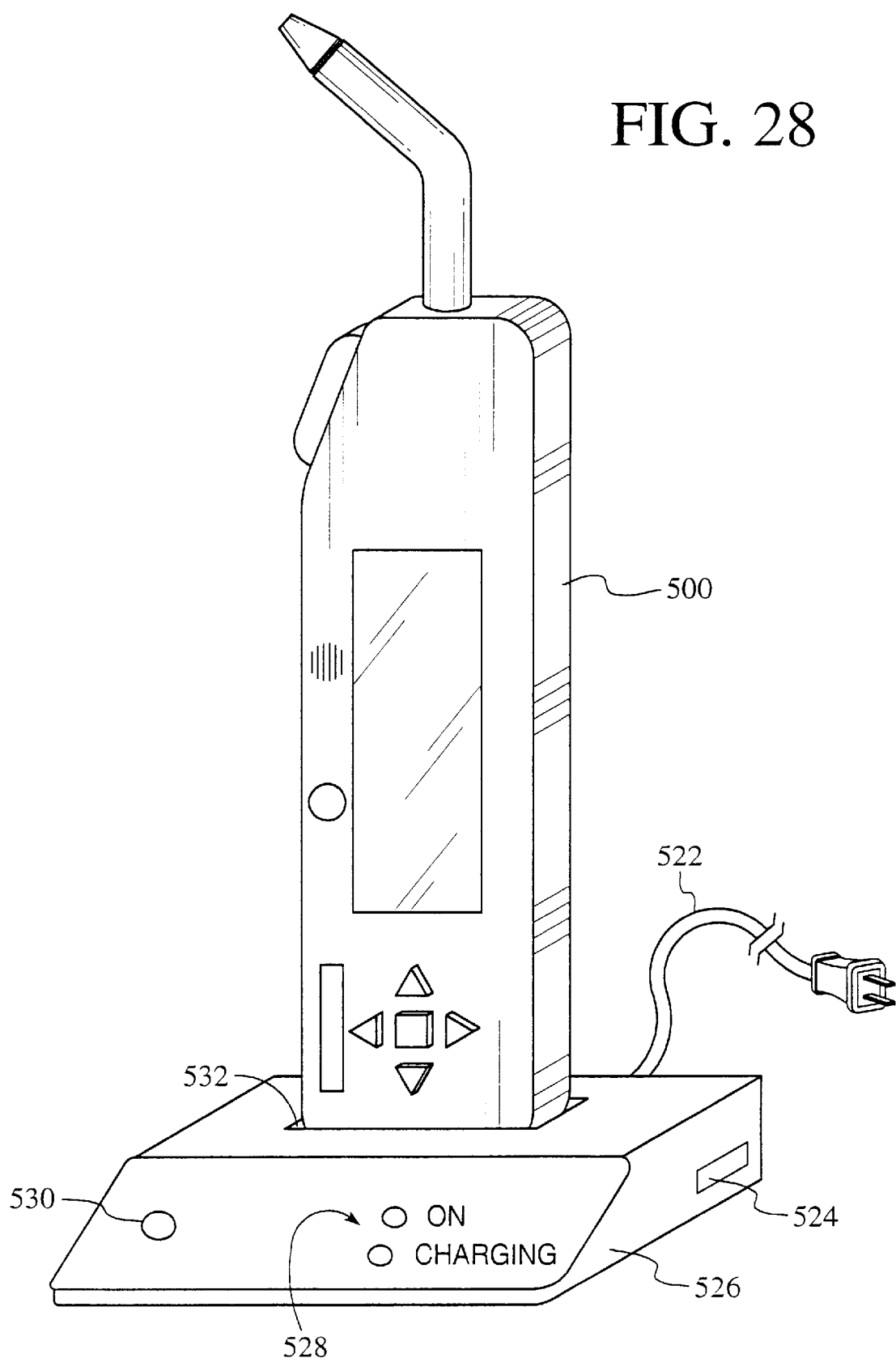

Still other aspects of the present invention will be described with reference to FIGS. 27 and 28, which illustrate a cordless embodiment of the present invention. Cordless unit 500 includes a housing on which is mounted display 502 for display of color/optical property data or status or other information. Keypad 504 is provided to input various commands or information. Unit 500 also may be provided with control switch 510 for initiating measurements or the like, along with speaker 512 for audio feedback (such as previously described), wIreless infrared serial transceiver for wireless data transmission such as to an intelligent charging stand as hereinafter described) and/or to a host computer or the like, battery compartment 516, serial port socket 518 (for conventional serial communications to an intelligent charging stand and/or host computer, and/or battery recharging port 520. Unit 500 includes probe 506, which in preferred embodiments may include removable tip 508 (such as previously described). Of course, unit 500 may contain elements of the various embodiments as previously described herein.

Charging stand 526 preferably includes socket/holder 532 for holding unit 500 while it is being recharged, and preferably includes a socket to connect to wired serial port 518, wireless IR serial transceiver 530, wired serial port 524 (such as an RS232 port) for connection to a host computer (such as previously described), power cable 522 for providing external power to he system, and lamps 528 showing the charging state of the battery and/or other status information or the like.

The system battery may be charred in charring stand 526 in a conventionai manner. A charging indicator (such as lamps 528) may be used to provide an indication of the state of he internal battery. Unit 500 may be removed from the stand, and an optical measurement may be made by the dentist. If the dentist chooses, the optical measurement may be read from display 502, and a prescription may be handwritten or otherwise prepared by the dentist. Alternately, the color/optical characteristics data may be transmitted by wireless IR transceiver 514 (or other cordless system such as RF) to a wireless transceiver, such as transceiver 530 of charging stand 526. The prescription may then be electronically created based upon the color/optical characteristics data. The electronic prescription may be sent from serial port 524 to a computer or modem or other communications channel to the dental laboratory.

Figure 29:
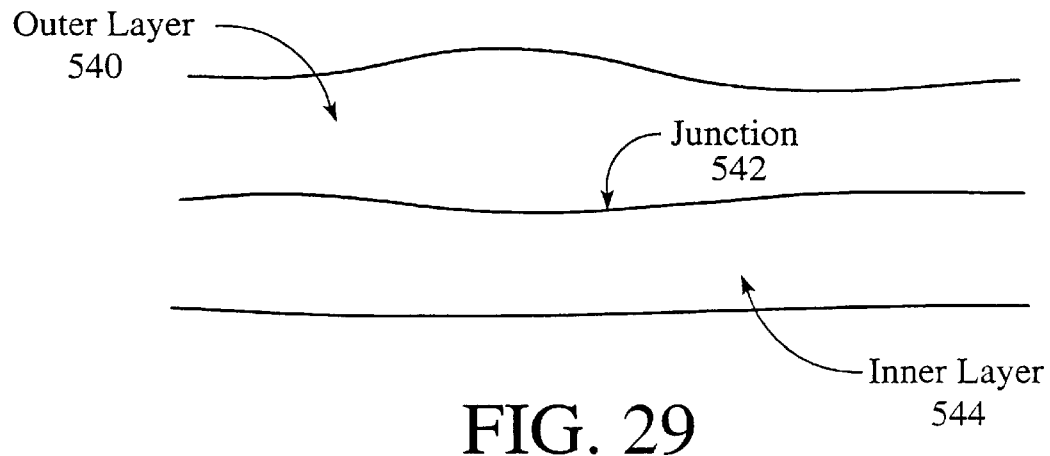
FIG. 29 illustrates an object in cross section, illustrating how embodiments of the present invention may be used to assess subsurface characteristics of various types of objects.

With reference to FIG. 29, additional aspects of the present invention will be discussed.

As is known, certain objects consist of an inner, generally opaque layer, and an outer, generally translucent layer. As previously discussed, light that is incident on a certain object generally can be affected by the object in three ways. First, the light can be reflected from the outer surface of the object, either diffusely or specularly. Second, the light can be internally scattered and absorbed by the object structures. Third, the light can be internally scattered and transmitted through the object structures and re-emerge from the surface of the object. Traditionally, it was difficult, if not impossible, to distinguish light reflected from the surface of the object, whether specularly or diffusely, from light that has penetrated the object, been scattered internally and re-emitted from the object. In accordance with the present invention, however, a differentiation may be made between light that is reflected from the surface or the object and light that is internally scattered and re-emitted from the object.

As previously described, a critical height $h_c$ occurs when a pair of fiber optics serve to illuminate a surface or object and receive light reflected from the surface or object. When the probe's distance from the object's surface is greater than the critical height h, -he receiver fiber optic is receiving light that is both reflected from the object's surface and light that is internally scattered and re-emitted by the object. When the distance of the probe is less than the critical height $h_c$, light that is reflected from the surface of the object no longer can be received by the received fiber optic. In general, the only light that can be accepted by the receiver fiber optic is light that has penetrated outer layer 540 and is re-emitted by the object.

Most of the internal light reflection and absorption within a certain object occurs at junction 542, which in general separates outer layer 540 from inner layer 544. In accordance with the present invention, an apparatus and method may be provided for quantifying optical properties such sub-surface structures, such as the color of junction 542, with or without comparison with data previously taken in order to facilitate the assessment or prediction of such structures.

Critical height $h_c$ of the fiber optic probe such as previously described is a function of the fiber's numerical aperture and the separation between the fibers. Thus, the critical height $h_c$ of the probe can be optimized based on the particular application. In addition, a probe may be constructed with multiple rings of receive fiber optics and/or with multiple numerical aperture receiving fiber optics, thereby facilitating assessment, etc., of outer layer thickness, surface gloss. etc.

By utilizing multiple rings of receiver fiber optics, a measurement of the approximate thickness of the outer layer may be made based on a comparison of the peak intensity above the object surface and a measurement in contact with the object surface. A probe with multiple critical heights will give different intensity levels when in contact with the object surface, thereby producing data that may be indicative of the degree of internal scattering and outer thickness or, object morphology at the point of contact. etc.

Accordingly, in accordance with the present invention, the color or other optical characteristics of a sub-surface structure, such as junction 542 of an object, may be assessed or quantified in a manner that is in general independent of the optical characteristics of the surface of the object, and do so non-invasively, and do so in a manner that may also assess the thickness of the outer layer 540.

Additionally, and to emphasize the wide utility and variability of various of the inventive concepts and techniques disclosed herein, it should be apparent to those skilled in the art in view of the disclosures herein that the apparatus and methodology may be utilized to measure the optical properties of objects using other optical focusing and gathering elements, in addition to the fiber optics employed in preferred embodiments herein. For example, lenses or mirrors or other optical elements may also be utilized to construct both the light source element, and :he light receiver element. A flashlight or other commonly available light source, as particular examples, may be utilized as the light source element, and a common telescope with a photoreceiver may be utilized as the receiver element in a large scale embodiment of the invention. Such refinements utilizing teachings provided herein are expressly within the scope of the present invention.

As will be apparent to those skilled in the art, certain refinements may be made in accordance with the present invention. For example, a central light source fiber optic is utilized in certain preferred embodiments, but other light source arrangements (such as a plurality of light source fibers, etc.). In addition, lookup tables are utilized for various aspects of the present invention, but polynomial type calculations could similarly be employed. Thus, although various preferred embodiments of the present invention have been disclosed for illustrative purposes, those skilled in the art will appreciate that various modifications, additions and/or substitutions are possible without departing from the scope and spirit of the present invention as disclosed in the claims. In addition, while various embodiments utilize light principally in the visible light spectrum, the present invention is not necessarily limited to all or part of such visible light spectrum, and may include radiant energy not within such visible light spectrum.

With reference to FIG. 5A, the intensity measured by a single receiver fiber is shown as a function of time as a source fiber optic and a receiver fiber optic pair are moved into contact with an object and are moved away from the object. FIG. 5A illustrates the intensity as a function of time, however as will be apparent to one skilled in the art, the intensity detected by the receiver fiber can also be measured and plotted as a function of height. A given fiber optic pair of source and receiver fiber optics, perpendicular to a surface (or at least at a fixed angle relative to a surface) will exhibit a certain intensity vs. height relationship. That relationship generally is a constant for certain materials of consistent gloss color and translucency. The mathematical intensity vs. height relationship for certain source and receiver fiber optic pairs can be calculated or measured and stored as a look up table value or as a polynomial or other mathematical relationship. What is important to note is that there is an intensity peak that is a function of the gloss, translucency and color of the object being measured. For similar materials, the intensity value varies dependent upon color, although the shape of the intensity vs. height curve is largely independent of color. Thus, as will be apparent to one skilled in the art, the present invention may also serve as a proximity sensor, determining height from the intensity measurements. The instrument is calibrated by moving it towards the object until the peaking intensity is detected. While the instrument moves towards the object, the light intensities are rapidly measured and saved in memory such as RAM 10 shown in FIG. 1. From the value of the measured peaking intensity (utilized to normalize the intensity vs. height relationship of the fiber pair) the proximity sensor can be calibrated. Thereafter, the present invention may be utilized to measure the height of the fiber optic pair from the surface of the object without contacting the object.

The present invention may find application in a wide range of industrial activities. Certain applications of the present invention include, but are not limited to, measuring the optical properties of teeth and utilizing the measurements as part of a patient data base and utilizing the measurements for dental prosthesis preparation.

Another application of the present invention is its use in dermatology in quantifying the optical properties including color of skin and other tissues and saving the measurements as part of a patient data base record and utilizing the measurements made over a period of time for diagnostic purposes.

Yet another application of the present invention is in the food preparation industry where the color and other optical properties of certain foods that are affected by the preparation process are measured and monitored with the disclosed invention and are utilized to determine whether or not the food meets certain acceptance criteria and where the measurements may be also utilized as part of a control and feed back process whereby the food is further processed until it is either accepted or rejected. Similarly, in an automated food processing like such as for vegetables or fruit, measurements may be taken and an assessment or prediction of the condition of the vegetable or fruit made, such as ripeness.

Yet another application of the present invention is to measure the color and optical properties of objects newly painted as part of a control process. For example, paint may be applied to the object, with the object then measured to determine if a suitable amount or type of paint has been applied, perhaps with the process repeated until a measurement corresponding to a desired surface condition is obtained, etc.

Yet another application of the present invention is to measure the optical properties of newly painted objects over a period of time to discern if the paint has cured or dried. Similarly, such an object may be measured to determine if additional gloss coatings, surface texture factors or fluorescence factors, etc.. should be added to achieve a more optimum or desired object.

Yet another application of the present invention is in an industrial or other control system, where items are color coded or have color or gloss or translucency or combinations of optical properties that identify the objects and where the optical properties are measured utilizing the disclosed invention and are sorted according to their optical properties. In general, the present invention may be utilized to measure the optical properties of objects- an industrial process flow, and then compare such measurements with previously stored data in order to sort, categorize, or control the direction of movement of the object in the industrial process.

Yet another application of the present invention is to place color coded or gloss coated or translucent tags or stickers on objects that serve as inventory control or routine control or other types of identification of objects in industrial processes.

Yet another application of the present invention is part of the printing process to measure and control the color or other optical properties of inks or dies imprinted on materials. In such embodiments, implements as described herein may be integrated into the printer or printing equipment, or used as a separate implement.

Yet another application of the present invention is part of the photographic process to measure, monitor and control the optical properties of the photographic process. In such embodiments, implements as described herein may be integrated into the camera or other photographic instrument, or used as a separate implement.

Yet another application of the present invention is to measure the distance to the surface of objects without being placed into contact with the object.

The present invention may be used in an industrial process in which coatings or material are added to or removed from an object. The object may be measured, and coatings or materials added or removed, with the object re-measured and the process repeated until a desired object or other acceptance criteria are satisfied. In such processes, comparisons with previously stored data may be used to assess whether the desired object is obtained or the acceptance criteria satisfied, etc.

In yet another application, the present invention is utilized in the restoration of paintings or other painted objects, such as art works, automobiles or other objects for which all or part may need to be painted, with the applied paint matching certain existing paint or other criteria. The present invention may be used to characterize whether paint to be applied will match the existing paint. etc. In such processes, comparisons with previously stored data mats be used to assess whether the desired paint match will be obtained. etc.

In general, the present invention may find application in any industrial process in which an object or material may be measured for surface and/or subsurface optical characteristics, with the condition or status of such object or material assessed or predicted based on such measurements, possibly including comparisons with previously stored data as previously described, etc.

Additionally, and to emphasize the wide utility and variability of various of the inventive concepts and techniques disclosed herein, it should be apparent to those skilled in the art in view of the disclosures herein that the apparatus and methodology may be utilized to measure the optical properties of objects using other optical focusing and gathering elements, in addition to the fiber optics employed in preferred embodiments herein. For example, lenses or mirrors or other optical elements may also be utilized to construct both the light source element and the light receiver element. A flashlight or other commonly available light source, as particular examples, may be utilized as the light source element, and a common telescope with a photoreceiver may be utilized as the receiver element in a large scale embodiment of the invention. Such refinements utilizing teachings provided herein are expressly within the scope of the present invention.

Based on the foregoing description, various particular preferred embodiments of the present invention will now be described that relate to detecting and preventing counterfeiting and the like.

Numerous negotiable instruments exist that are created utilizing printing processes or the like. Such negotiable instruments include currency, bonds, stocks, securities, travelers checks, checks, credit cards, passports, and other types of business, legal and/or governmental documents or certificates, etc. In many cases the printing process is highly refined utilizing microprint or other forms of printing that are difficult to reproduce, thereby rendering the instrument, document, or negotiable item difficult to reproduce or to create. Additionally, the item may contain a paper or other backing material difficult to reproduce. In other cases, the item malt contain holographs or other fields making it further difficult to reproduce. In vet other applications, the item may contain inks that have radioactive isotopes, or magnetic qualities, or other properties that are difficult to detect or to reproduce. In yet other applications the item may have strips of materials or certain pigments imbedded internally that are identifiable but difficult to reproduce. In general, numerous methods and methodologies exist or have been proposed that render certain documents or negotiable instruments difficult to reproduce. Such processes however, tend to be inherently difficult to implement, and, indeed, the difficulty in creating the process is the counterfeiting preventive measure.

With optical characteristics determinations made in accordance with the present invention, improved methods of detecting and preventing counterfeiting may be obtained. In accordance with the present invention, layers of pigment or other materials in the printing or similar process may be utilized that render items difficult to reproduce, but relatively easy to create and/or detect.

As previously described, various optical properties of an object may be measured, assessed or predicted in accordance with the present invention. Such optical properties include surface reflection, translucency of surface layers, gloss of the surface and the spectral properties of semi-translucent layers on the surface and of the spectral properties of layers below the surface. Such apparatus and methodologies can be utilized to render printing or similar processes difficult to reproduce.

Figure 30A:
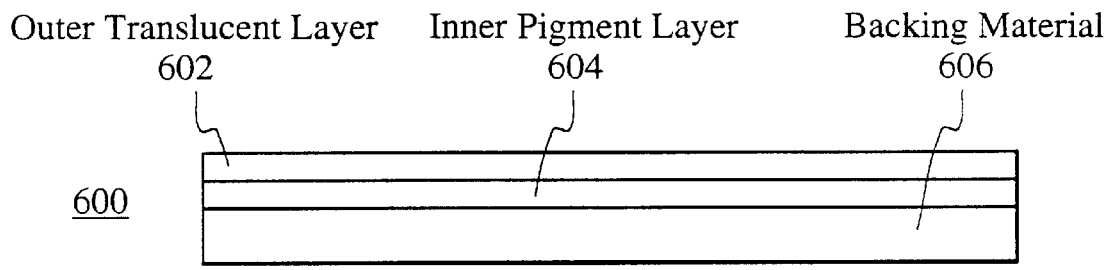
Figure 30B:
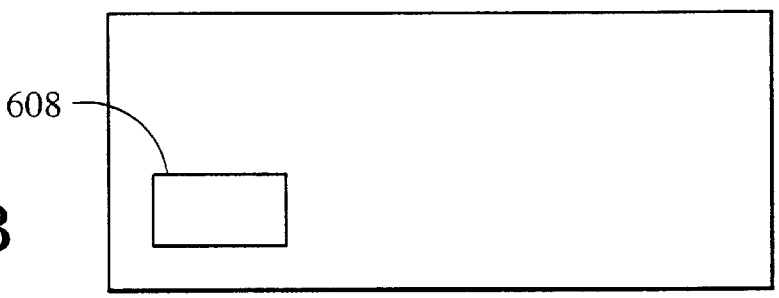
Figure 30C:
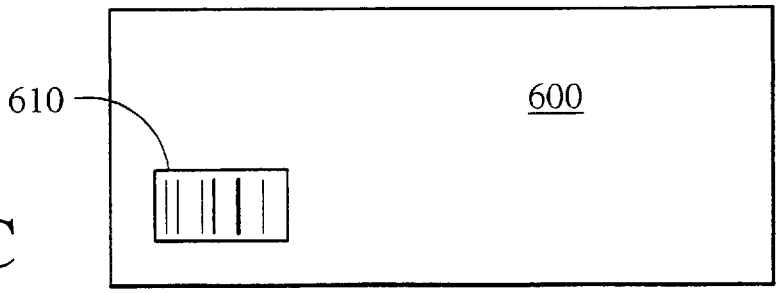

FIGS. 30A to C illustrates instrument 600 (which may be any of the items previously discussed or other items needing counterfeit protection, etc.) that includes a number of layers of pigment or other material. Outer layer or layers (602) generally are semi-transparent or translucent or semi-translucent. Inner layer or layers 604 may be opaque or semi-translucent. The layers are deposited by successively printing pigments (or painting or other deposition or application, etc.) on substrate 606, which may be any suitable backing material, such as paper or plastic or other materials, etc.

If light is reflected from the surface of instrument 600 it in general will exhibit certain optical properties which can be measured by conventional spectrographic or colorimetry techniques. The spectrum of the reflected light will be principally influenced by the surface properties of outer layer(s) 602 and to a lesser degree by inner layer(s) 604 and/or substrate 606, depending upon the degree of translucency of the various layers, etc. If the material is illuminated from the rear, in general the spectral properties of the material will be influenced by all layers of the material, and in general can be quite different from the spectral properties of light reflected from the face of the object.

Preferred embodiments herein provide an instrument and methodology that can distinguish surface reflection properties of an item/material from bulk spectral properties of the item/material, which can be advantageously utilized for preventing/detecting counterfeiting. In such preferred embodiments, an instrument or item document includes substrate 606 printed (or otherwise formed) with inner layer(s) 604 consisting of a relatively long term (depending upon the particular application) stable dye or other pigment or material, and also includes outer layer(s) 602, that preferably consist of a semi-translucent layer printed or otherwise deposited or from inner layer(s) 604. It should be noted that such layer formation may be part of the overall process that forms the instrument or other item, or it may be separate processes that form layers 602 and 604 in a particular location or locations 608 on instrument 600. In certain embodiments, layers 602 and 604 are formed from a fixed or predetermined position from a location marker also included on instrument 600. Such location marker may facilitate the measuring of optical properties of such layers, as will be described, and may provide a further barrier in that the location of the position where optical properties are to be assessed may not be known to an unauthorized person or device, etc.

Following the printing or other formation processes of layers 602 and 604 (and drying or curing, etc.), the optical properties of instrument 600 are quantified including, for example, the surface spectral properties and the spectral properties of the inner layer. Such optical properties may be measured at a single or multiple locations. Such spectral or other optical properties may be recorded and saved such as in a computer data base for future reference. To determine if the document or material is genuine, the spectral properties of instrument 600, and in particular layers 602 and 604, are measured and compared to the previously recorded measurements. Based on such comparisons, which may include a number of acceptance criteria (such as delta E values or other such thresholds or ranges), an assessment or prediction may be made of whether instrument 600 is genuine or counterfeit.

In another such embodiment, inner layer(s) 604 may be printed/formed with different layers of pigments that are changed from batch to batch or periodically, from time to time. The particular pigment for particular instruments may be recorded and stored and may be identified to the particular instruments with a serial number or other form of identification. The pigments of inner and outer layers 602 and 604 may be adjusted in order to insure that the instrument appears to have the same color when visually inspected or when measured with traditional spectrographic or colorimetry techniques. Thus, an entire series of instruments, materials or documents or currency can be printed/formed which visually appear the same, yet have internal or subsurface properties that can be quantified utilizing the apparatus and methodology disclosed elsewhere to uniquely distinguish the documents.

In another such embodiment, inner layer(s) 604 are printed/formed with pattern 610 (see FIG. 30C) such as a pattern utilized in a bar code. The pigments of the inner and outer layers are chosen to render the inner bar codes difficult if not impossible to discern visually by utilizing conventional spectrographic or colorimetry techniques.

In yet another embodiment, inner layer(s) 604 are printed/formed with pattern 610 such as a bar code where the bar code utilizes not only differences in the widths of the lines of the bars as a method of storing data in the pattern, but also where the bars themselves are of different pigments. In such applications, data for the bar code can be encoded in the bars themselves and in the color of the bars. If the material is layered as disclosed above, the bar data is difficult if not impossible to discern, rendering it difficult if not impossible to reproduce. With such embodiments, individuals or institutions may create an "identifier stamp" or the like that uniquely identifies objects, with the stamp consisting of a color bar code or other spectrally identifying feature or aspect. This could be combined, for example, with a visible bar or other code, and with other information or bar code (or message), etc., that is discernible only with an instrument such as provided herein. In such embodiments, a subsurface bar code or spectral identification may be provided, with or without a visible code, message or data.

In yet another embodiment, inner layer(s) 604 are printed/formed with geometric two dimensional patterns that can be discerned as described herein by scanning the instrument, document or material, such as on two or more axis. In yet another embodiment, inner layer(s) 604 are printed/formed in multiple layers. Certain configurations of the measuring apparatus may be constructed to principally measure specific layers or thickness' of layers or spectral properties of layers. Thus, one measurement may produce one set of optical properties, while another measurement produces yet another set of optical properties, and so on rendering the instrument, document or material even more difficult to reproduce.

Such embodiments may be applicable to a wide class of objects. Although the foregoing discussion has focused on documents or negotiable instruments of paper or plastic such as currency or checks etc., it is equally applicable as an identification to works of art or objects or precious items or any material or object than can accept imprinting or other material preparation. Indeed, the quality of the printing of the original object need not be highly controlled either in color or in print quality. Since the imprint placed on the object is recorded both spectrally and spatially after the imprinting process (either as linear or multi-axis measurements) and recorded, it renders the identification mark difficult to reproduce.

Additionally, and particularly with respect to objects such as paintings, sculptures, and the like, it may be possible to determine optical properties as described herein in one or more locations, based on the constituent layers of the object (i.e., without forming special layers 602, 604, etc.). In general, it may be possible to optically characterize such objects, with optical characteristic data stored for later comparisons to determine if the object is genuine or counterfeit. Still additionally, it may be possible to use specially formed inner layers that include codes or other subsurface spectral characteristics that may be measured in accordance with the present invention, but which would not be discernible visually or by utilizing conventional spectrographic or colorimetry techniques. In such embodiments, the outer visible characteristics may completely mask the subsurface code or spectral identifier, which may remain hidden except when assessed as provided herein in order to detect for genuineness, etc. As will be apparent to those skilled in the art, certain refinements may be made in accordance with the present invention. For example, a central light source fiber optic is utilized in certain preferred embodiments, but other light source arrangements (such as a plurality of light source fibers, etc.). In addition, lookup tables are utilized for various aspects of the present invention, but polynomial type calculations could similarly be employed. Thus, although various preferred embodiments of the present invention have been disclosed for illustrative purposes, those skilled in the art will appreciate that various modifications, additions and/or substitutions are possible without departing from the scope and spirit of the present invention as disclosed in the claims. In addition, while various embodiments utilize light principally in the visible light spectrum, the present invention is not necessarily limited to all or part of such visible light spectrum, and may include radiant energy not within such visible light spectrum.

Reference is made to copending applications filed on even date herewith for Apparatus and Method for Measuring Optical Characteristics of Teeth, and for Apparatus and Method for Measuring Optical Characteristics of an Object, both by the inventors hereof, which are hereby incorporated by reference.

What is claimed is:

1. A method for determining whether an object is genuine, comprising the steps of:

measuring optical properties of the object at one or more locations with a probe, at least one of the one or more locations having a first region of material that is translucent or semitranslucent, wherein the measured optical properties include one or more properties not readily discernible from a visual inspection of the object, and wherein the probe includes at least one source that emits light on an outer surface of the object, wherein the probe includes at least one receiver that receives light from the object, wherein the measuring step generates optical characteristics data based on spectral characteristics of a second region of material that is under the first region of material; and comparing the measured optical properties with recorded optical properties, wherein based on the comparison a determination is made whether the object is genuine.

2. The method of claim 1, wherein the probe comprises a plurality of source/receiver elements, wherein the source/receiver elements are arranged in one or more rings around a central source/receiver element.

3. The method of claim 2, wherein the source/receiver elements comprise fiber optic source/receiver elements.

4. The method of claim 1, wherein the probe includes at least two receivers, wherein at least one receiver has a first numerical aperture, where at least one receiver has a second numerical aperture, wherein the first numerical aperture is different from the second numerical aperture.

5. The method of claim 1, wherein light received by the probe is coupled to one or more sensing elements comprising light-to-frequency converters.

6. The method of claim 1, wherein the optical properties are measured a predetermined distance from a location marker on the object.

7. The method of claim 1, wherein where the one or more locations are located on the object is not identified on the object.

8. The method of claim 1, wherein the determination is made based on one or more acceptance criteria.

9. The method of claim 8, wherein the acceptance criteria comprise a delta E value.

10. The method of claim 8, wherein the acceptance criteria comprise a threshold value.

11. The method of claim 1, wherein the object comprises an art work.

12. The method of claim 1, wherein the object comprises a painting.

13. The method of claim 1, wherein the object comprises a sculpture.

14. The method of claim 1, wherein the object comprises a passport.

15. The method of claim 1, wherein the object comprises a credit card.

16. The method of claim 1, wherein the object comprises a check.

17. The method of claim 1, wherein the object comprises a traveler's check.

18. The method of claim 1, wherein the object comprises a security.

19. The method of claim 1, wherein the object comprises a stock certificate.

20. The method of claim 1, wherein the object comprises a bond.

21. The method of claim 1, wherein the object comprises currency.

22. The method of claim 1, wherein the object comprises a negotiable instrument.

23. The method of claim 1, wherein the object comprises a document on which a pigment-containing material is deposited, wherein the recorded optical properties are measured after the pigment-containing material is deposited, wherein the optical properties are measured at a time subsequent to the rime when the pigment-containing material is deposited.

24. The method of claim 23, wherein the pigment-containing material comprises paint.

25. The method of claim 23, wherein the pigment-containing material comprises ink.

26. The method of claim 1, wherein the measured optical properties include translucency, wherein measured spectral properties are adjusted based on the measured translucency.

27. The method of claim 1, wherein the measured optical properties include gloss, wherein measured spectral properties are adjusted based on the measured gloss.

28. The method of claim 1, wherein the measured optical properties include translucency and gloss, wherein measured spectral properties are adjusted based on the measured translucency and gloss.

29. A method for determining whether an object is genuine, comprising the steps of:

measuring optical properties of the object at one or more locations with a probe, at least one of the one or more locations having a first region of material that is translucent or semitranslucent, wherein the measured optical properties include a plurality of measurements including at least a first measurement when the probe is a first distance from the object and at least a second measurement when the probe is a second distance from the object and at least one measurement based on spectral characteristics of a second region of material that is under the first region of material; and comparing the measured optical properties with recorded optical properties, wherein based on the comparison a determination is made whether the object is genuine.

30. The method of claim 29, wherein the probe includes at least one source that emits light on a first area of an outer surface of the object, wherein the probe includes at least one receiver that receives light reflected from a second area of the outer surface of the object, wherein the measuring step includes at least one measurement taken when the first area does not intersect with the second area.

31. The method of claim 29, wherein the plurality of measurements include measurements wherein the probe and the object are moving relative to each other.

32. The method of claim 29, wherein the probe comprises a plurality of source/receiver elements, wherein the source/receiver elements are arranged in one or more rings around a central source/receiver element.

33. The method of claim 32, wherein the source/receiver elements comprise fiber optic source/receiver elements.

34. The method of claim 29, wherein the probe includes at least two receivers, wherein at least one receiver has a first numerical aperture, where at least one receiver has a second numerical aperture, wherein the first numerical aperture is different from the second numerical aperture.

35. The method of claim 29, wherein light received by the probe is coupled to one or more sensing elements comprising light-to-frequency converters.

36. The method of claim 29, wherein the optical properties are measured a predetermined distance from a location marker on the object.

37. The method of claim 29, wherein where the one or more locations are located on the object is not identified on the object.

38. The method of claim 29, wherein the determination is made based on one or more acceptance criteria.

39. The method of claim 38, wherein the acceptance criteria comprise a delta E value.

40. The method of claim 38, wherein the acceptance criteria comprise a threshold value.

41. The method of claim 29, wherein the object comprises an art work.

42. The method of claim 29, wherein the object comprises a painting.

43. The method of claim 29, wherein the object comprises a sculpture.

44. The method of claim 29, wherein the object comprises a passport.

45. The method of claim 29, wherein the object comprises a credit card.

46. The method of claim 29, wherein the object comprises a check.

47. The method of claim 29, wherein the object comprises a traveler's check.

48. The method of claim 29, wherein the object comprises a security.

49. The method of claim 29, wherein the object comprises a stock certificate.

50. The method of claim 29, wherein the object comprises a bond.

51. The method of claim 29, wherein the object comprises currency.

52. The method of claim 29, wherein the object comprises a negotiable instrument.

53. The method of claim 29, wherein the object comprises a document on which a pigment-containing material is deposited, wherein the recorded optical properties are measured after the pigment-containing material is deposited, wherein the optical properties are measured at a time subsequent to the time when the pigment-containing material is deposited.

54. The method of claim 53, wherein the pigment-containing material comprises paint.

55. The method of claim 53, wherein the pigment-containing material comprises ink.

56. The method of claim 29, wherein the measured optical properties include translucency, wherein measured spectral properties are adjusted based on the measured translucency.

57. The method of claim 29, wherein the measured optical properties include gloss, wherein measured spectral properties are adjusted based on the measured gloss.

58. The method of claim 29, wherein the measured optical properties include translucency and gloss, wherein measured spectral properties are adjusted based on the measured translucency and gloss.

* * * * *